(12) United States Patent
Xia

(10) Patent No.: US 11,201,290 B2
(45) Date of Patent: Dec. 14, 2021

(54) TETRAPHENYLENE ANTHRACENE COMPOUNDS

(71) Applicant: BEIJING SUMMER SPROUT TECHNOLOGY CO., LTD., Beijing (CN)

(72) Inventor: Chuanjun Xia, Lawrenceville, NJ (US)

(73) Assignee: BEIJING SUMMER SPROUT TECHNOLOGY CO., LTD., Beijing (CN)

(*) Notice: Subject to any disclaimer, the term of this patent is extended or adjusted under 35 U.S.C. 154(b) by 431 days.

(21) Appl. No.: 16/157,121

(22) Filed: Oct. 11, 2018

(65) Prior Publication Data

US 2019/0115541 A1    Apr. 18, 2019

Related U.S. Application Data

(60) Provisional application No. 62/571,763, filed on Oct. 12, 2017.

(51) Int. Cl.
| | |
|---|---|
| *H01L 51/50* | (2006.01) |
| *H01L 51/00* | (2006.01) |
| *C07C 13/62* | (2006.01) |
| *C09K 11/06* | (2006.01) |
| *C07D 491/04* | (2006.01) |

(Continued)

(52) U.S. Cl.
CPC .......... *H01L 51/0055* (2013.01); *C07C 13/62* (2013.01); *C07D 209/58* (2013.01); *C07D 235/08* (2013.01); *C07D 251/24* (2013.01); *C07D 307/91* (2013.01); *C07D 333/50* (2013.01); *C07D 401/04* (2013.01); *C07D 471/04* (2013.01); *C07D 487/04* (2013.01); *C07D 491/04* (2013.01); *C07D 495/04* (2013.01); *C09K 11/06* (2013.01); *H01L 51/0058* (2013.01); *C07C 2603/24* (2017.05); *C07C 2603/40* (2017.05); *C07C 2603/50* (2017.05); *C07C 2603/52* (2017.05); *C09K 2211/1007* (2013.01);

(Continued)

(58) Field of Classification Search
None
See application file for complete search history.

(56) References Cited

U.S. PATENT DOCUMENTS

| 5,703,436 A | 12/1997 | Forrest et al. |
| 5,707,745 A | 1/1998 | Forrest et al. |

(Continued)

FOREIGN PATENT DOCUMENTS

| CN | 110713492 | | 1/2020 | |
| JP | 2005-174675 | * | 6/2005 | ............. H01L 51/50 |
| JP | 2005-5174675 | * | 6/2005 | ............. H05B 33/22 |

OTHER PUBLICATIONS

Tang, C. W. et al., "Organic electroluminescent diodes", Applied Physics Letters, 51(12): 913-915 (1987).

(Continued)

*Primary Examiner* — Gregory D Clark
(74) *Attorney, Agent, or Firm* — Workman Nydegger

(57) ABSTRACT

Novel tetraphenylene anthracene compounds are disclosed, which can be used as charge transporting materials, emitters, hosts in an organic electroluminescent device. These novel compounds offer better device performance. Also disclosed are an electroluminescent device and a formulation.

15 Claims, 3 Drawing Sheets

Figure 1:
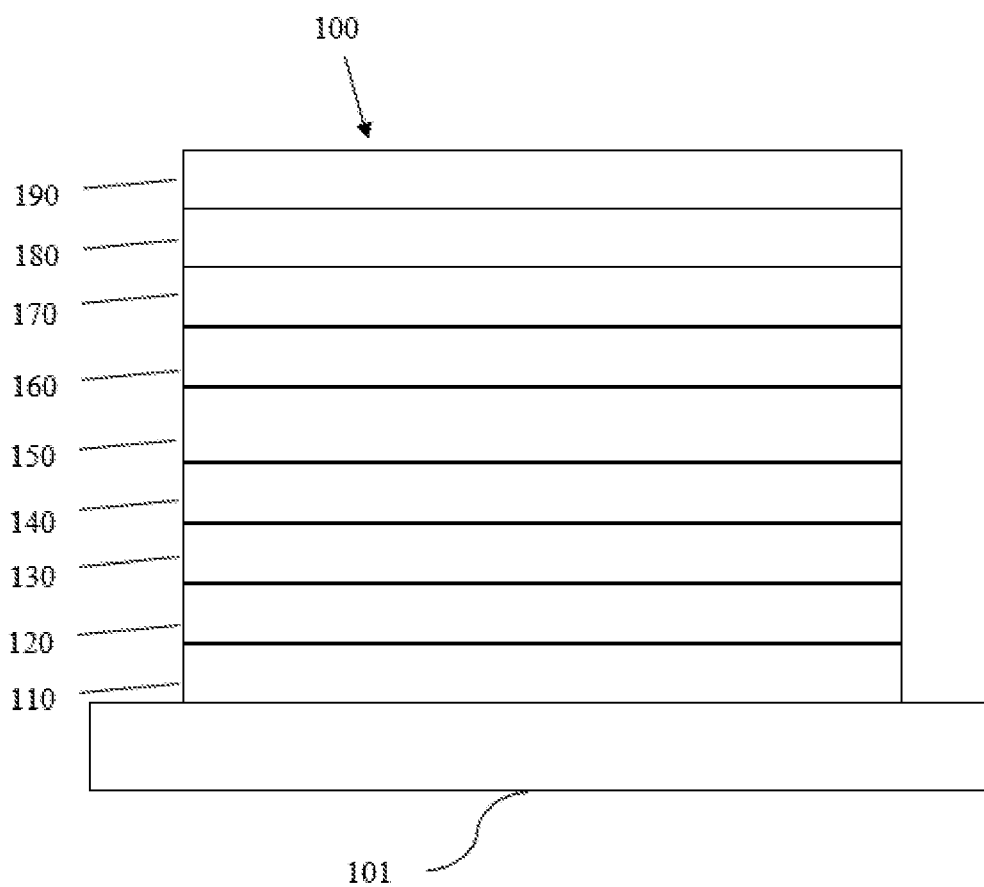

(51) Int. Cl.

| | |
|---|---|
| *C07D 487/04* | (2006.01) |
| *C07D 251/24* | (2006.01) |
| *C07D 307/91* | (2006.01) |
| *C07D 235/08* | (2006.01) |
| *C07D 471/04* | (2006.01) |
| *C07D 495/04* | (2006.01) |
| *C07D 209/58* | (2006.01) |
| *C07D 401/04* | (2006.01) |
| *C07D 333/50* | (2006.01) |

(52) U.S. Cl.
CPC ... *C09K 2211/1011* (2013.01); *H01L 51/5012* (2013.01); *H01L 51/5056* (2013.01); *H01L 51/5072* (2013.01)

(56) References Cited

U.S. PATENT DOCUMENTS

| | | |
|---|---|---|
| 5,844,363 A | 12/1998 | Gu et al. |
| 6,097,147 A | 8/2000 | Baldo et al. |
| 6,303,238 B1 | 10/2001 | Thompson et al. |
| 6,416,887 B1 | 7/2002 | Tokito et al. |
| 7,279,704 B2 | 10/2007 | Walters et al. |
| 7,968,146 B2 | 6/2011 | Wagner et al. |
| 2001/0006741 A1 | 7/2001 | Ishikawa et al. |
| 2003/0230980 A1 | 12/2003 | Forrest et al. |
| 2004/0174116 A1 | 9/2004 | Lu et al. |
| 2005/0112407 A1 | 5/2005 | Ogasawara et al. |
| 2014/0131665 A1 | 5/2014 | Xia et al. |
| 2014/0158992 A1 | 6/2014 | Xia et al. |
| 2015/0349273 A1 | 12/2015 | Hung et al. |
| 2016/0013422 A1 | 1/2016 | Kwong et al. |
| 2016/0343951 A1 | 11/2016 | Kwong et al. |
| 2016/0359122 A1 | 12/2016 | Boudreault et al. |
| 2017/0018721 A1 | 1/2017 | Tsang et al. |
| 2017/0077409 A1 | 5/2017 | Kwong et al. |
| 2017/0162816 A1 | 6/2017 | Kim et al. |
| 2018/0108844 A1 | 4/2018 | Lee et al. |
| 2019/0036031 A1 | 1/2019 | Wolohan et al. |
| 2019/0100544 A1 | 4/2019 | Xia |
| 2019/0123286 A1 | 4/2019 | Xia |
| 2019/0185412 A1 | 6/2019 | Xia |

OTHER PUBLICATIONS

Hiroki Uoyama et al., "Highly efficient organic light-emitting diodes from delayed fluorescence", Nature, vol. 492, pp. 234-238 (2012).

Shulei Pan, et al., "Synthesis of 2-substituted tetraphenylenes via transitionmetal-catalyzed derivatization of tetraphenylene", Beilstein Journal of Organic Chemistry, 2016, 12, 1302-1308.

\* cited by examiner

TETRAPHENYLENE ANTHRACENE COMPOUNDS

This application claims the benefit of U.S. Provisional Application No. 62/571,763, filed Oct. 12, 2017, the entire content of which is incorporated herein by reference.

1 FIELD OF THE INVENTION

The present invention relates to a compound for organic electronic devices, such as organic light emitting devices. More specifically, the present invention relates to tetraphenylene anthracene compounds, an organic electroluminescent device comprising the compounds and a formulation.

2 BACKGROUND ART

An organic electronic device is preferably selected from the group consisting of organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process, such as spin-coating, ink-jet printing, and nozzle printing. Small molecule OLEDs can also be fabricated by solution process if the materials can be dissolved or dispersed in solvents.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Tetraphenylene consists of four benzene rings that are ortho-annulated to form an eight-membered ring. It has a nonplanar saddle-shaped structure, with the two opposite pairs of benzene rings oriented above or below the average plane of the molecule. Due to their unique geometry, tetraphenylene and its derivatives may be used in OLED applications. However, their use in OLED materials has not been widely explored. This invention discloses novel anthracene compounds containing tetraphenylene building block. The saddle-shaped structure of tetraphenylene reduces solid state packing and improves the chemical stability of anthracene toward oxygen. Therefore, these novel compounds offer better device performance.

3 SUMMARY OF THE INVENTION

The present invention aims to provide a new series of tetraphenylene anthracene compounds to solve at least part of the above problems. The compounds can be used as charge transporting materials, hosts, emitters in an organic electroluminescent device. These novel compounds offer better device performance.

According to an embodiment of the present invention, a compound having formula 1 is disclosed:

Formula 1

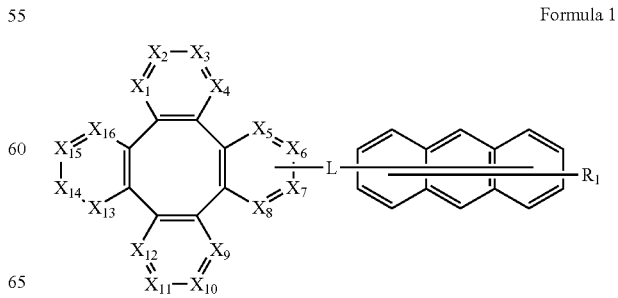

Wherein $X_1$ to $X_{16}$ are each independently selected for the group consisting of C, CR, and N;

L is selected from the group consisting of a single bond, a substituted or unsubstituted aryl group having 6 to 30 carbon atoms, a substituted or unsubstituted heteroaryl group having 4 to 30 carbon atoms, a substituted or unsubstituted alkylsilyl group having 3 to 20 carbon atoms, a substituted or unsubstituted arylsilyl group having 6 to 20 carbon atoms;

$R_1$ represents mono, multi substitution or no substitution;

R and $R_1$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

According to another embodiment, an electroluminescent device is disclosed, which comprises:

an anode, a cathode, and an organic layer, disposed between the anode and the cathode, comprising a compound according to formula 1:

Formula 1

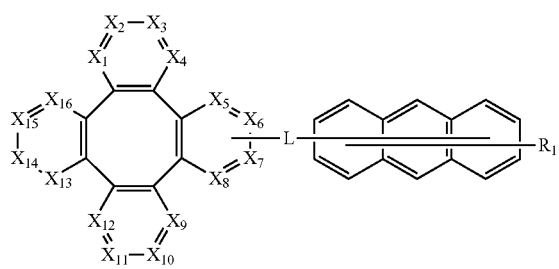

Wherein $X_1$ to $X_{16}$ are each independently selected for the group consisting of C, CR, and N;

L is selected from the group consisting of a single bond, a substituted or unsubstituted aryl group having 6 to 30 carbon atoms, a substituted or unsubstituted heteroaryl group having 4 to 30 carbon atoms, a substituted or unsubstituted alkylsilyl group having 3 to 20 carbon atoms, a substituted or unsubstituted arylsilyl group having 6 to 20 carbon atoms;

$R_1$ represents mono, multi substitution or no substitution;

R and $R_1$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

According to yet another embodiment, a formulation comprising a compound according to formula 1 is also disclosed.

The novel tetraphenylene anthracene compounds disclosed in the present invention can be used as charge transporting materials, emitters, hosts in an organic electroluminescent device. These novel compounds offer better device performance.

4 BRIEF DESCRIPTION OF THE DRAWINGS

FIG. 1 schematically shows an organic light emitting device that can incorporate the compound and the formulation disclosed herein.

Figure 2:
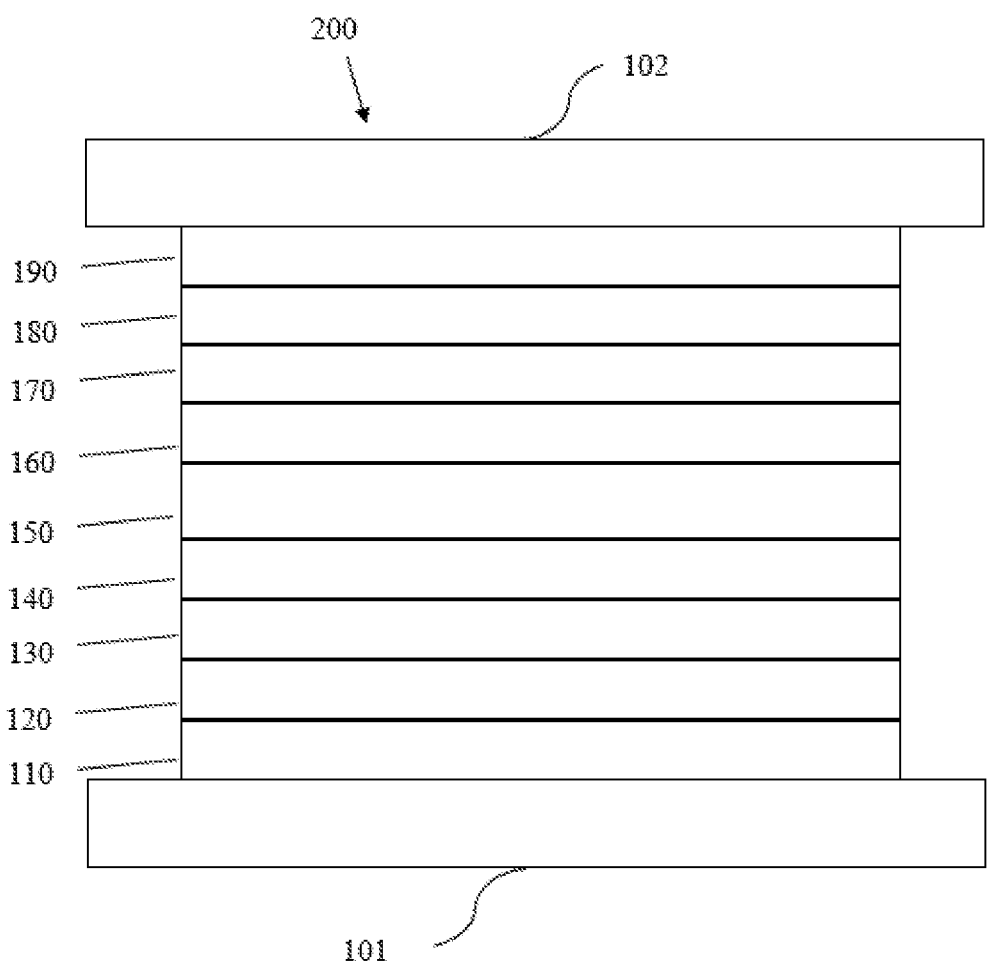

FIG. 2 schematically shows another organic light emitting device that can incorporate the compound and the formulation disclosed herein.

Figure 3:
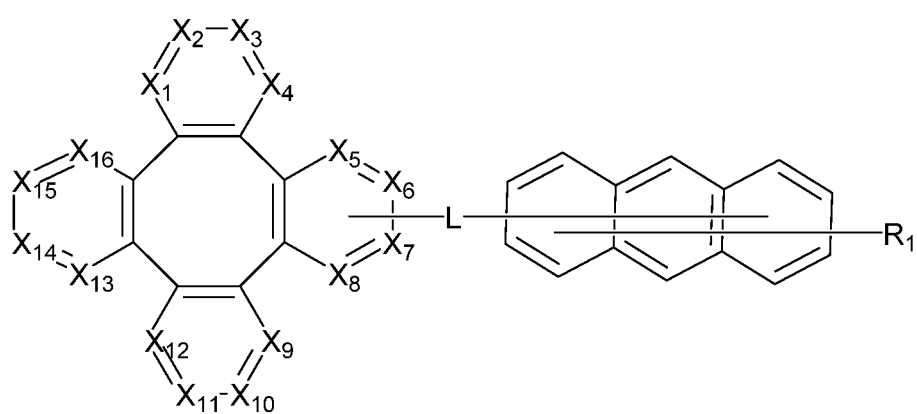

FIG. 3 shows the formula 1 of the compound disclosed herein.

5 DETAILED DESCRIPTION

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

An OLED can be encapsulated by a barrier layer to protect it from harmful species from the environment such as moisture and oxygen. FIG. 2 schematically shows the organic light emitting device 200 without limitation. FIG. 2 differs from FIG. 1 in that the organic light emitting device 200 include a barrier layer 102, which is above the cathode 190. Any material that can provide the barrier function can be used as the barrier layer such as glass and organic-inorganic hybrid layers. The barrier layer should be placed directly or indirectly outside of the OLED device. Multi-layer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multi substitutions refer to a range that includes a double substitution, up to the maximum available substitutions.

In the compounds mentioned in this disclosure, the expression that adjacent substituents are optionally joined to form a ring is intended to be taken to mean that two radicals are linked to each other by a chemical bond. This is illustrated by the following scheme:

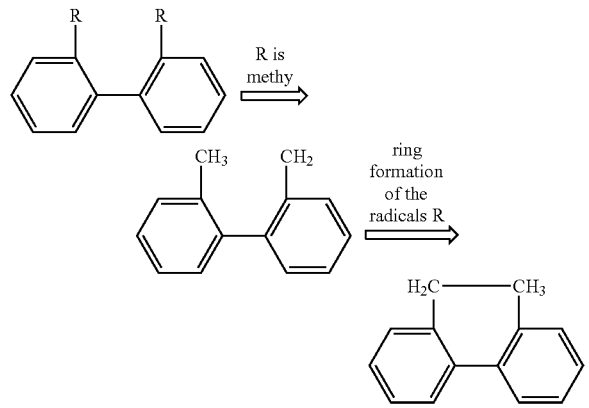

Furthermore, the expression that adjacent substituents are optionally joined to form a ring is also intended to be taken to mean that in the case where one of the two radicals represents hydrogen, the second radical is bonded at a position to which the hydrogen atom was bonded, with formation of a ring. This is illustrated by the following scheme:

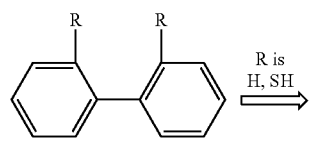

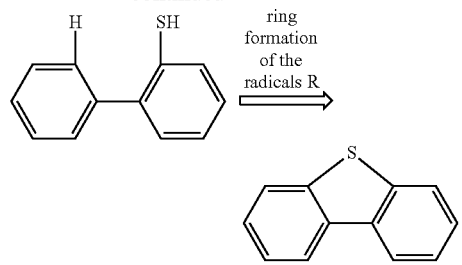

According to an embodiment of the present invention, a compound having formula 1 is disclosed:

Formula 1

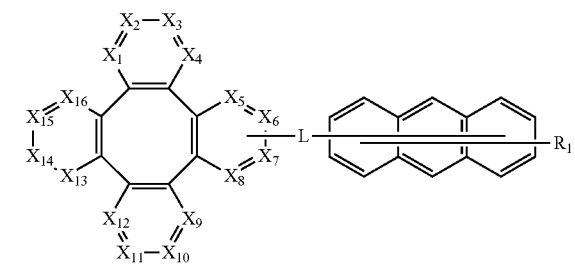

Wherein $X_1$ to $X_{16}$ are each independently selected for the group consisting of C, CR, and N;

L is selected from the group consisting of a single bond, a substituted or unsubstituted aryl group having 6 to 30 carbon atoms, a substituted or unsubstituted heteroaryl group having 4 to 30 carbon atoms, a substituted or unsubstituted alkylsilyl group having 3 to 20 carbon atoms, a substituted or unsubstituted arylsilyl group having 6 to 20 carbon atoms;

$R_1$ represents mono, multi substitution or no substitution;

R and $R_1$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

In one embodiment, wherein none of $X_1$ to $X_{16}$ is N.

In one embodiment, wherein at least one of $X_1$ to $X_{16}$ is N.

In one embodiment, wherein L is selected from the group consisting of:

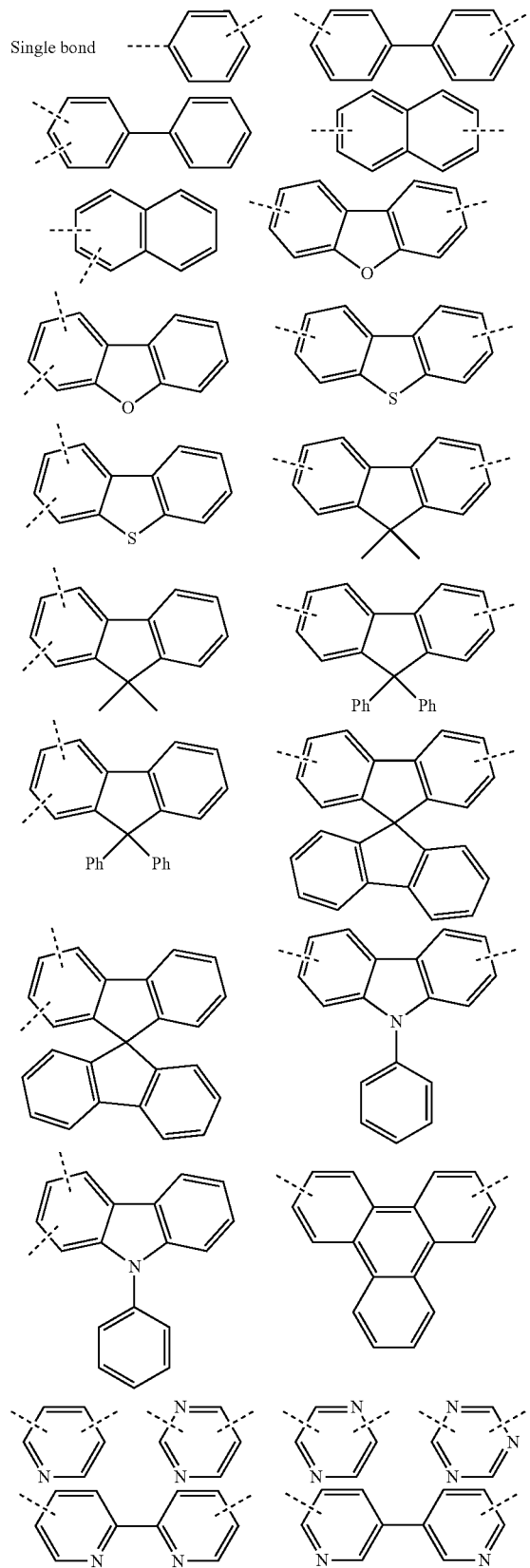

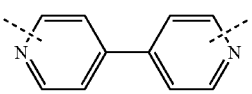

and combinations thereof.

In one embodiment, wherein $R_1$ is a substituted or unsubstituted aryl group having 6 to 30 carbon atoms, a substituted or unsubstituted heteroaryl group having 6 to 30 carbon atoms.

In one embodiment, wherein $R_1$ is a substituted or unsubstituted aryl group comprising a fused ring system.

In one embodiment, wherein $R_1$ is selected from the group consisting of phenyl, biphenyl, terphenyl, pyridine, pyrimidine, triazine, dibenzofuran, dibenzothiophene, carbazole, fluorene, triphenylene, phenanthrene, phenanthroline, pyrene, and combinations thereof.

In one embodiment, wherein L is connected to the $9^{th}$ position of anthracene and $R_1$ is connected to the $10^{th}$ position of anthracene.

In one embodiment, wherein the compound is selected from the group consisting of:

Compound 1

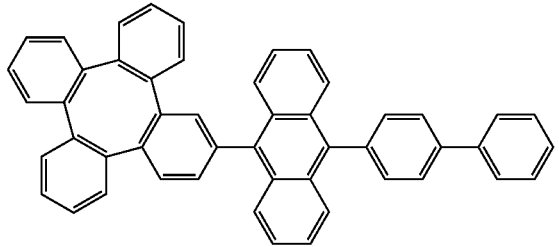

Compound 2

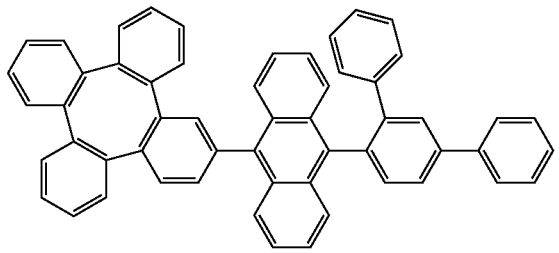

Compound 3

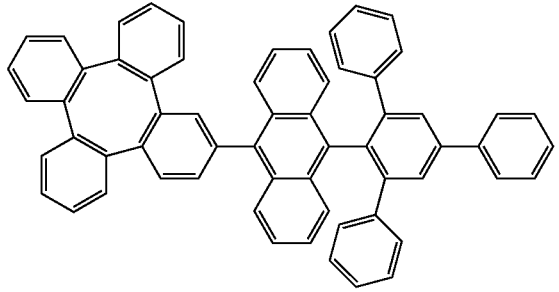

Compound 4
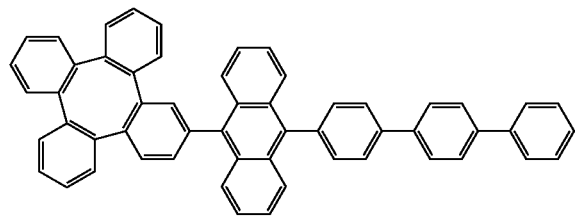
Compound 5
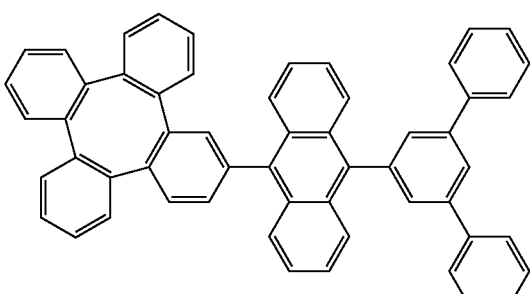
Compound 6
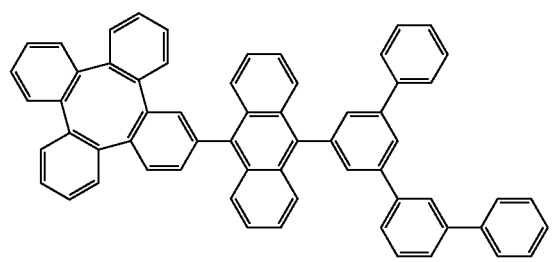
Compound 7
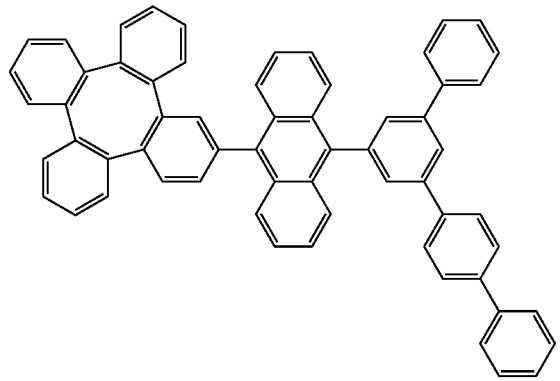
Compound 8
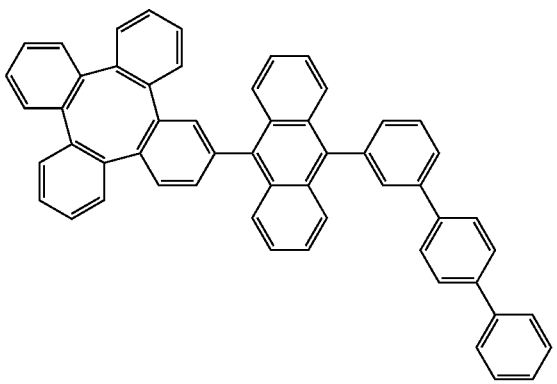
Compound 9
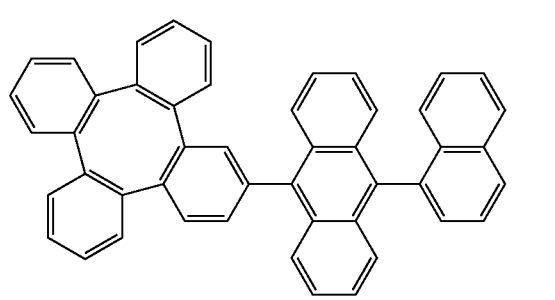
Compound 10
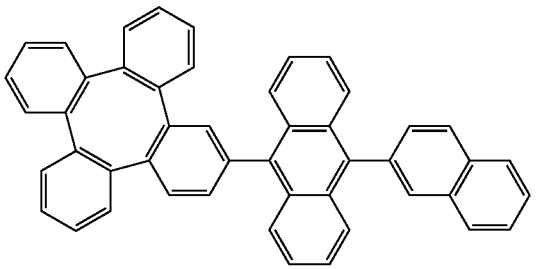
Compound 11
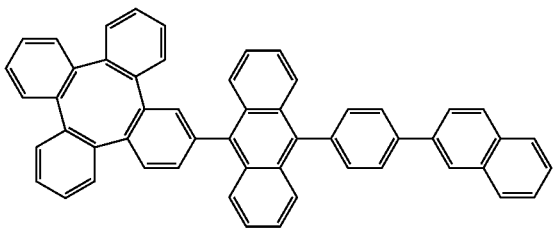
Compound 12
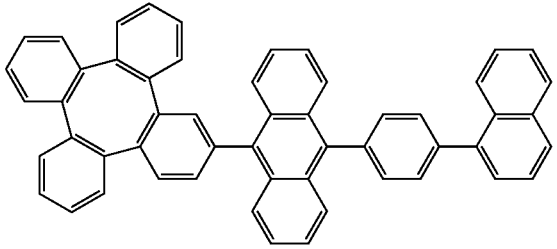

Compound 13
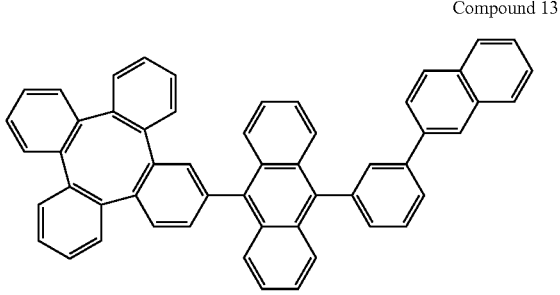 [SMILES: c1cc(-c2ccc3ccccc3c2)cc(-c2c3ccccc3c(-c3ncc4c(n3)-c3ccccc3-c3ccccc3-c3ccccc3-4)c3ccccc23)c1]
Compound 14
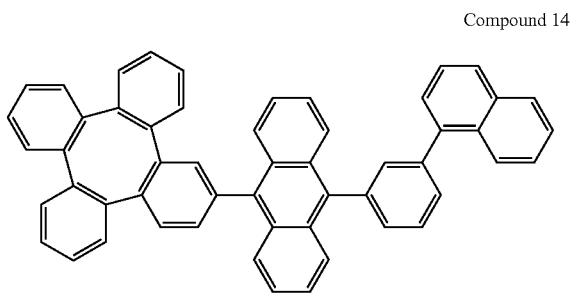
Compound 15
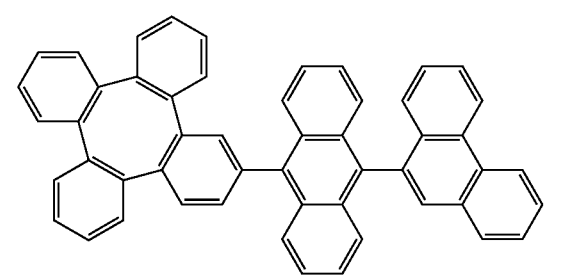
Compound 16
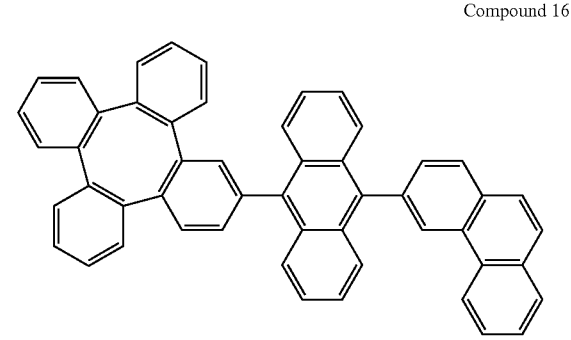
Compound 17
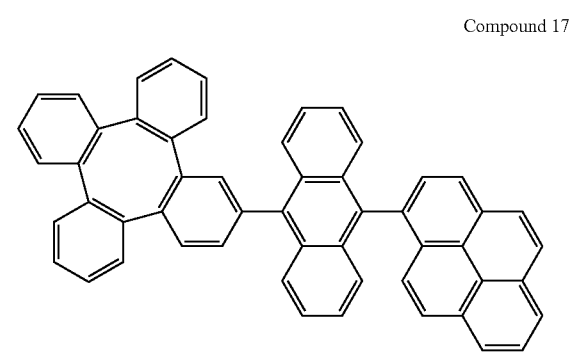
Compound 18
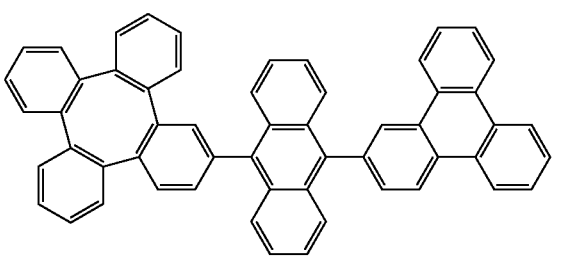
Compound 19
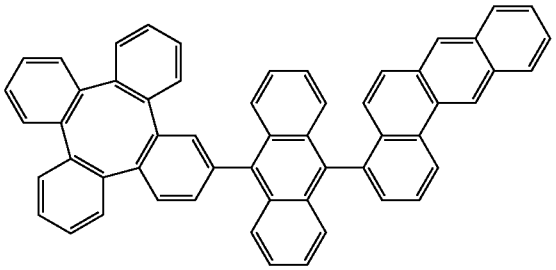
Compound 20
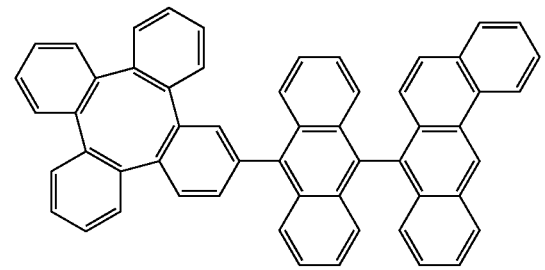
Compound 21
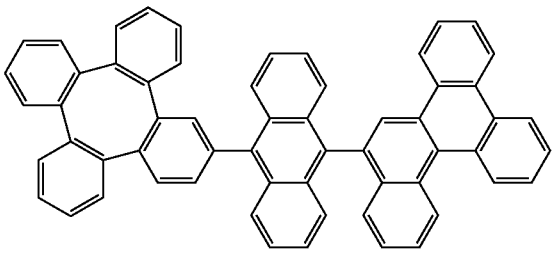
Compound 22
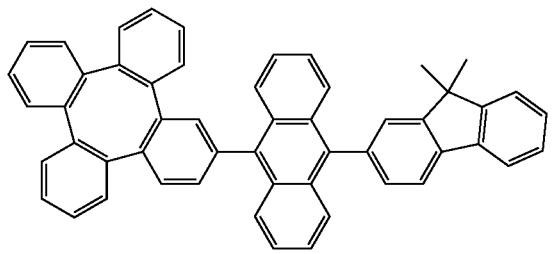

Compound 23
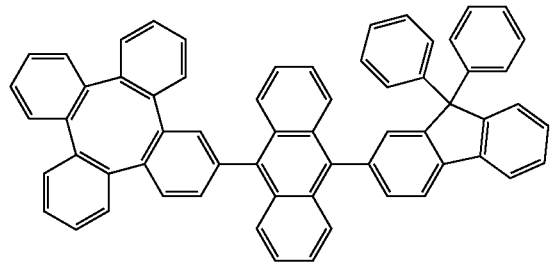
Compound 24
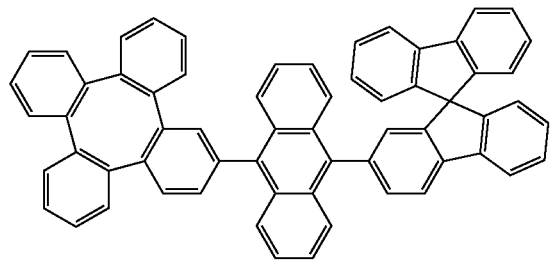
Compound 25
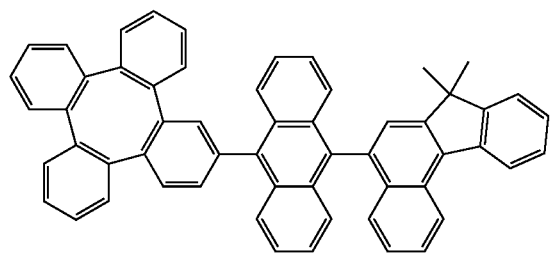
Compound 26
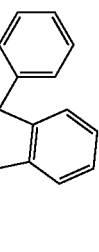
Compound 27
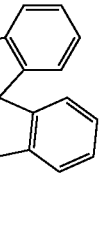
Compound 28
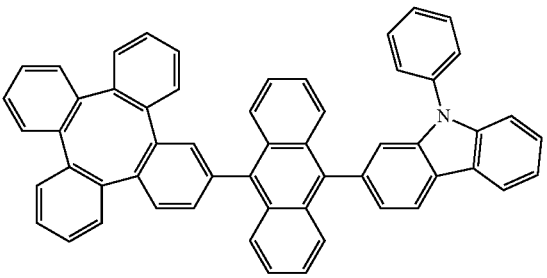
Compound 29
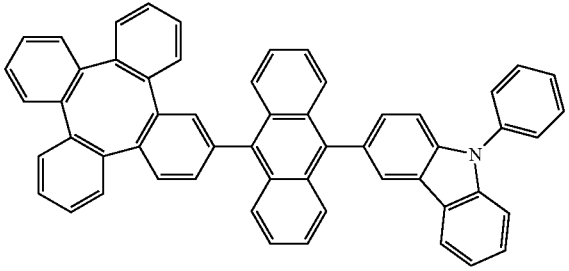
Compound 30
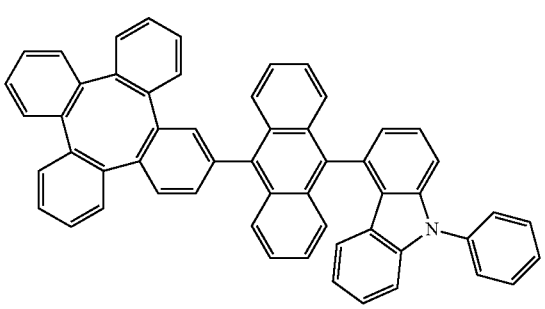
Compound 31
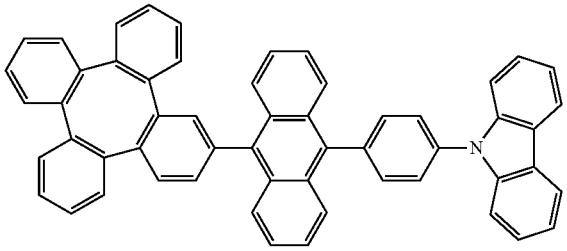
Compound 32
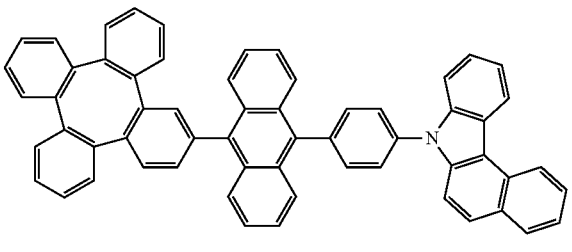

Compound 33
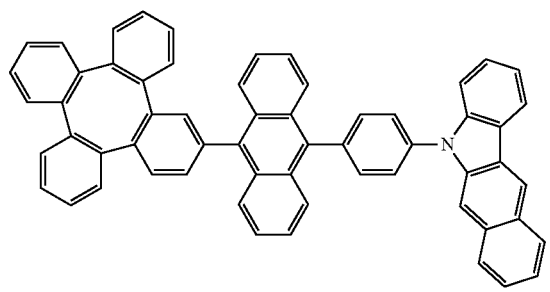
Compound 34
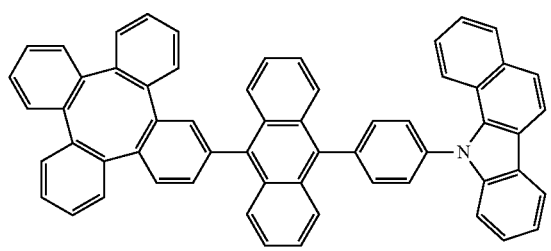
Compound 35
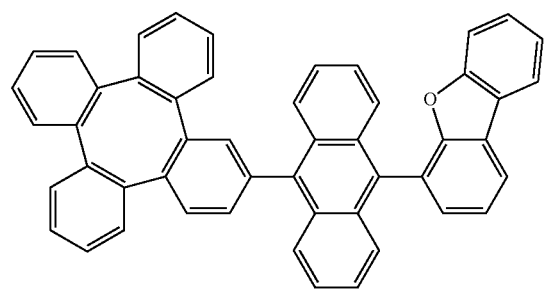
Compound 36
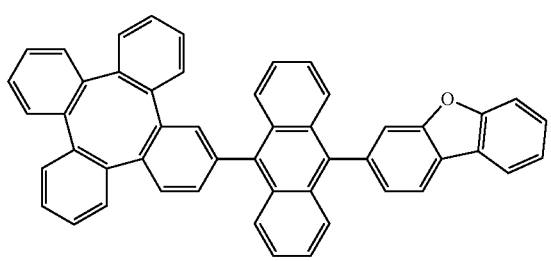
Compound 37
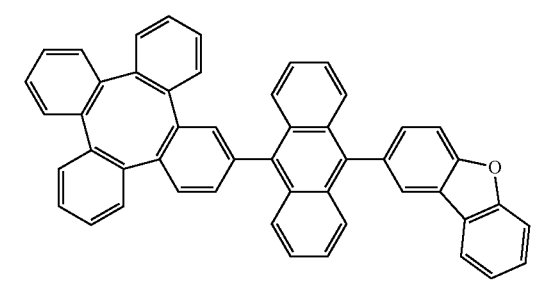
Compound 38
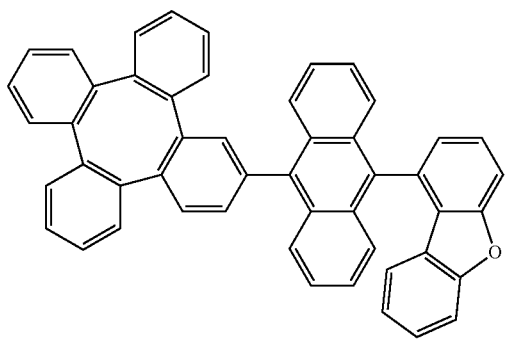
Compound 39
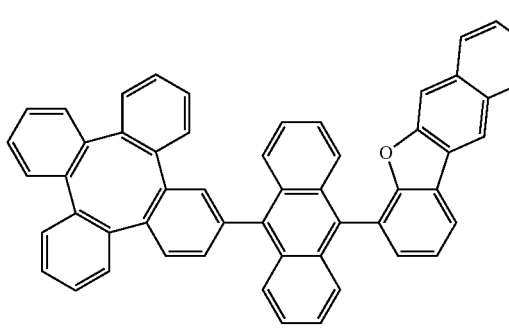
Compound 40
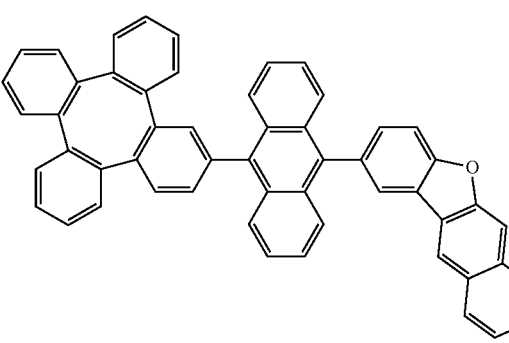
Compound 41
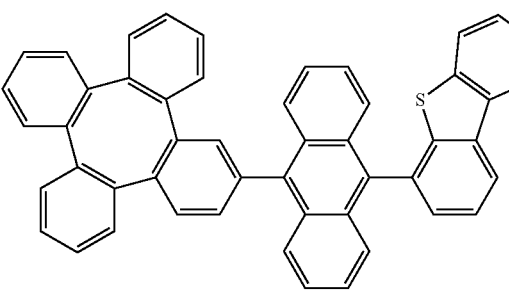
Compound 42
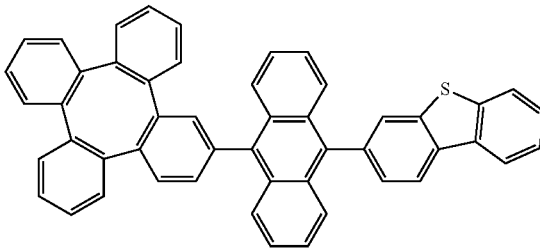

Compound 43
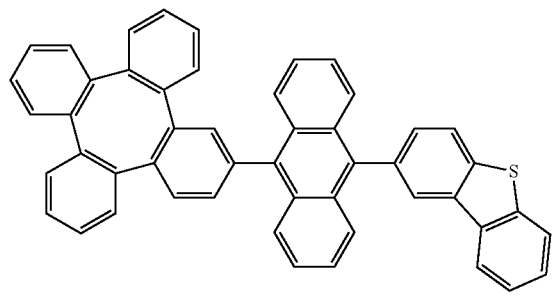
Compound 44
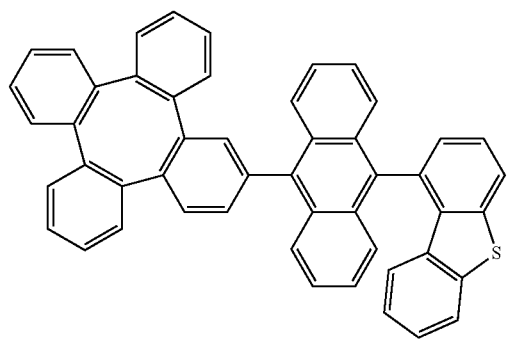
Compound 45
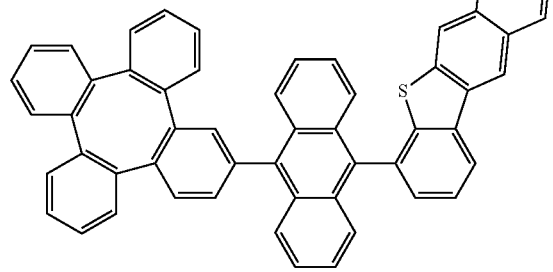
Compound 46
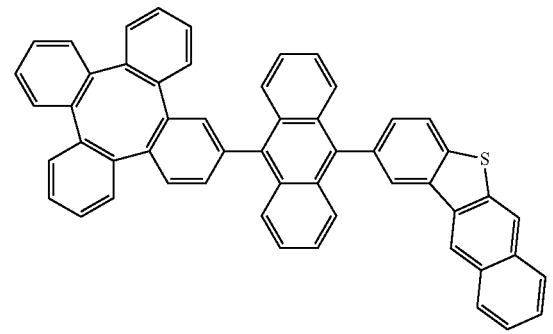
Compound 47
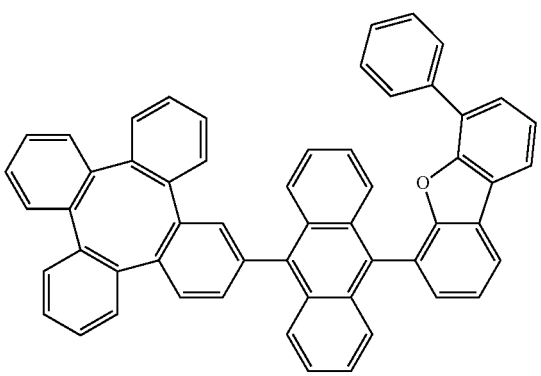
Compound 48
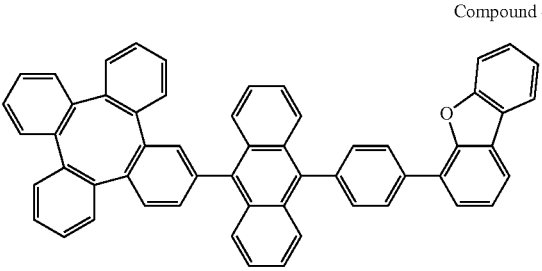
Compound 49
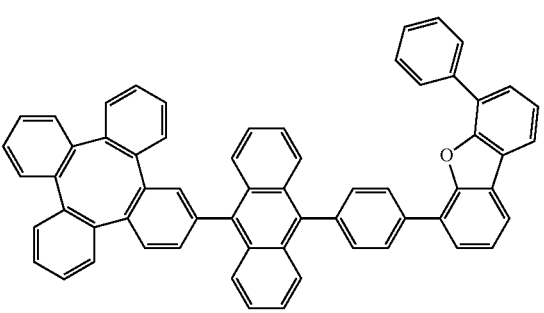
Compound 50
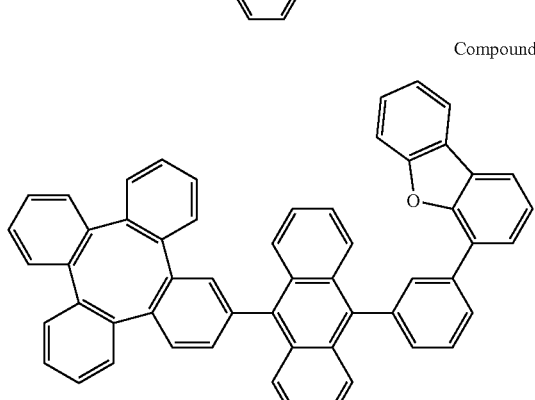
Compound 51
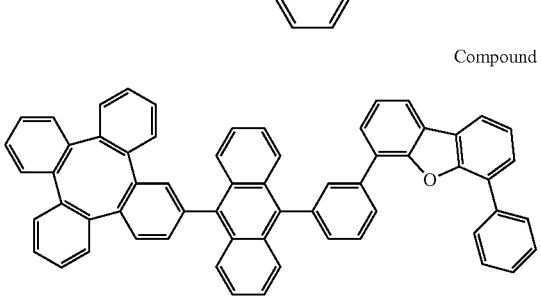

Compound 52
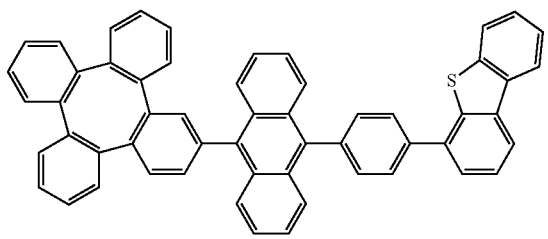
Compound 53
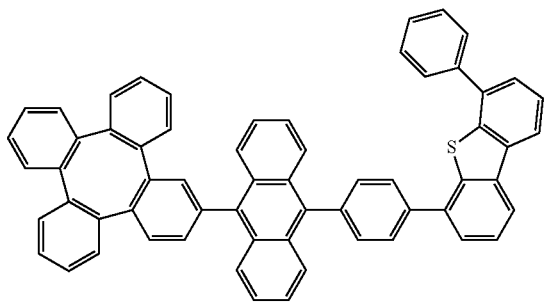
Compound 54
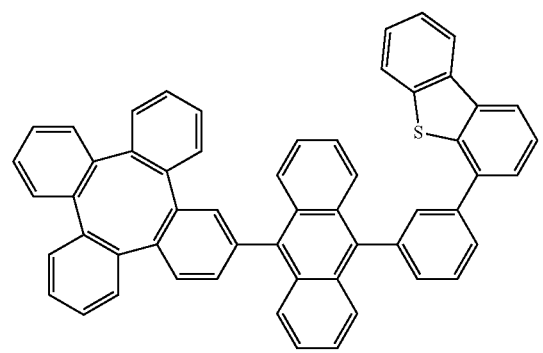
Compound 55
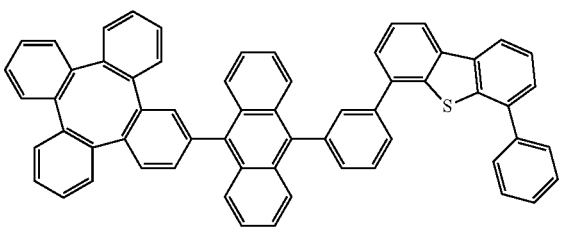
Compound 56
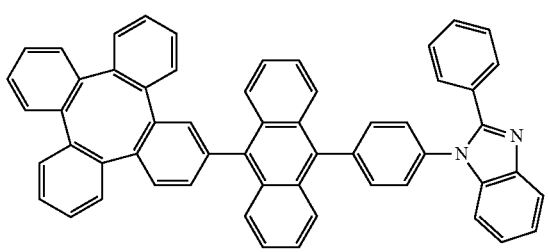
Compound 57
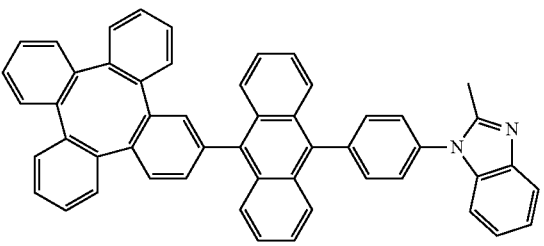
Compound 58
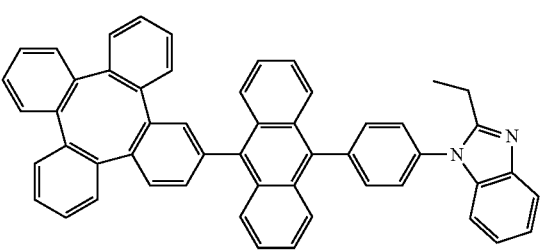
Compound 59
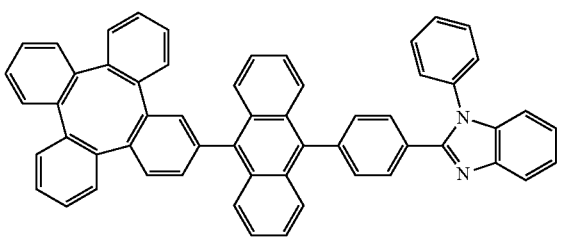
Compound 60
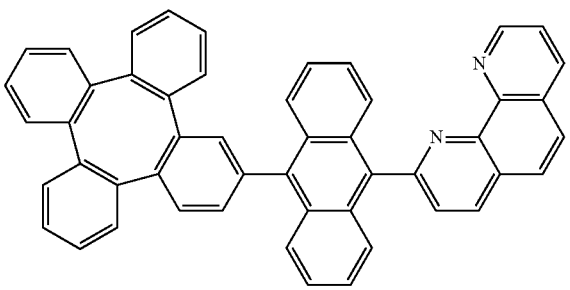
Compound 61

Compound 62
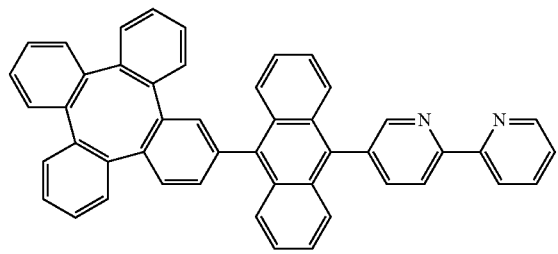
Compound 63
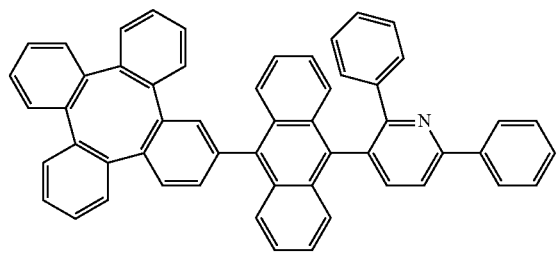
Compound 64
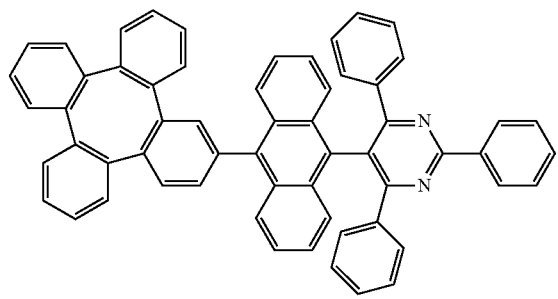
Compound 65
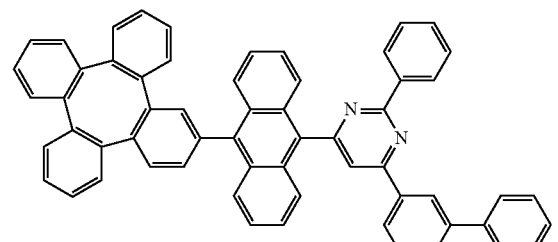
Compound 66
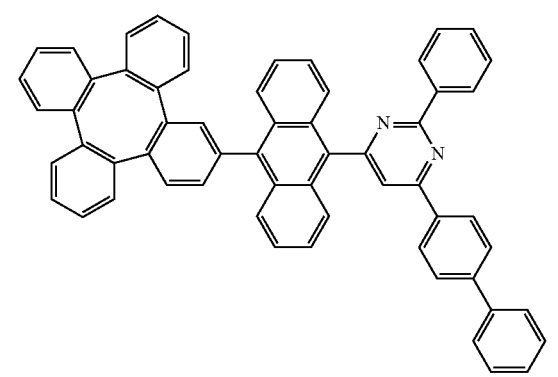
Compound 67
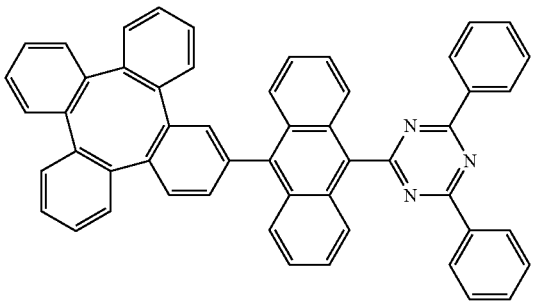
Compound 68
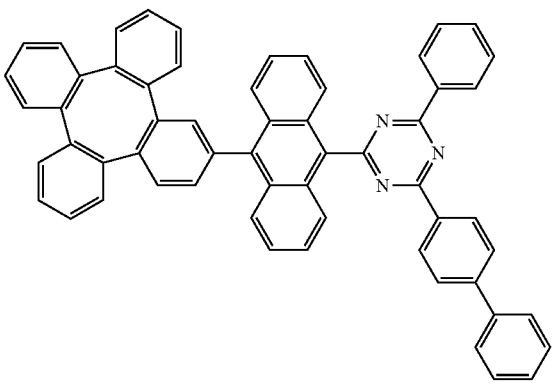
Compound 69
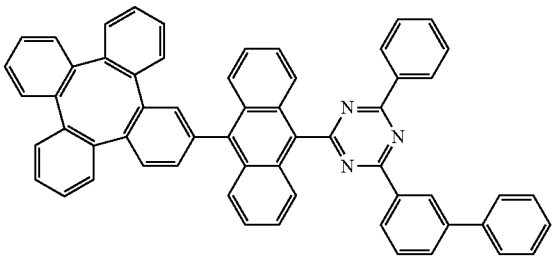
Compound 70
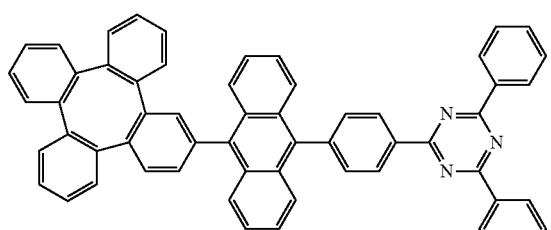
Compound 71
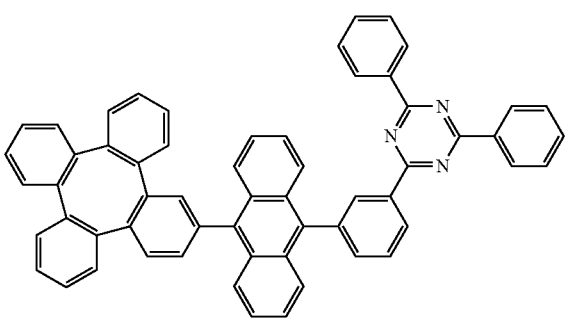

Compound 72
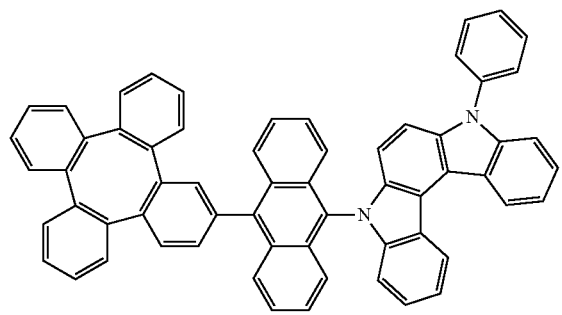
Compound 73
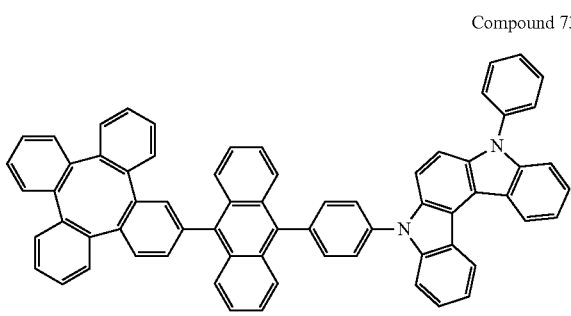
Compound 74
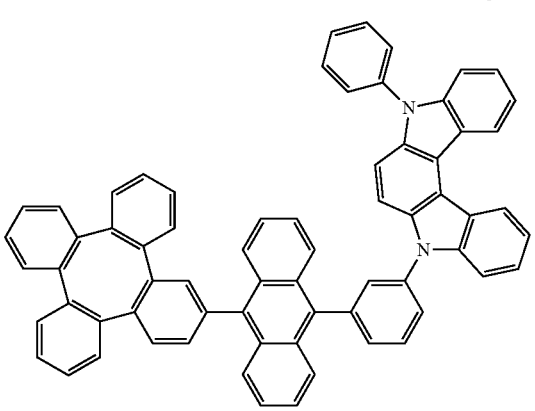
Compound 75
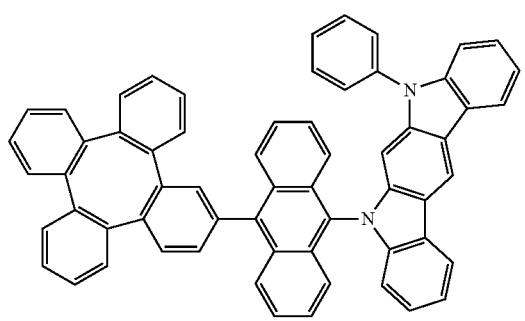
Compound 76
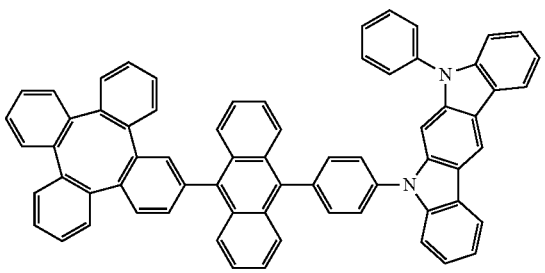
Compound 77
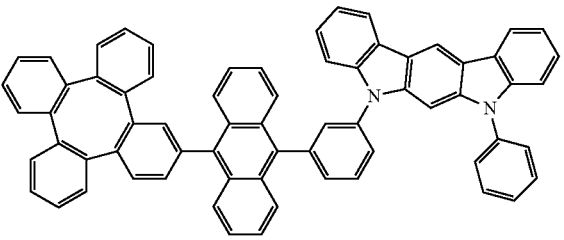
Compound 78
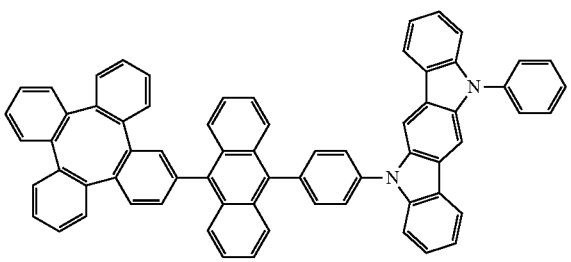
Compound 79
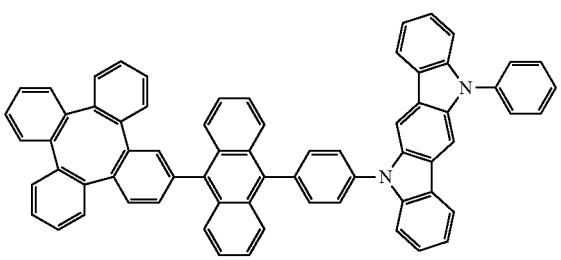
Compound 80
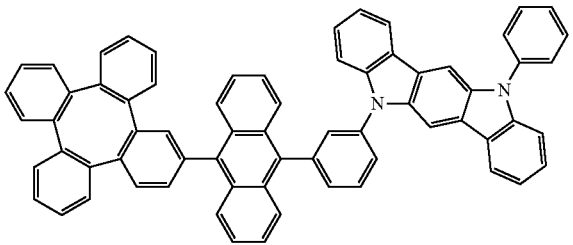

-continued
Compound 81
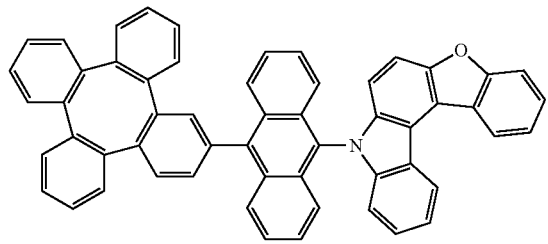
Compound 82
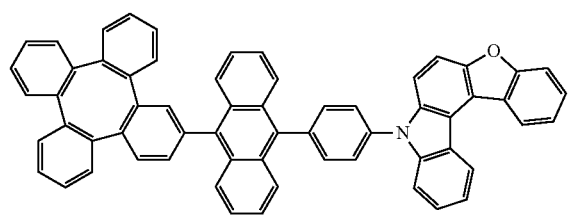
Compound 83
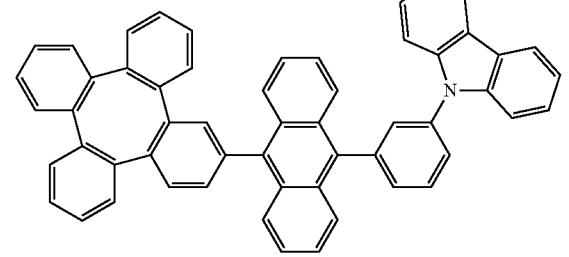
Compound 84
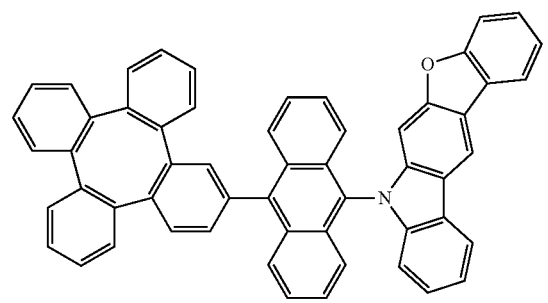
Compound 85
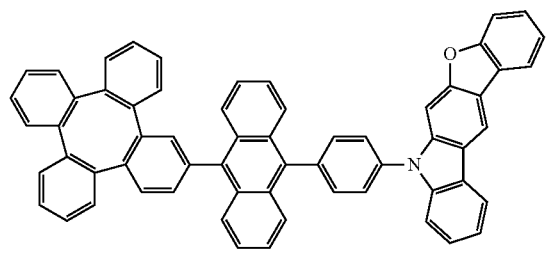
-continued
Compound 86
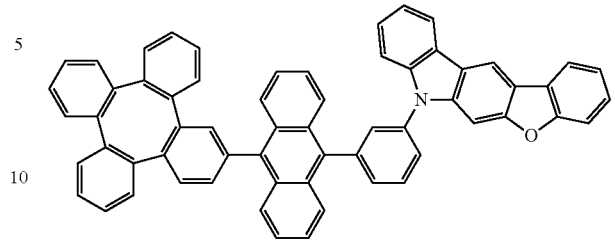
Compound 87
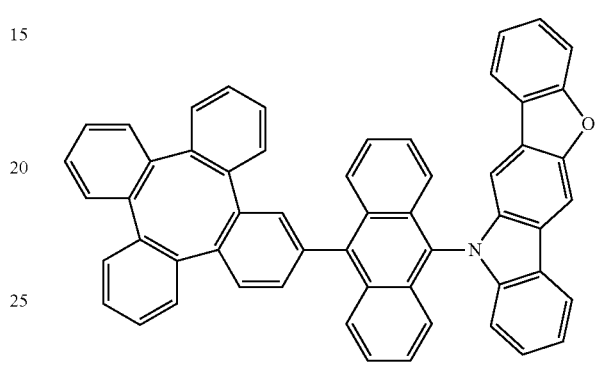
Compound 88
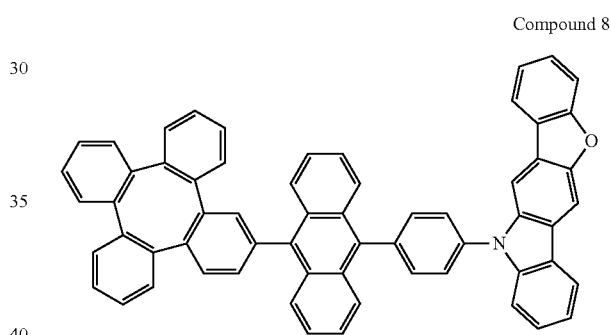
Compound 89
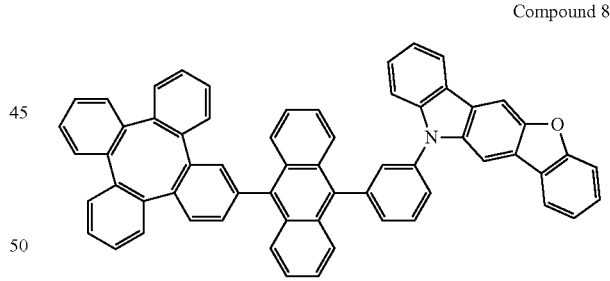
Compound 90
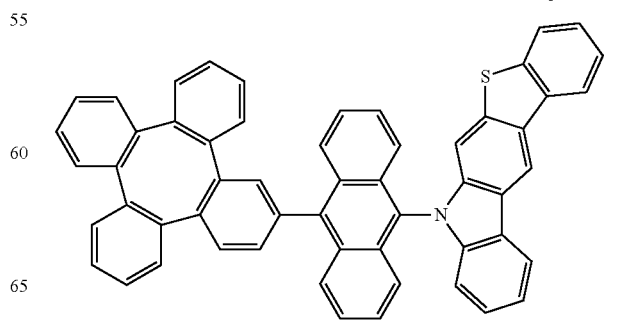

-continued

Compound 91
Compound 92
Compound 93
Compound 94
Compound 95
Compound 96
Compound 97
Compound 98
Compound 99
Compound 100

Compound 101
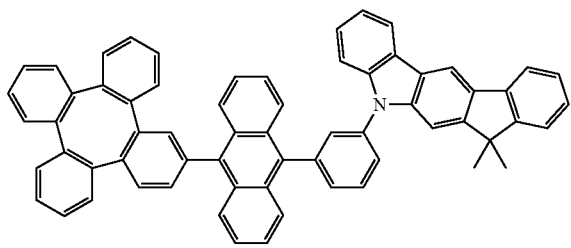
Compound 102
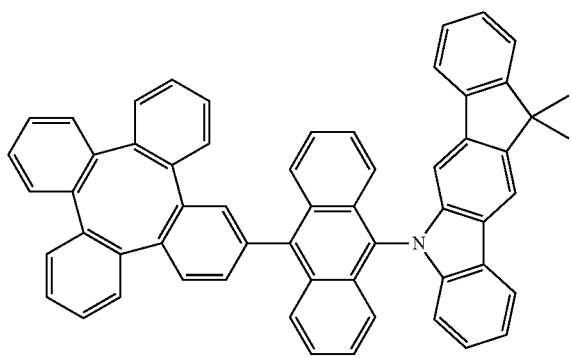
Compound 103
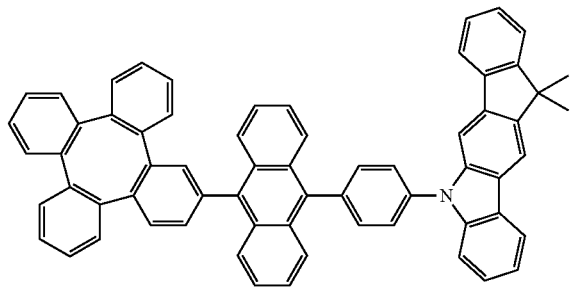
Compound 104
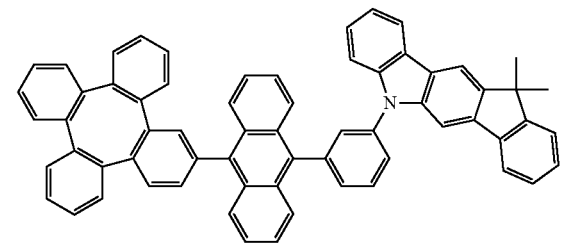
Compound 105
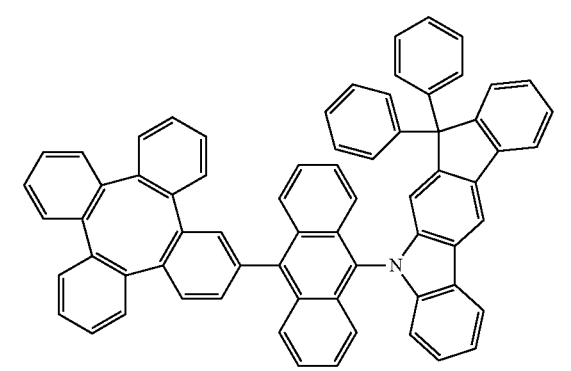
Compound 106
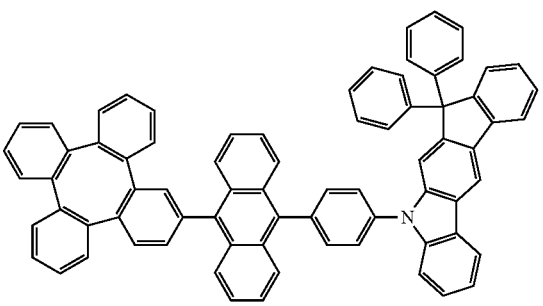
Compound 107
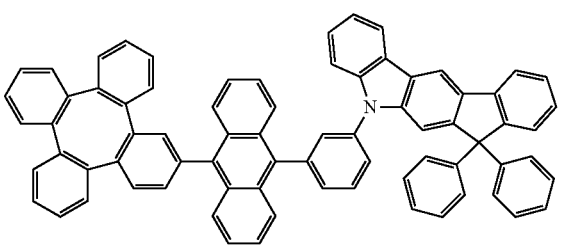
Compound 108
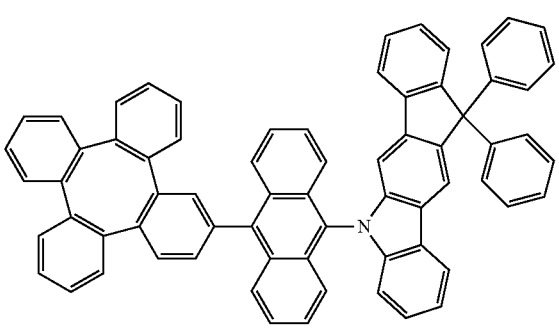
Compound 109
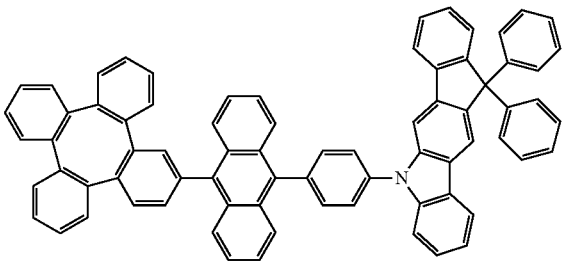
Compound 110
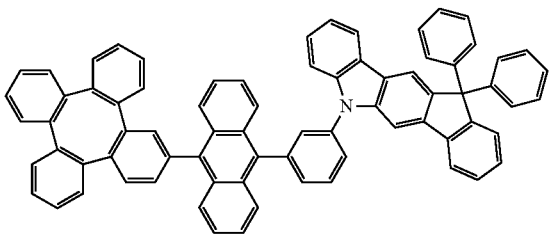

Compound 111
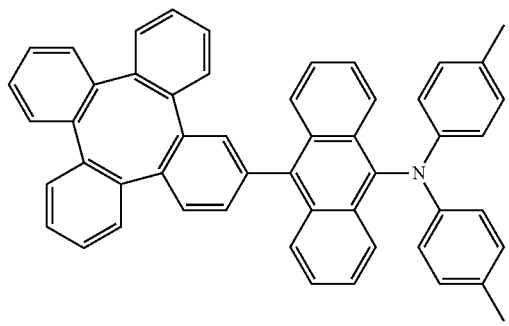
Compound 112
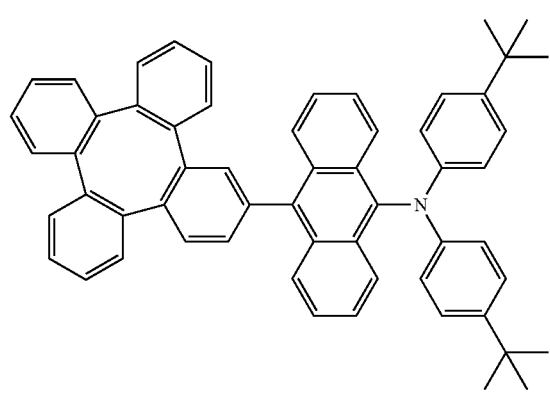
Compound 113
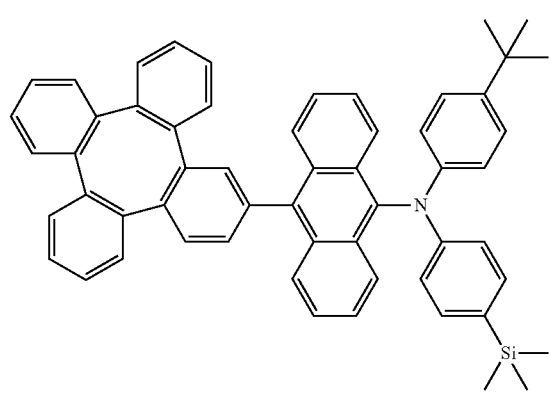
Compound 114
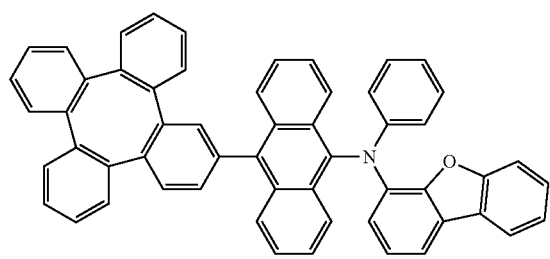
Compound 115
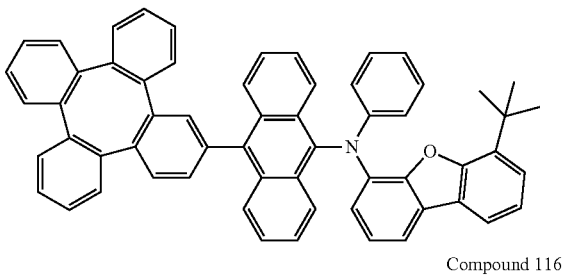
Compound 116
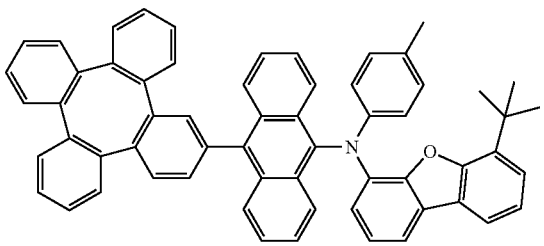
Compound 117
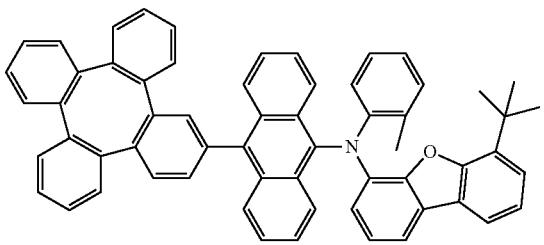
Compound 118
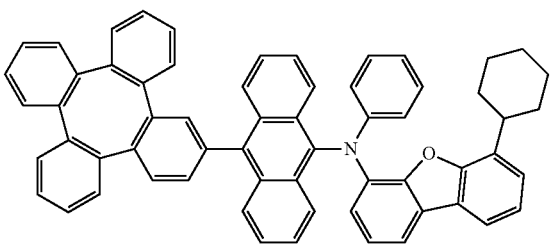
Compound 119
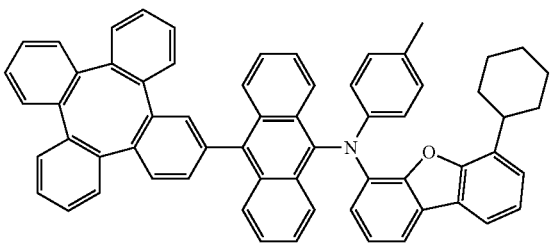
Compound 120
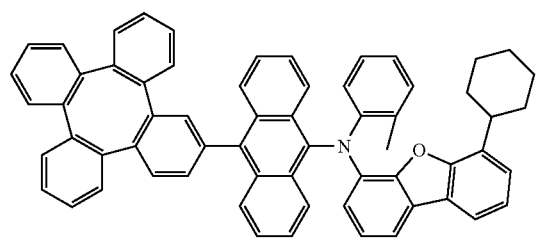

Compound 121
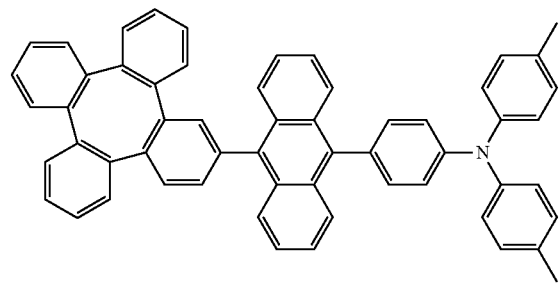
Compound 122
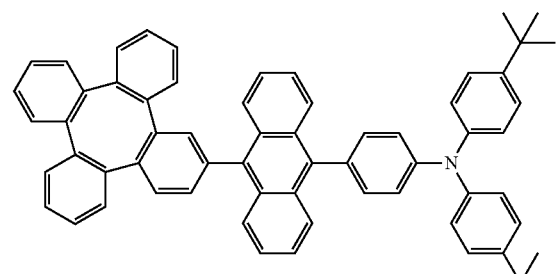
Compound 123
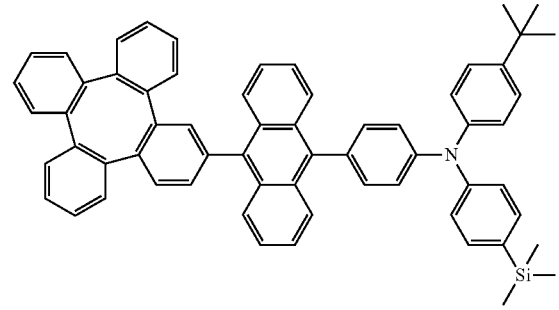
Compound 124
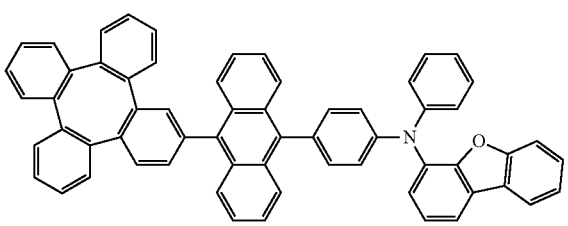
Compound 125
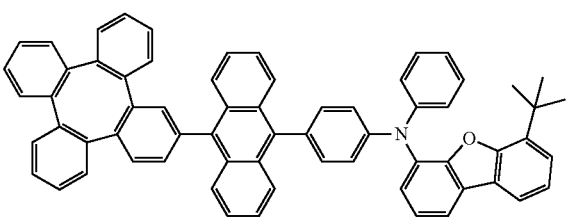
Compound 126
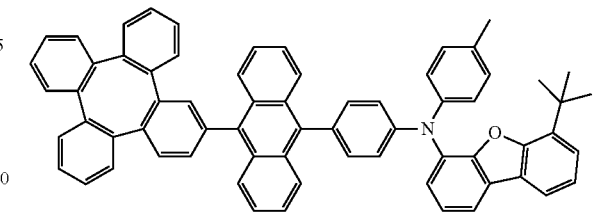
Compound 127
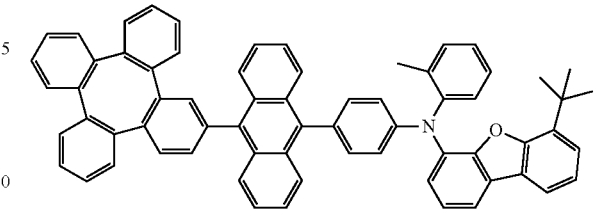
Compound 128
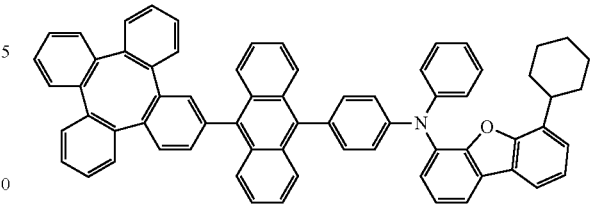
Compound 129
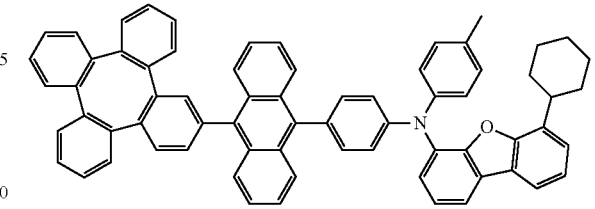
Compound 130
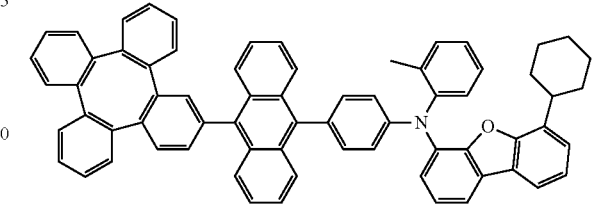
Compound 131
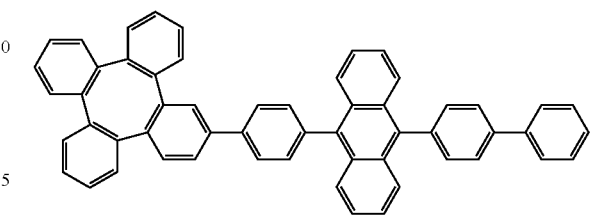

Compound 132
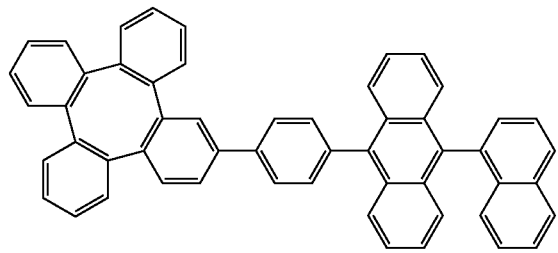
Compound 133
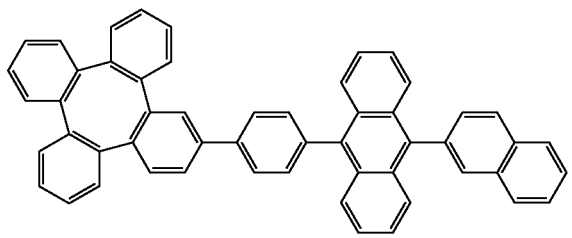
Compound 134
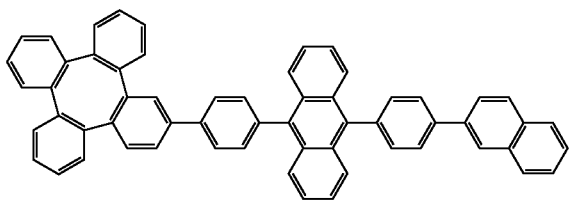
Compound 135
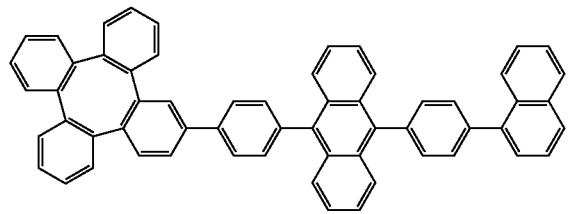
Compound 136
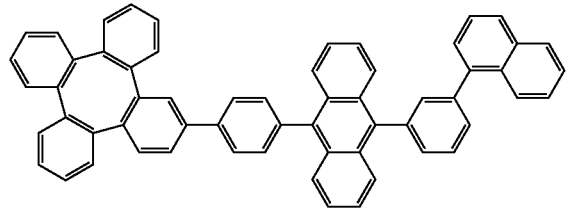
Compound 137
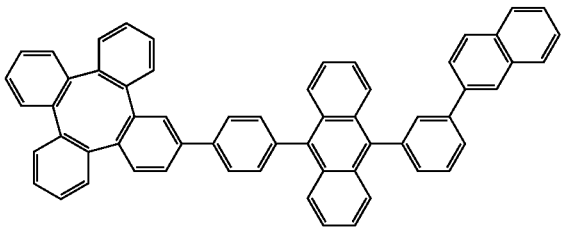
Compound 138
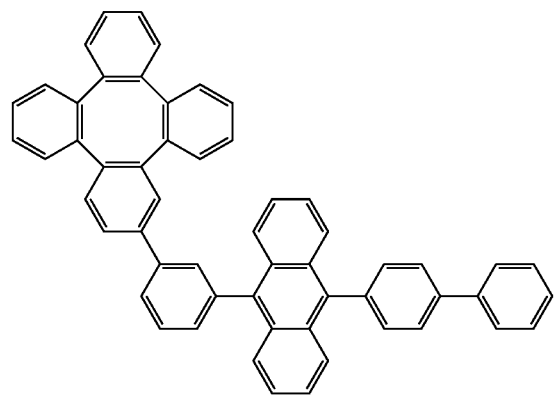
Compound 139
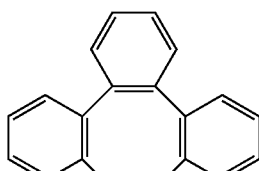
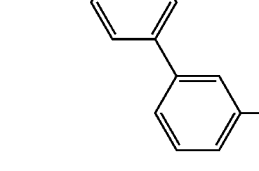
Compound 140
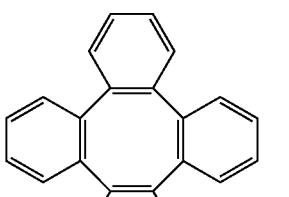
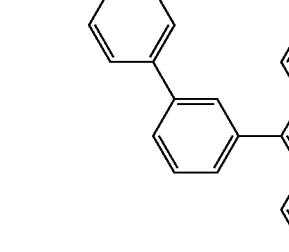

Compound 141
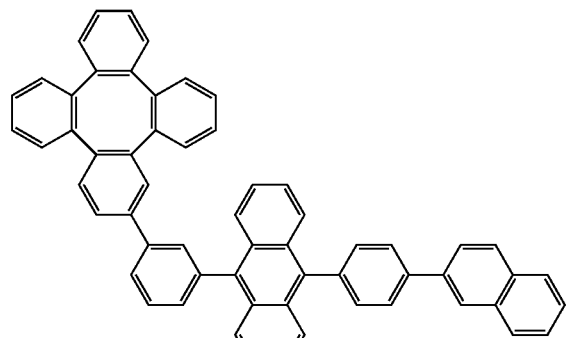
Compound 142
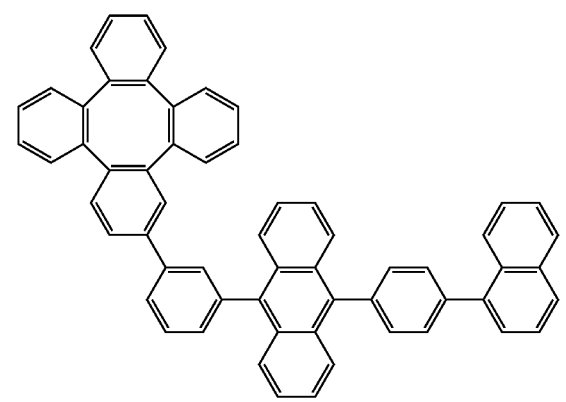
Compound 143
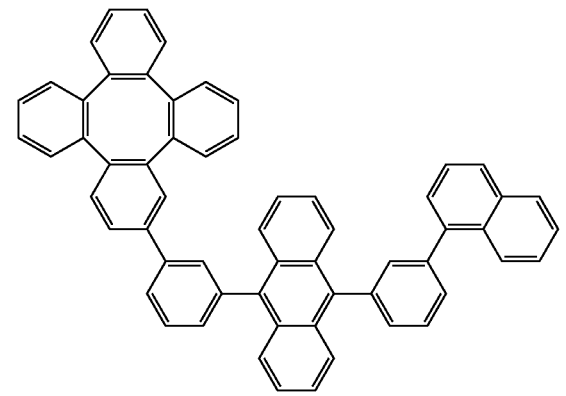
Compound 144
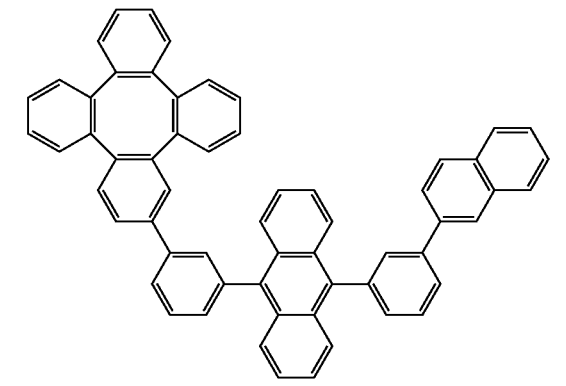
Compound 145
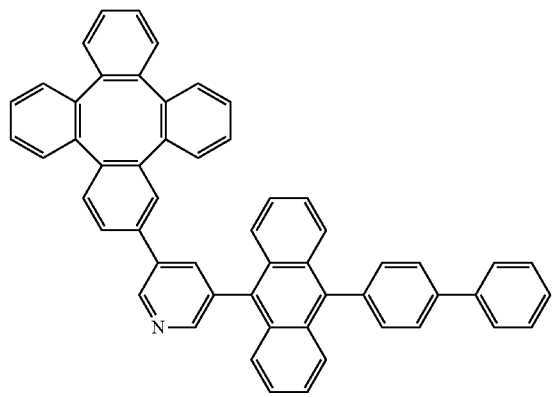
Compound 146
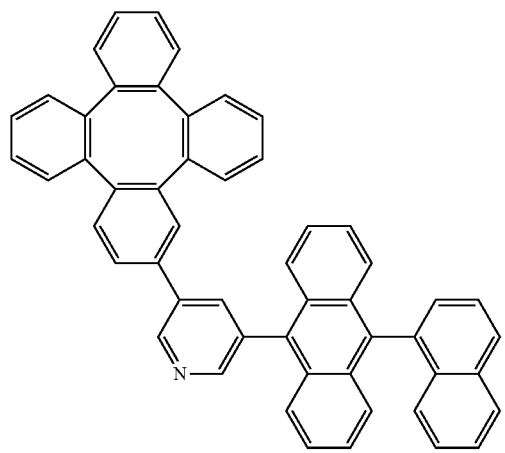
Compound 147
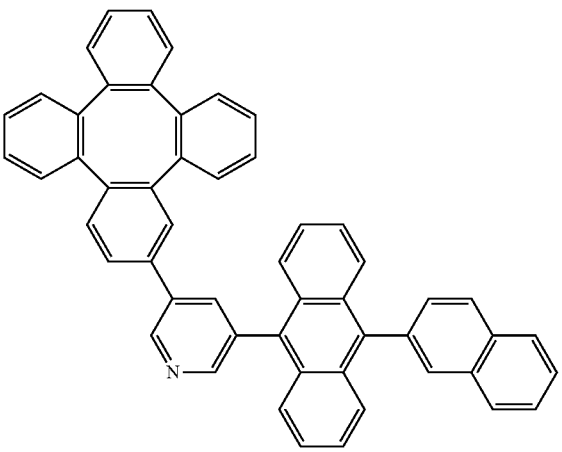

Compound 148
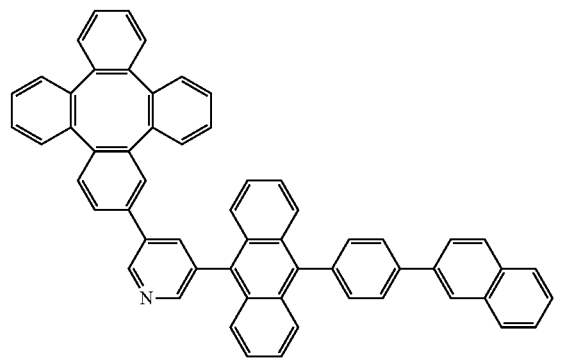
Compound 149
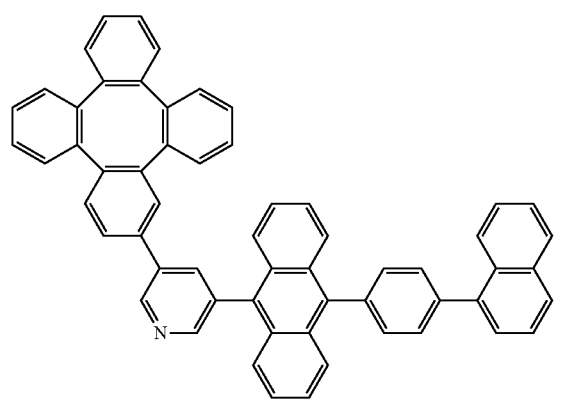
Compound 150
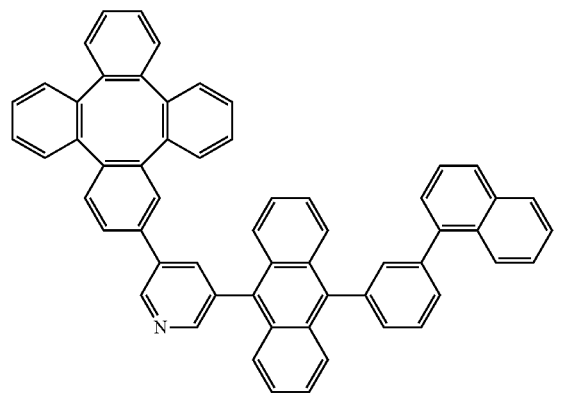
Compound 151
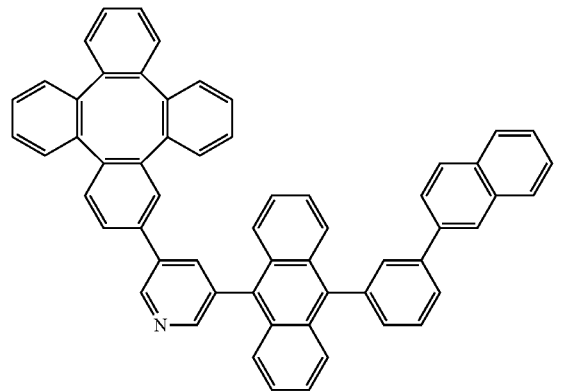
Compound 152
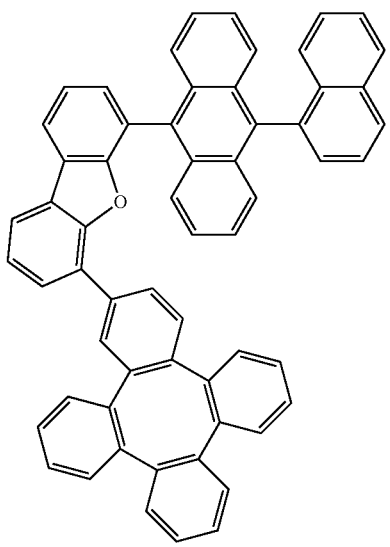
Compound 153
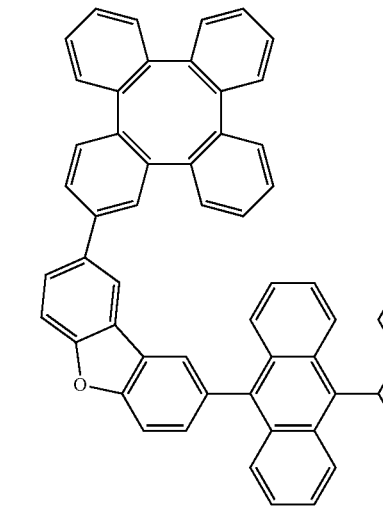
Compound 154
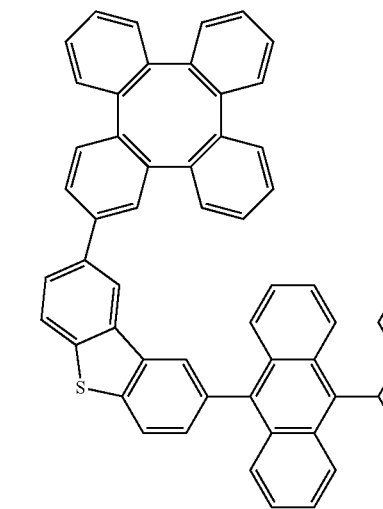

Compound 155
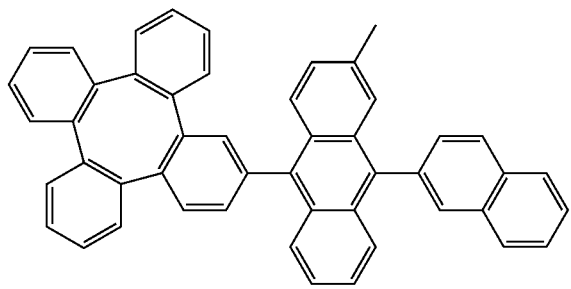
Compound 156
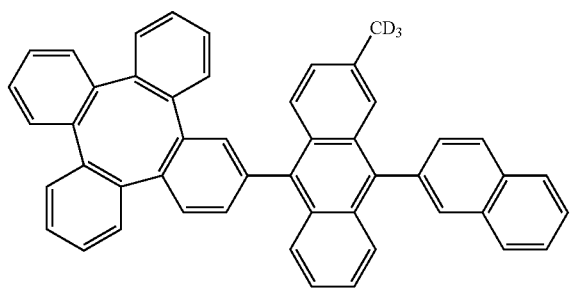
Compound 157
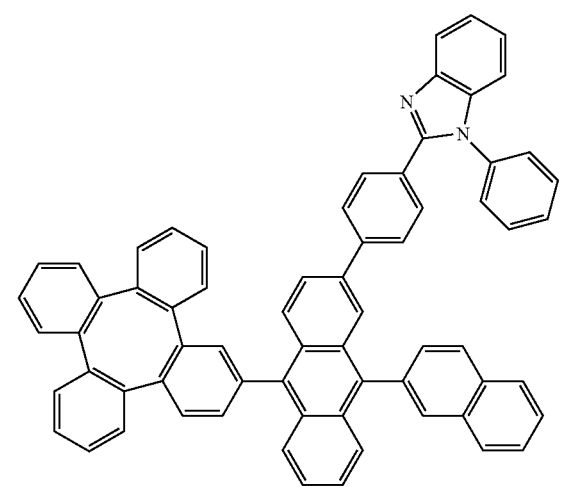
Compound 158
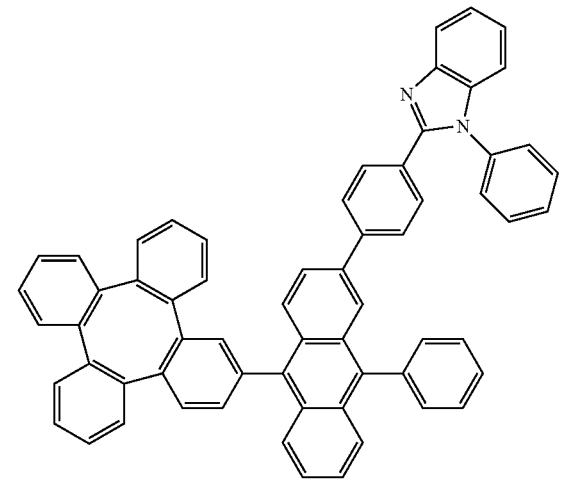
Compound 159
Compound 160
Compound 161
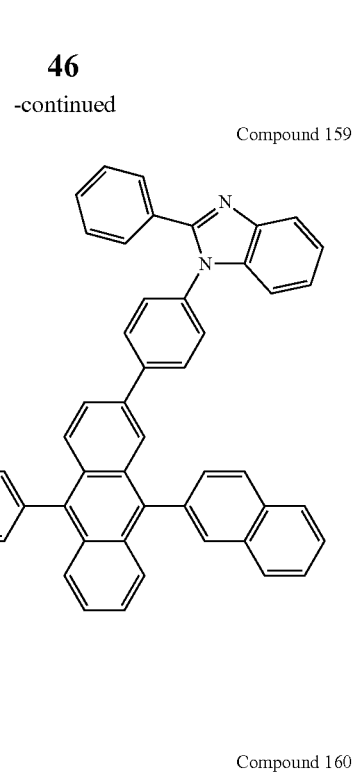

Compound 162
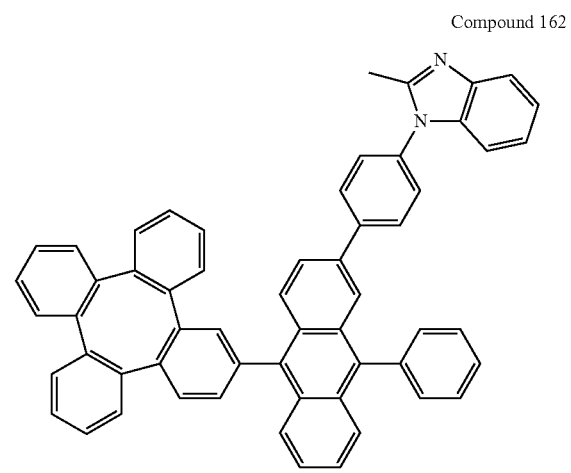
Compound 163
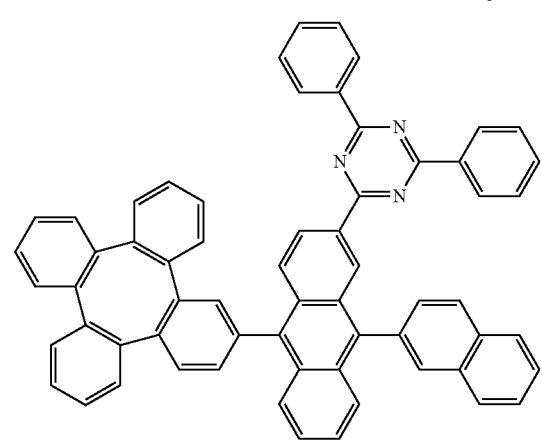
Compound 164
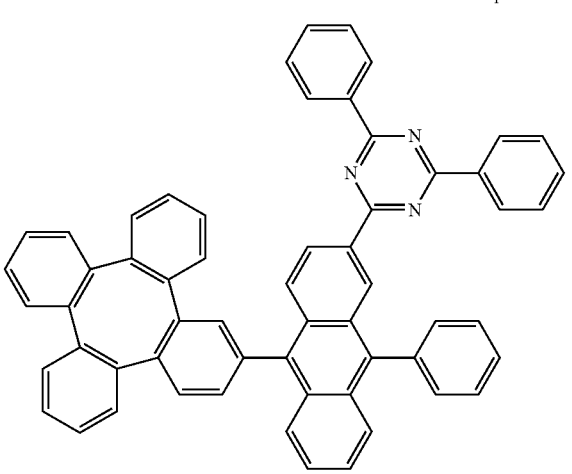
Compound 165
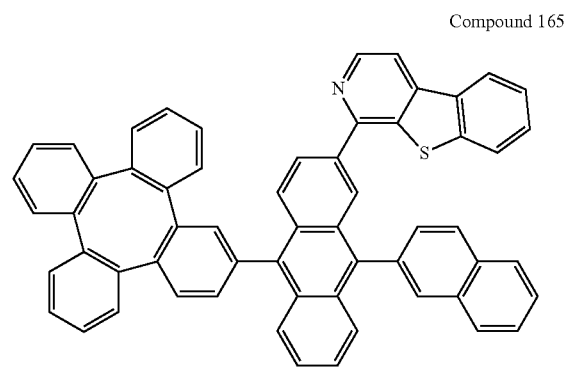
Compound 166
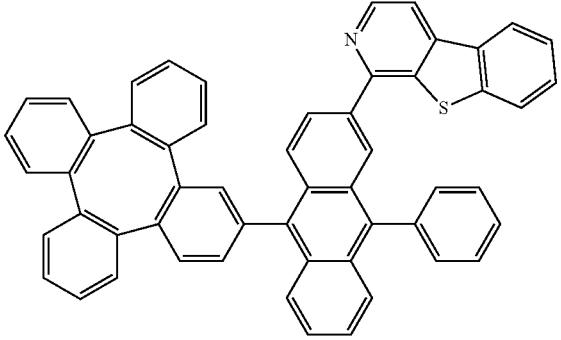
Compound 167
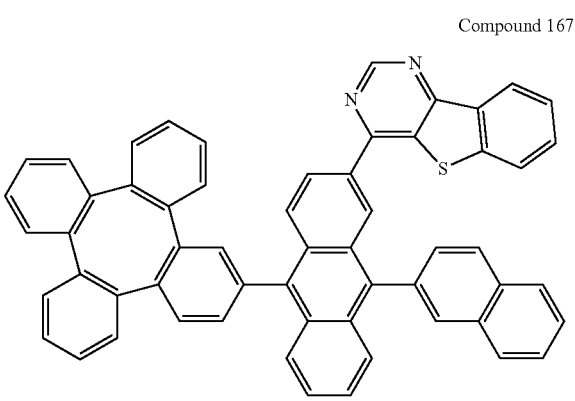
Compound 168
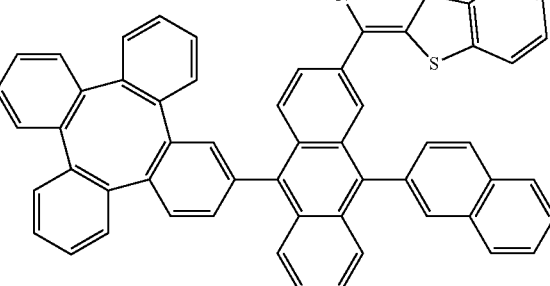

Compound 169
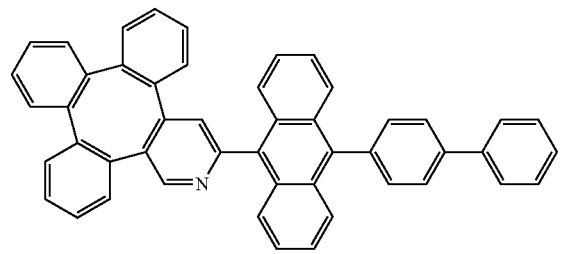
Compound 170
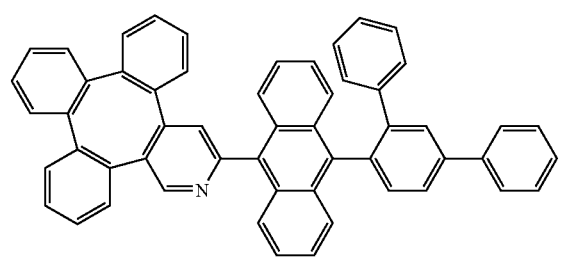
Compound 171
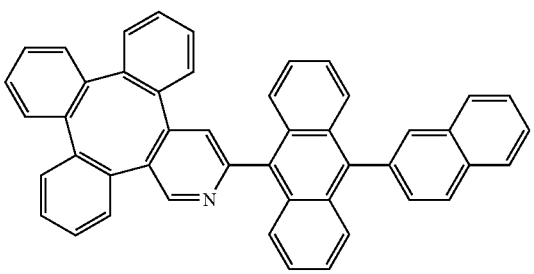
Compound 172
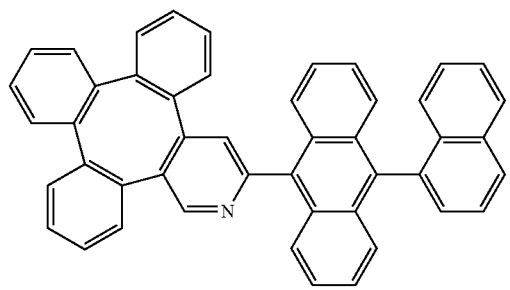
Compound 173
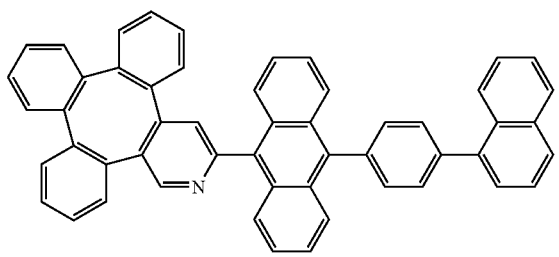
Compound 174
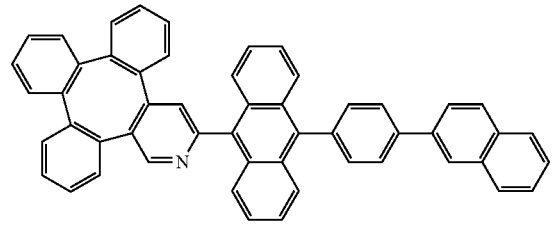
Compound 175
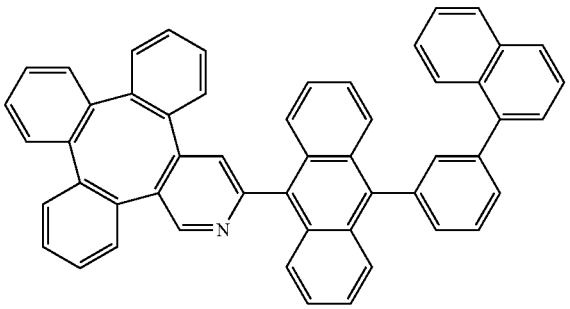
Compound 176
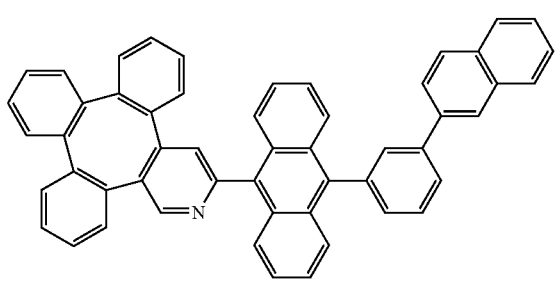

Compound 177
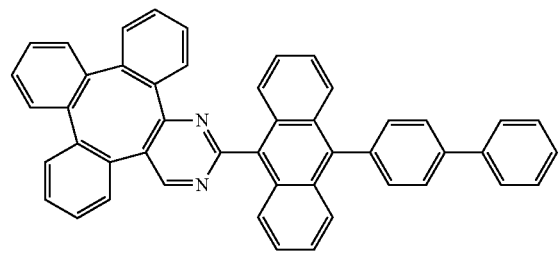
Compound 181
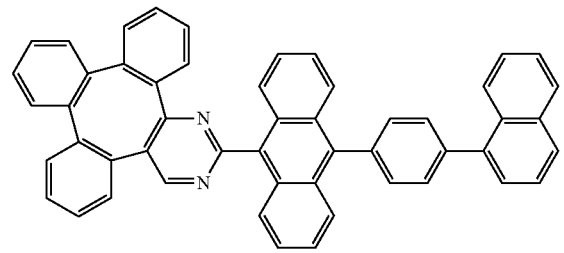
Compound 178
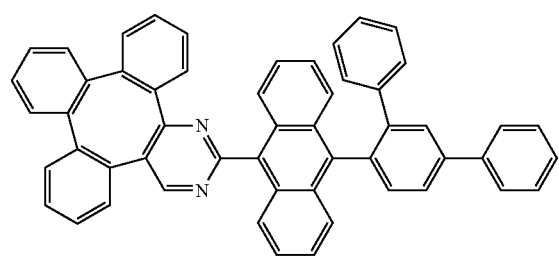
Compound 182
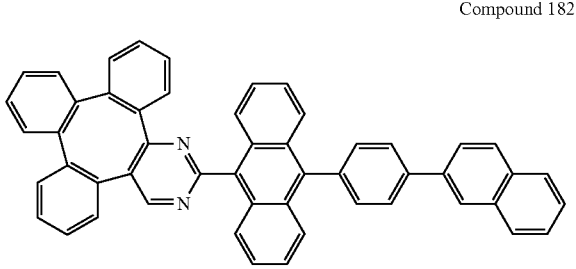
Compound 179
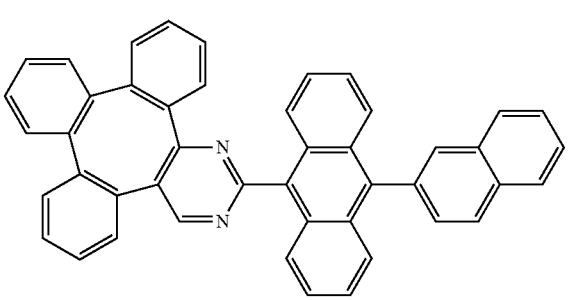
Compound 183
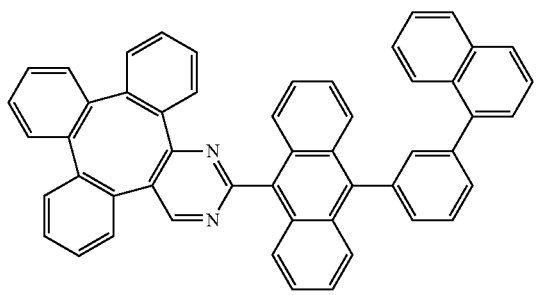
Compound 180
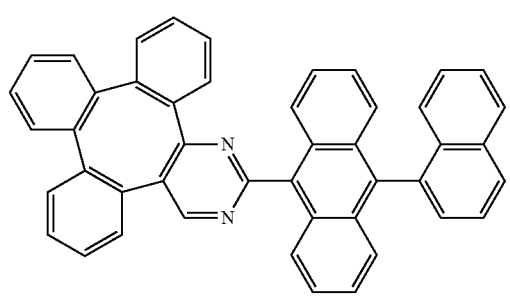
Compound 184
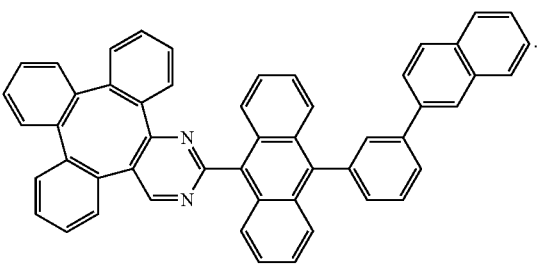

According to another embodiment, an electroluminescent device is disclosed. The electroluminescent device comprises:

an anode, a cathode, and an organic layer, disposed between the anode and the cathode, comprising a compound according to formula 1:

Formula 1

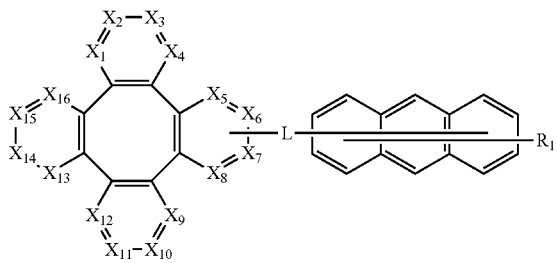

Wherein $X_1$ to $X_{16}$ are each independently selected for the group consisting of C, CR, and N;

L is selected from the group consisting of a single bond, a substituted or unsubstituted aryl group having 6 to 30 carbon atoms, a substituted or unsubstituted heteroaryl group having 4 to 30 carbon atoms, a substituted or unsubstituted alkylsilyl group having 3 to 20 carbon atoms, a substituted or unsubstituted arylsilyl group having 6 to 20 carbon atoms;

$R_1$ represents mono, multi substitution or no substitution;

R and $R_1$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

In one embodiment, wherein the organic layer is a charge transporting layer.

In one embodiment, wherein the organic layer is a light-emitting layer and the compound is a host.

In one embodiment, wherein the organic layer is a light-emitting layer and the compound is an emitter.

In one embodiment, wherein the organic layer further comprises a fluorescent emitter.

According to yet another embodiment, a formulation comprising a compound according to formula 1 is also disclosed. The specific structure of the compound is described in any of the above embodiments.

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, emissive dopants disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

Synthesis Example

The method for preparing the compounds of the present invention is not limited. The following compound is exemplified as a typical but non-limiting example, and its synthesis route and preparation method are as follows:

Synthesis Example 1: Synthesis of Compound 11

Step 1

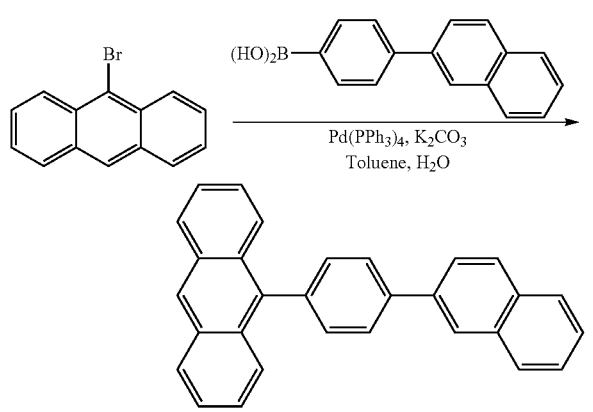

9-bromoanthracene (20.0 g, 78.13 mmol), (4-(naphthalen-2-yl)phenyl)boronic acid (22.3 g, 93.15 mmol), potassium carbonate (21.5 g, 156.3 mmol) were added to a mixture of toluene (600 mL) and water (100 mL) to give a colorless suspension. Tetrakis(triphenylphosphine)palladium(0) (2.7 g, 3.9 mmol) was added to the reaction mixture, then the reaction mixture was degassed with nitrogen and heated to 110° C. for 24 hours. After the reaction was cooled down to room temperature, the product was extracted with dichloromethane. The organic phase was separated and collected. The solid was washed with dichloromethane and methanol to afford 9-(4-(naphthalen-2-yl)phenyl)anthracene (20.0 g, 67% yield) as a yellow solid.

Step 2

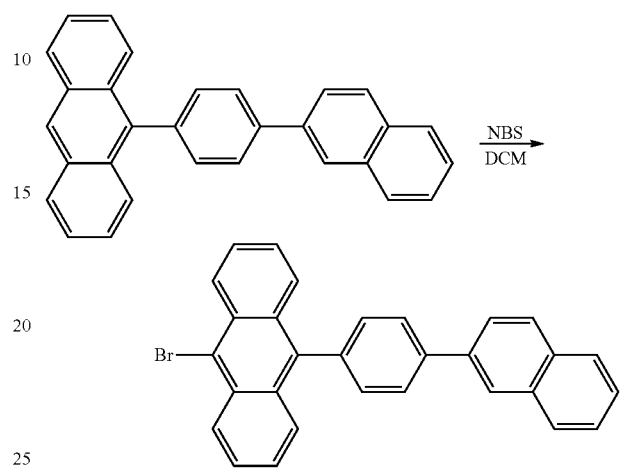

9-(4-(naphthalen-2-yl)phenyl)anthracene (12.0 g, 31.5 mmol), N-bromosuccinimide (4.0 g, 9.3 mmol) were dissolved in dichloromethane (500 mL), then the reaction mixture was degassed with nitrogen and heated to 35° C. for 12 hours. The mixture was extracted with dichloromethane and washed with water. The organic phase was separated and collected. The solid was washed with dichloromethane and methanol to afford 9-bromo-10-(4-(naphthalen-2-yl)phenyl)anthracene (12.0 g, 90% yield) as a yellow solid.

Step 3

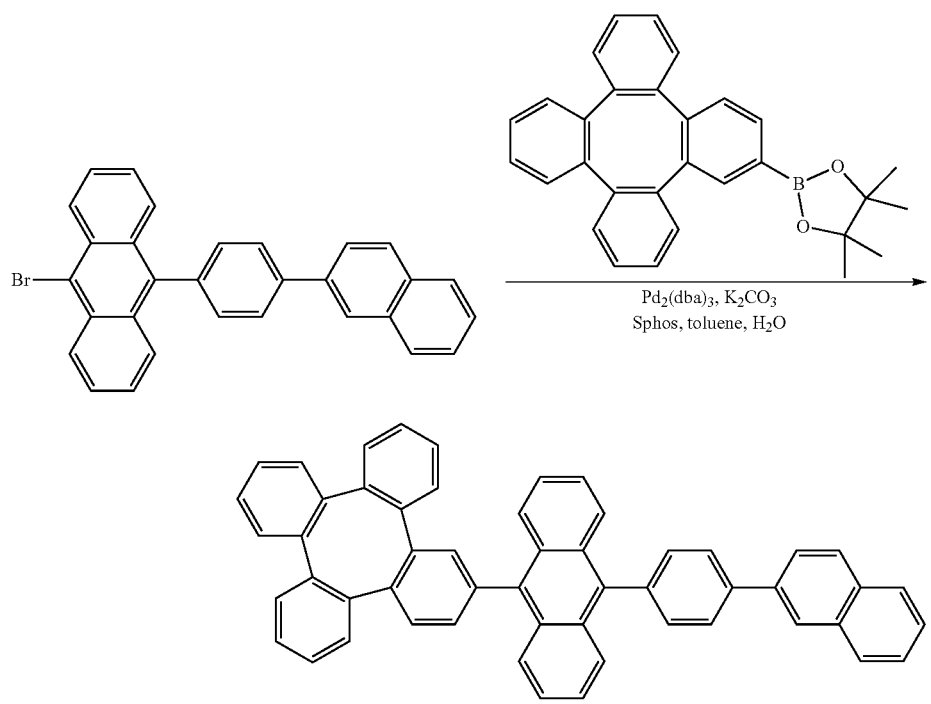

9-bromo-10-(4-(naphthalen-2-yl)phenyl)anthracene (4.7 g, 10.2 mmol), 4,4,5,5-tetramethyl-2-(tetraphenylen-2-yl)-1,3,2-dioxaborolane (3.8 g, 9.3 mmol), tris(dibenzylideneacetone)dipalladium(0) (0.47 g, 0.5 mmol), 2-dicyclohexylphosphino-2',6'-dimethoxybiphenyl (0.42 g, 1.0 mmol), potassium carbonate (2.5 g, 18.6 mmol) were added to toluene (100 mL) and water (20 mL) to give a colorless suspension, then the reaction mixture was degassed with nitrogen and heated to 110° C. for 16 hours. After the reaction was cooled down to room temperature, the solvent was removed in vacuo and extracted with dichloromethane. The organic phase was separated and collected. The residue was purified by flash column chromatography using 10%-20% of dichloromethane in hexane to afford Compound 11 (2.3 g, 33% yield) as a white solid. The product was confirmed as the target product, having a molecular weight of 683.

Synthesis Example 2: Synthesis of Compound 13

Step 1

Step 2

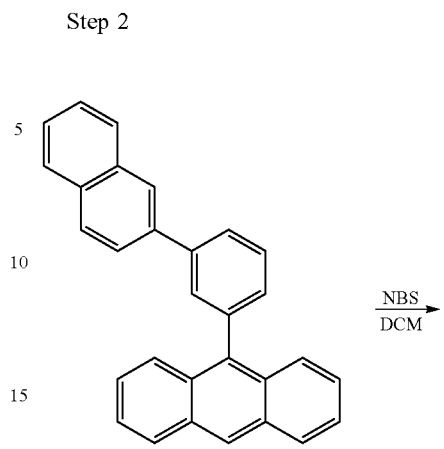

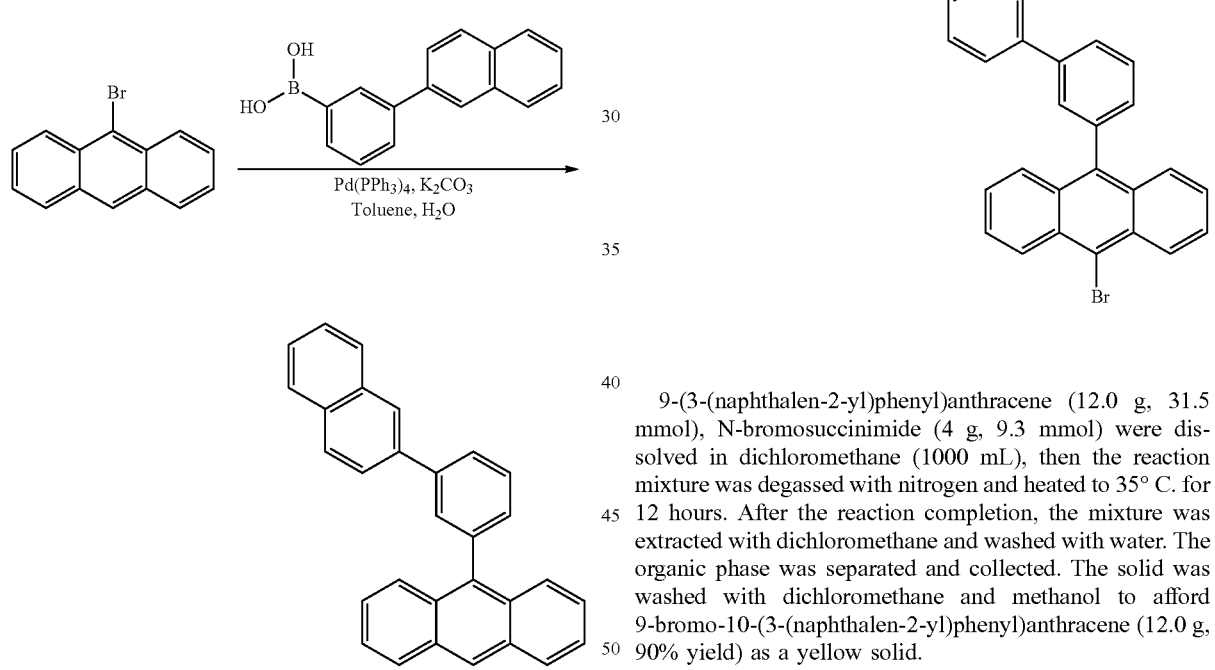

9-bromoanthracene (20 g, 78.13 mmol), (3-(naphthalen-2-yl)phenyl)boronic acid (22.3 g, 93.2 mmol), potassium carbonate (21.5 g, 156.3 mmol) were added to a mixture of toluene (600 mL) and water (100 mL) to give a colorless suspension. tetrakis(triphenylphosphine)palladium(0) (2.7 g, 3.9 mmol) was added to the reaction mixture, then the reaction mixture was degassed with nitrogen and heated to 110° C. for 24 hours. After the reaction was cooled down to room temperature, the product was extracted with dichloromethane. The organic phase was separated and collected. The solid was washed with dichloromethane and methanol to afford 9-(3-(naphthalen-2-yl)phenyl)anthracene (18.0 g, 60% yield) as a yellow solid.

9-(3-(naphthalen-2-yl)phenyl)anthracene (12.0 g, 31.5 mmol), N-bromosuccinimide (4 g, 9.3 mmol) were dissolved in dichloromethane (1000 mL), then the reaction mixture was degassed with nitrogen and heated to 35° C. for 12 hours. After the reaction completion, the mixture was extracted with dichloromethane and washed with water. The organic phase was separated and collected. The solid was washed with dichloromethane and methanol to afford 9-bromo-10-(3-(naphthalen-2-yl)phenyl)anthracene (12.0 g, 90% yield) as a yellow solid.

Step 3

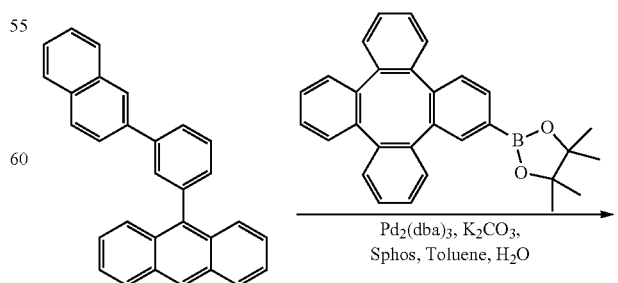

-continued

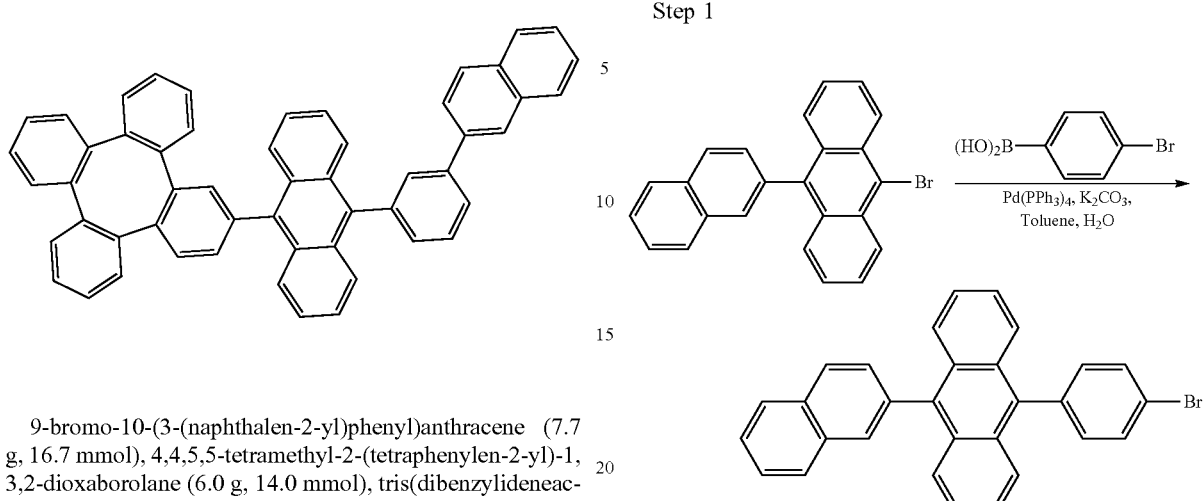

9-bromo-10-(3-(naphthalen-2-yl)phenyl)anthracene (7.7 g, 16.7 mmol), 4,4,5,5-tetramethyl-2-(tetraphenylen-2-yl)-1,3,2-dioxaborolane (6.0 g, 14.0 mmol), tris(dibenzylideneacetone)dipalladium(0) (0.64 g, 0.69 mmol), 2-dicyclohexylphosphino-2',6'-dimethoxybiphenyl (0.58 g, 1.39 mmol), potassium carbonate (3.8 g, 27.83 mmol) were added to toluene (150 mL) and water (30 mL) to give a colorless suspension, then the reaction mixture was degassed with nitrogen and heated to 110° C. for 16 hours. After the reaction was cooled down to room temperature, the solvent was removed in vacuo and extracted with DCM. The organic phase was separated and collected. The residue was purified by flash column chromatography using 10%-20% of dichloromethane in hexane to afford Compound 13 (2.5 g, 22% yield) as a white solid. The product was confirmed as the target product, having a molecular weight of 683.

Synthesis Example 3: Synthesis of Compound 133

Step 1

A mixture of 9-bromo-10-(naphthalen-2-yl)anthracene (20.0 g, 52.2 mmol), (4-bromophenyl)boronic acid (10.5 g, 52.2 mmol), Pd(PPh$_3$)$_4$ (3.0 g, 2.6 mmol), and K$_2$CO$_3$ (21.6 g, 156.54 mmol) in toluene (300 mL) and water (50 mL) was refluxed overnight under N2 atmosphere. After cooling to room temperature, the solution was extracted three times with DCM. The solvent was removed in vacuo, and the crude product was purified by column chromatography on silica gel (PE/Toluene=30:1) to afford 9-(4-bromophenyl)-10-(naphthalen-2-yl)anthracene (8.6 g, yield 36%) as a light yellow solid.

Step 2

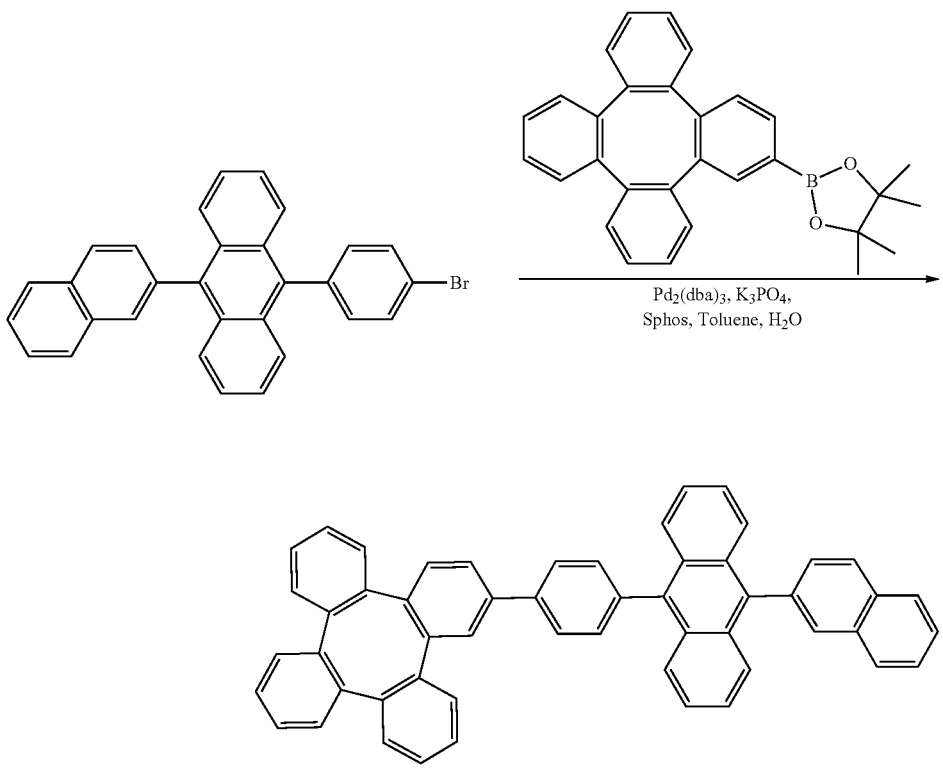

A mixture of 4,4,5,5-tetramethyl-2-(tetraphenylen-2-yl)-1,3,2-dioxaborolane (3.5 g, 8.1 mmol), 9-(4-bromophenyl)-10-(naphthalen-2-yl)anthracene (4.5 g, 9.8 mmol), $Pd_2(dba)_3$ (0.75 g, 0.81 mmol), 2-dicyclohexylphosphino-2',6'-dimethoxybiphenyl (0.33 g, 0.81 mmol), and K3PO4 (3.5 g, 16.3 mmol) in toluene (80 mL) and water (20 mL) was refluxed for 4 hours under $N_2$ atmosphere. After cooling to room temperature, the solution was extracted three times with DCM. The solvent was removed in vacuo, and the crude product was purified by column chromatography on silica gel (PE/DCM=5:1) to afford Compound 133 (4.9 g, yield 88%) as a light yellow solid. The product was confirmed as the target product, having a molecular weight of 683.

The persons skilled in the art should know that the above preparation method is only an illustrative example, and the persons skilled in the art can obtain the structure of other compounds of the present invention by modifying the above preparation method.

Device Examples

A glass substrate with 80 nm thick indium-tin-oxide (ITO) anode was first cleaned and then treated with oxygen plasma and UV ozone. After the treatments, the substrate was baked in a glovebox to remove moisture. The substrate was then mounted on a substrate holder and loaded into a vacuum chamber. The organic layers specified below were deposited in sequence by thermal vacuum deposition on the ITO anode at a rate of 0.2-2 Å/s at a vacuum level of around $10^{-8}$ torr. Compound HI was used as the hole injection layer (HIL). Compound HT was used as the hole transporting layer (HTL). Compound EB was used as the electron blocking layer (EBL). Then by co-deposition, Compound EM was doped in the inventive compound as the emitting layer (EML). Compound HB was used as the hole blocking layer (HBL). On the HBL, Compound ET and 8-hydroxyquinolinolato-lithium(Liq) were co-deposited as the electron transporting layer (ETL). Finally, 1 nm of Liq was deposited as the electron injection layer and 120 nm of Al was deposited as the cathode. The device was then transferred back to the glovebox and encapsulated with a glass lid and a moisture getter.

The detailed device layer structure and thicknesses are shown in the table below. In the layers in which more than one material were used, they were obtained by doping different compounds in the weight ratios described therein.

The structures of the materials used in the devices are shown below:

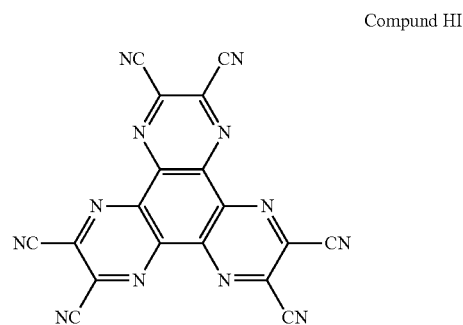

Compound HI

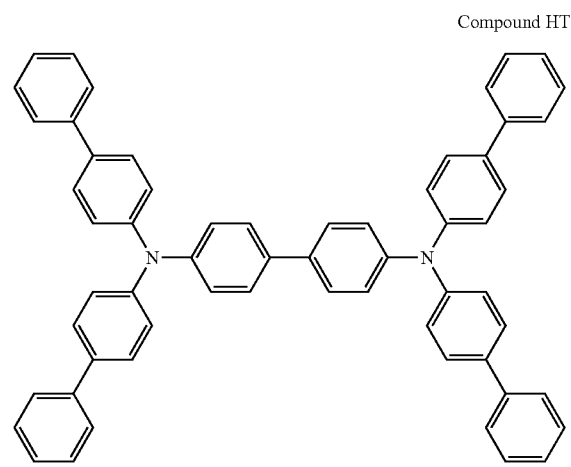

Compound HT

TABLE 1

Device structure of device examples

| Device ID | HIL | HTL | EBL | EML | HBL | ETL |
|---|---|---|---|---|---|---|
| Example 1 | Compound HI (100 Å) | Compound HT (1200 Å) | Compound EB (100 Å) | Compound 11:Compound EM (96:4) (250 Å) | Compound HB (100 Å) | Compound ET:Liq (50:50) (150 Å) |
| Example 2 | Compound HI (100 Å) | Compound HT (1200 Å) | Compound EB (100 Å) | Compound 13:Compound EM (96:4) (250 Å) | Compound HB (100 Å) | Compound ET:Liq (50:50) (150 Å) |
| Example 3 | Compound HI (100 Å) | Compound HT (1200 Å) | Compound EB (100 Å) | Compound 133:Compound EM (96:4) (250 Å) | Compound HB (100 Å) | Compound ET:Liq (50:50) (150 Å) |

Compound EB

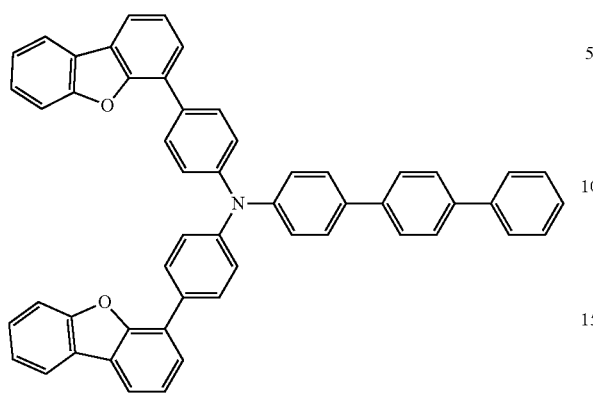

Compound EM

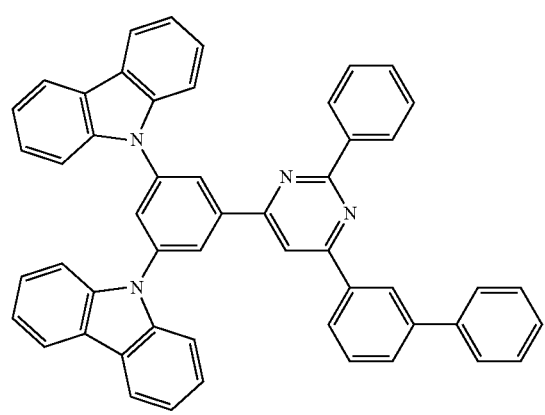

Compound HB

Compound ET

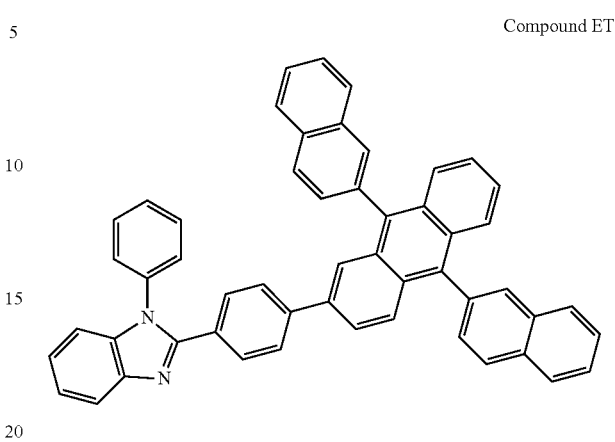

The IVL characteristics of the devices were measured. Table 2 shows the luminance efficiency (LE), λmax, full width at half maximum (FWHM), voltage (V) and CIE data at 1,000 cd/m². The sublimation temperatures (Sub T) were also recorded and shown.

TABLE 2

Device data

| Device ID | Sub T (° C.) | CIE (x, y) | λmax (nm) | FWHM (nm) | Voltage (V) | LE (cd/A) |
|---|---|---|---|---|---|---|
| Example 1 | 299 | 0.143, 0.082 | 454 | 30 | 4.62 | 4.72 |
| Example 2 | 279 | 0.142, 0.088 | 454 | 31 | 4.52 | 4.35 |
| Example 3 | 317 | 0.143, 0.083 | 453 | 30 | 4.65 | 4.59 |

Discussion:

As shown from the data in Table 2, it demonstrates that compounds of Formula 1, characterized by tetraarylene or tetraheteroarylene connected to anthracene via various modes of linkages can offer high efficiency and narrow emission in devices.

It is understood that the various embodiments described herein are by way of example only, and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:

1. A compound having formula 1:

Formula 1

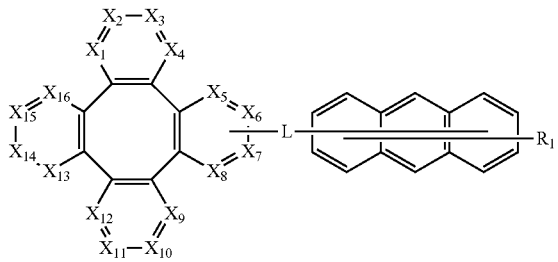

wherein
- $X_1$ to $X_{16}$ are each independently selected from the group consisting of C, CR, and N;
- L is selected from the group consisting of a single bond, a substituted or unsubstituted aryl group having 6 to 30 carbon atoms, a substituted or unsubstituted heteroaryl group having 4 to 30 carbon atoms, a substituted or unsubstituted alkylsilyl group having 3 to 20 carbon atoms, a substituted or unsubstituted arylsilyl group having 6 to 20 carbon atoms;
- $R_1$ represents mono, multi substitution or no substitution;
- R is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 12 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;
- $R_1$ is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 20 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;
- any adjacent substitution can be optionally joined to form a ring or fused structure.

2. The compound of claim 1, wherein none of $X_1$ to $X_{16}$ is N.

3. The compound of claim 1, wherein at least one of $X_1$ to $X_{16}$ is N.

4. The compound of claim 1, wherein L is selected from the group consisting of:

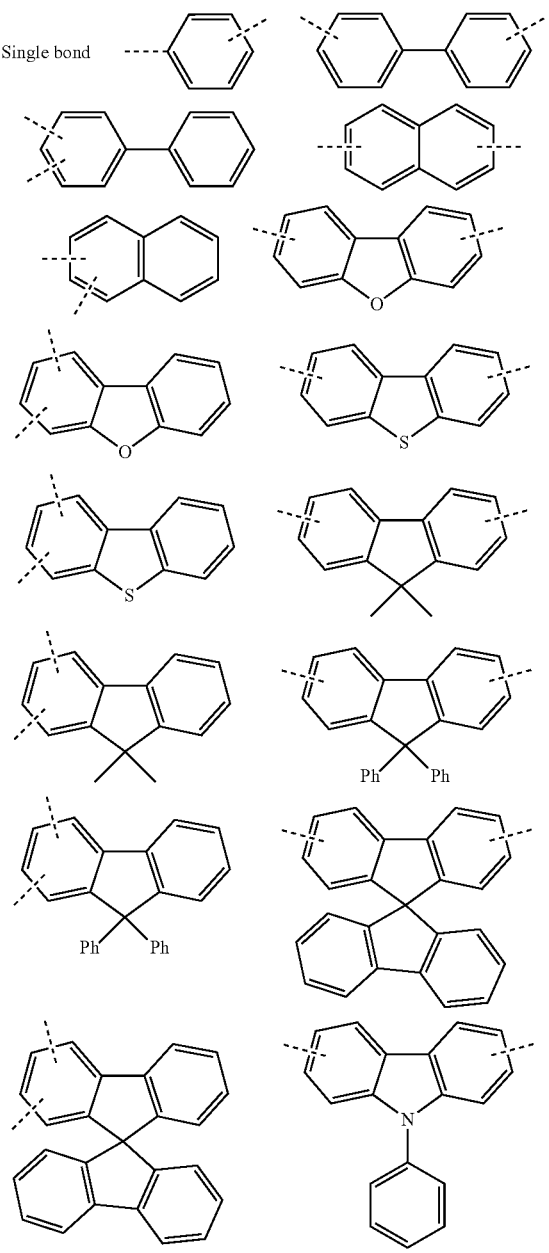

-continued

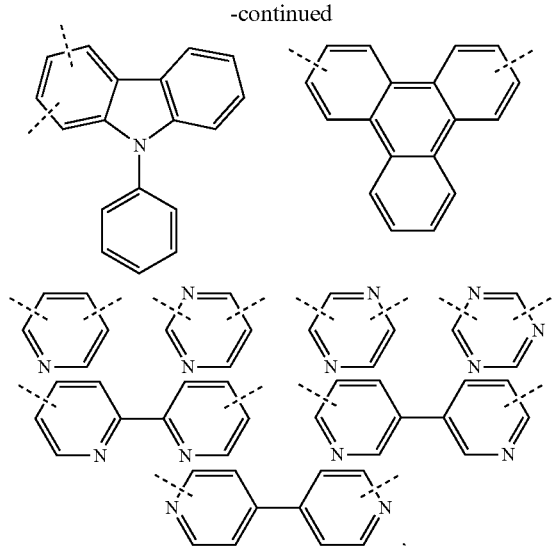

and combinations thereof.

5. The compound of claim 1, wherein R₁ is a substituted or unsubstituted aryl group having 6 to 20 carbon atoms, or a substituted or unsubstituted heteroaryl group having 6 to 30 carbon atoms.

6. The compound of claim 1, wherein R₁ is a substituted or unsubstituted aryl group comprising a fused ring system.

7. The compound of claim 1, wherein R₁ is selected from the group consisting of phenyl, biphenyl, terphenyl, pyridine, pyrimidine, triazine, dibenzofuran, dibenzothiophene, carbazole, fluorene, triphenylene, phenanthrene, phenanthroline, pyrene, and combinations thereof.

8. The compound of claim 1, wherein L is connected to the 9$^{th}$ position of anthracene and R₁ is connected to the 10$^{th}$ position of anthracene.

9. The compound of claim 1, wherein the compound is selected from the group consisting of:

Compound 1

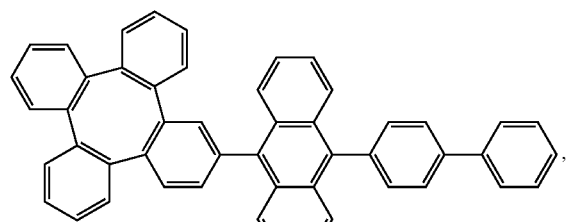

Compound 2

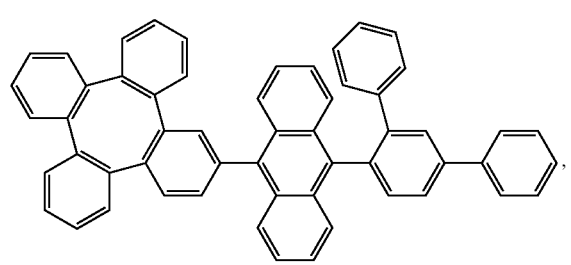

Compound 3

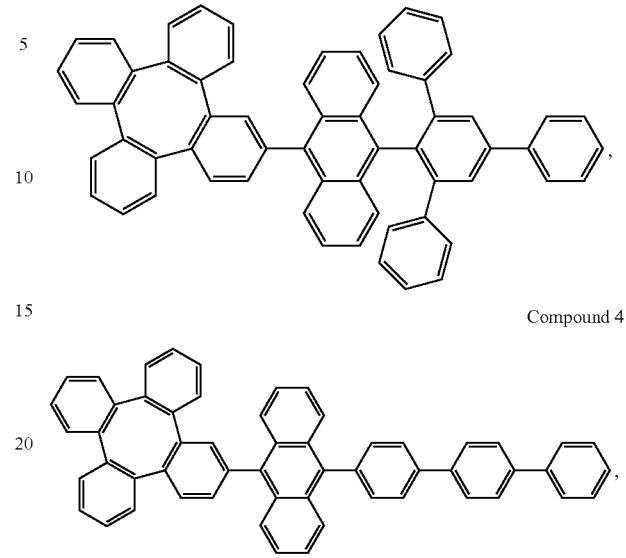

Compound 4

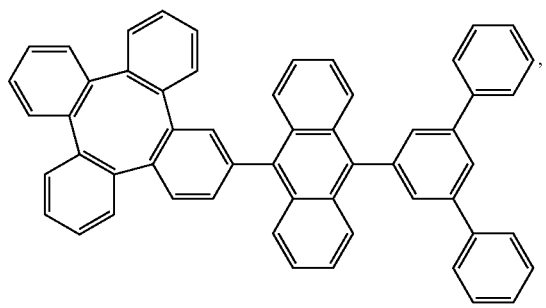

Compound 5

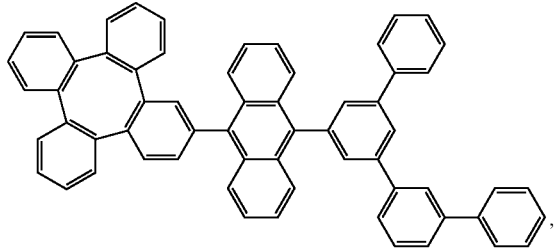

Compound 6

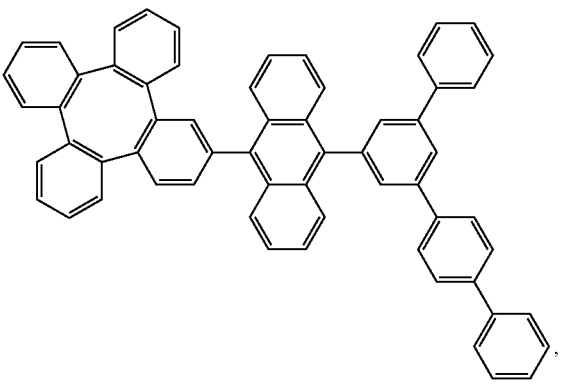

Compound 7

Compound 8
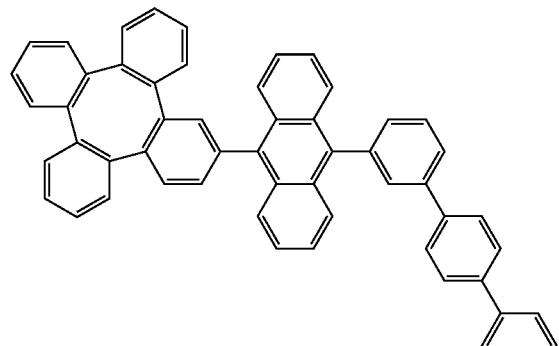
Compound 9
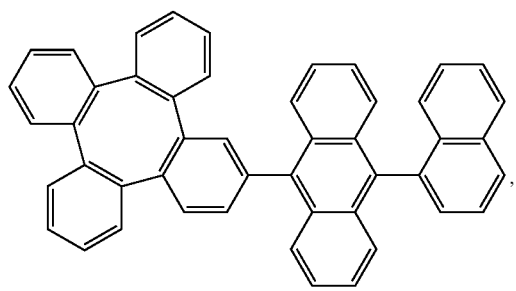
Compound 10
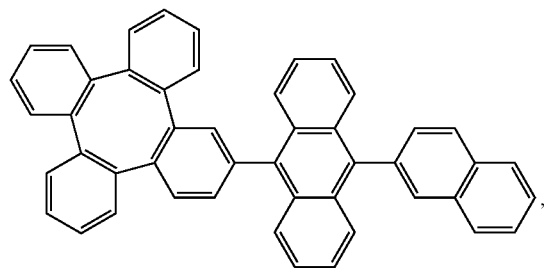
Compound 11
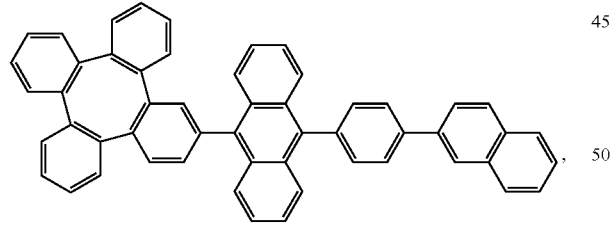
Compound 12
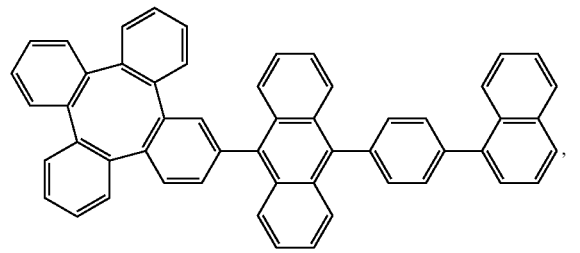
Compound 13
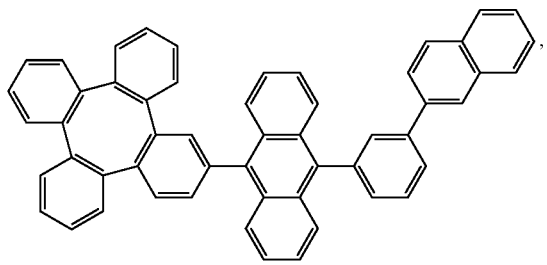
Compound 14
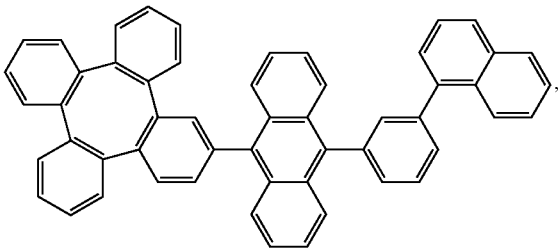
Compound 15
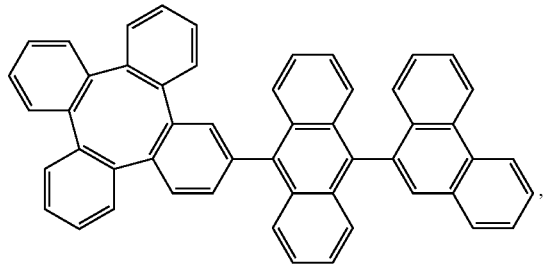
Compound 16
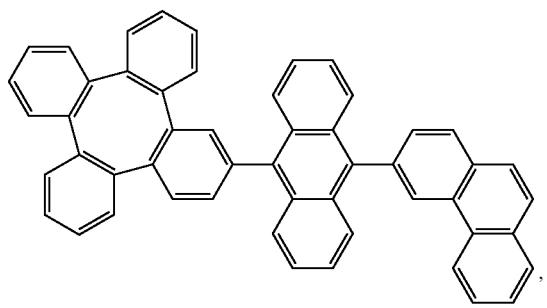
Compound 17
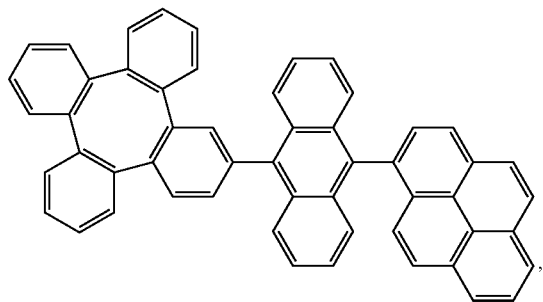

-continued
Compound 18
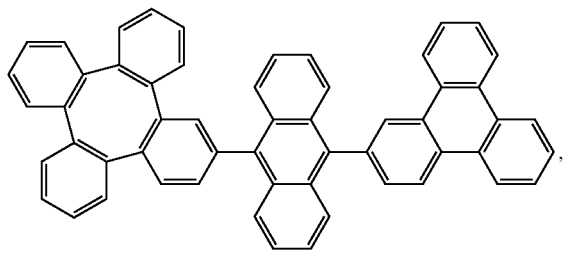
Compound 19
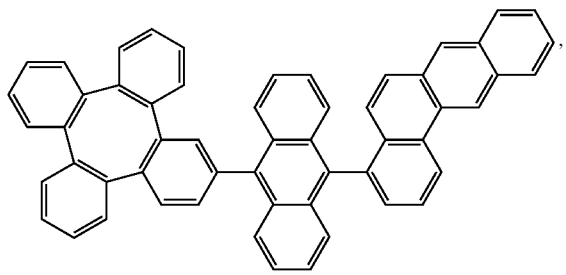
Compound 20
Compound 21
Compound 22
-continued
Compound 23
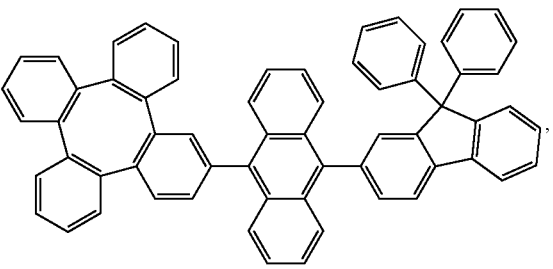
Compound 24
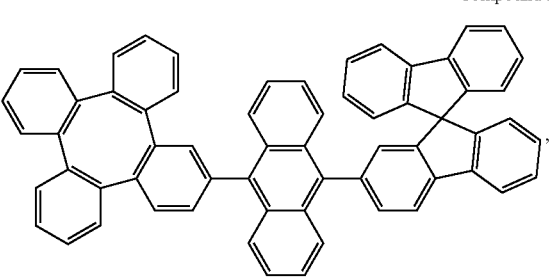
Compound 25
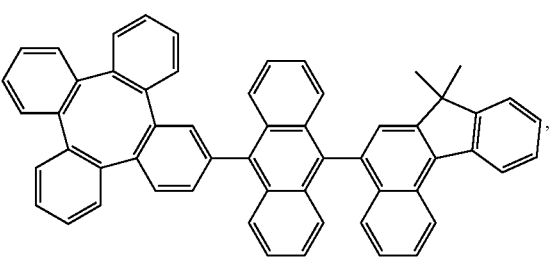
Compound 26
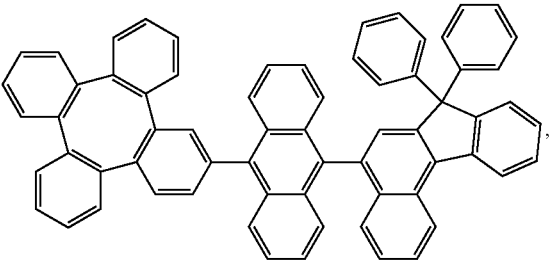
Compound 27
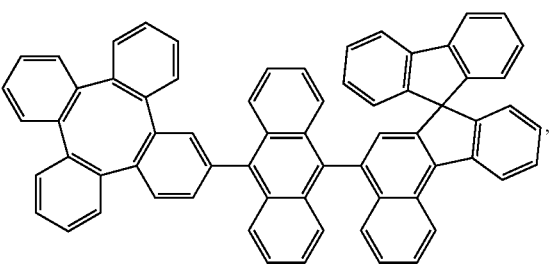

Compound 28
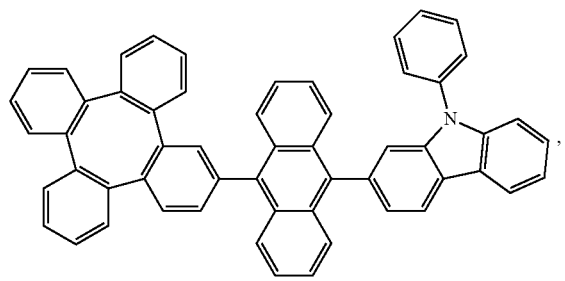
Compound 29
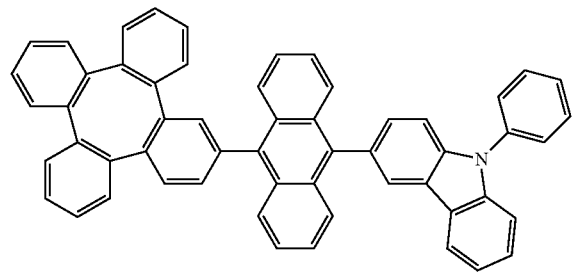
Compound 30
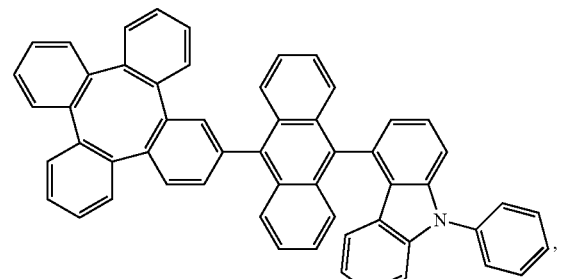
Compound 31
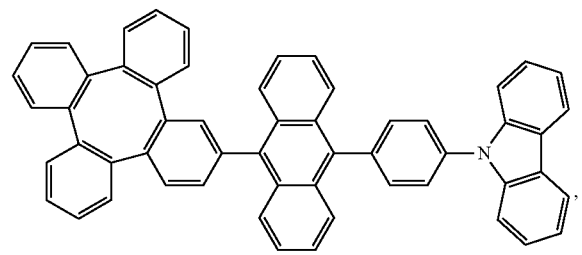
Compound 32
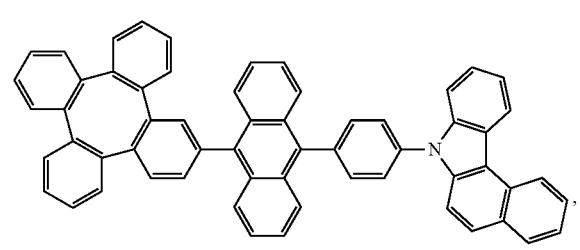
Compound 33
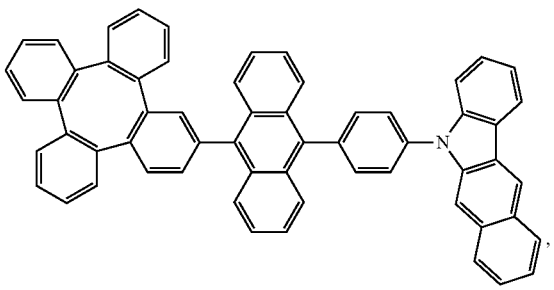
Compound 34
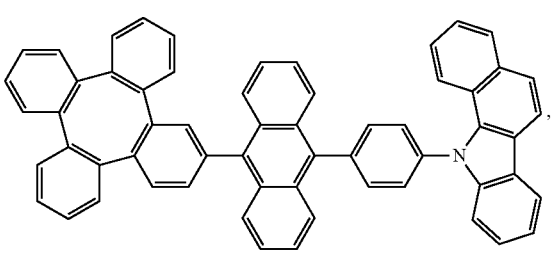
Compound 35
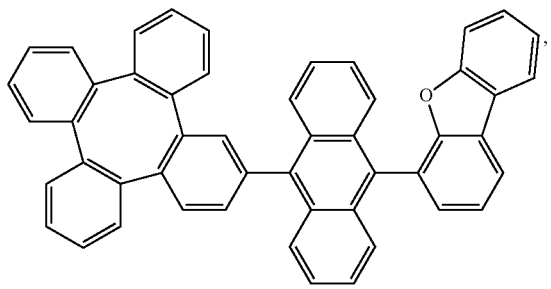
Compound 36
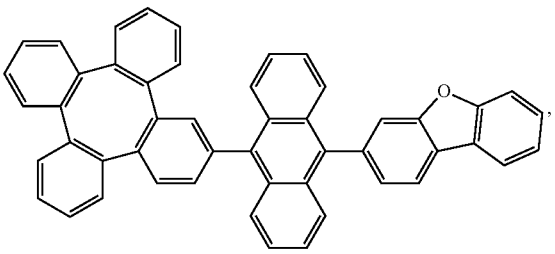
Compound 37
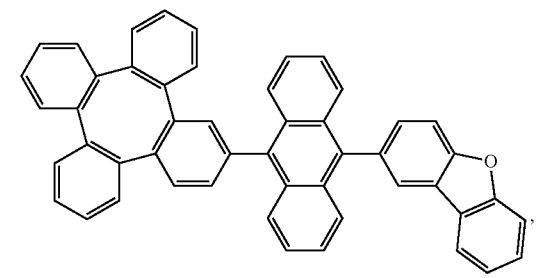

Compound 38
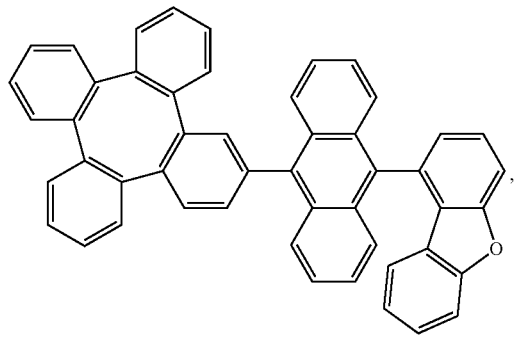
Compound 39
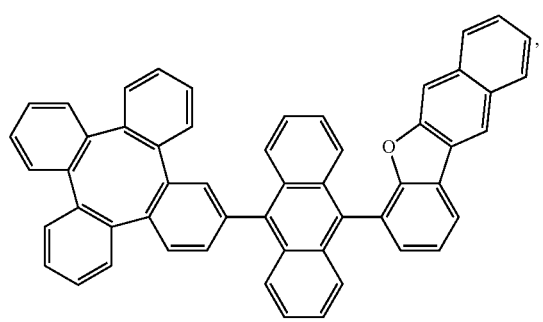
Compound 40
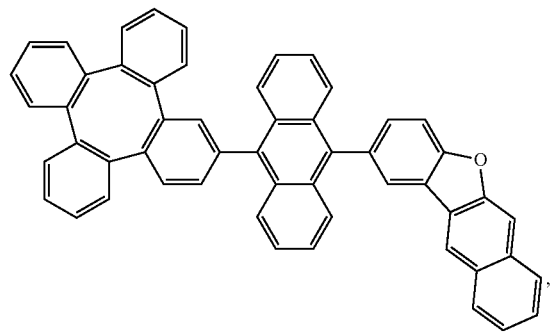
Compound 41
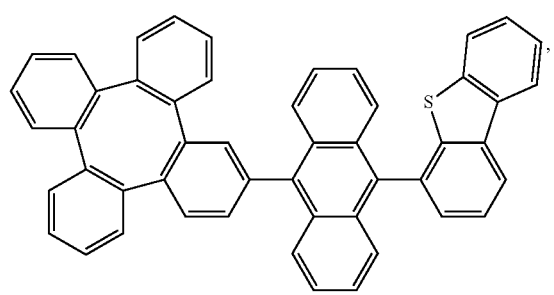
Compound 42
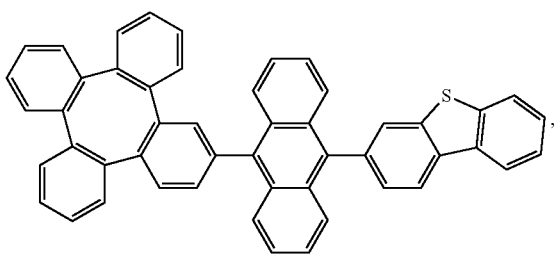
Compound 43
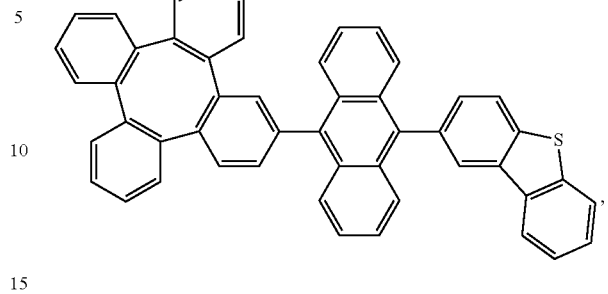
Compound 44
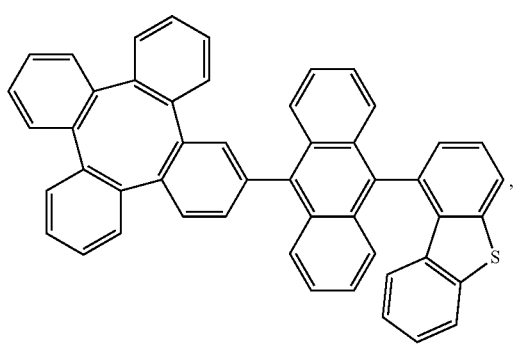
Compound 45
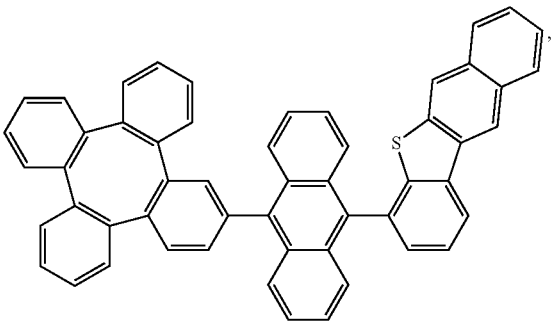
Compound 46
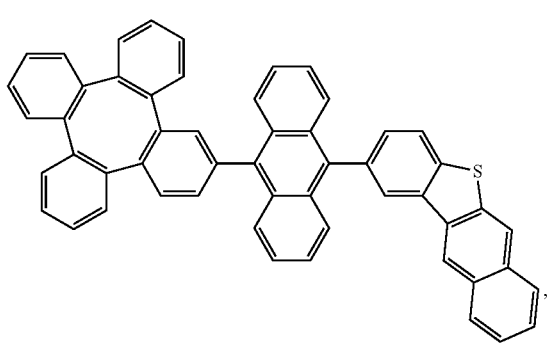

-continued
Compound 47
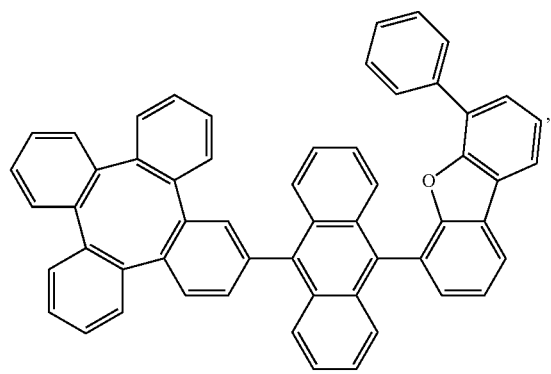
Compound 48
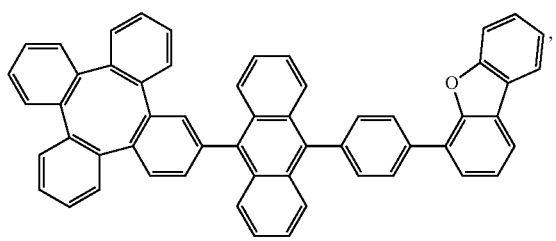
Compound 49
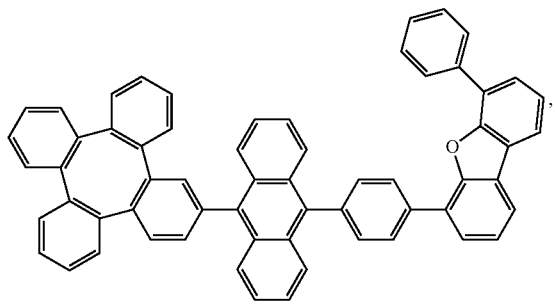
Compound 50
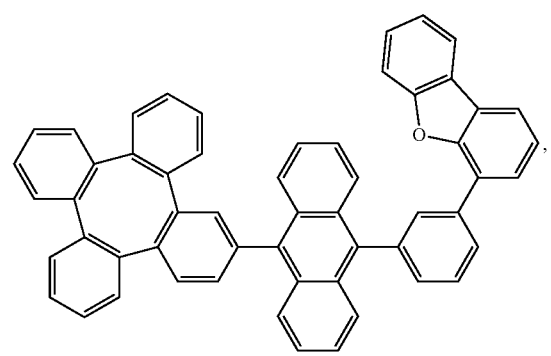
Compound 51
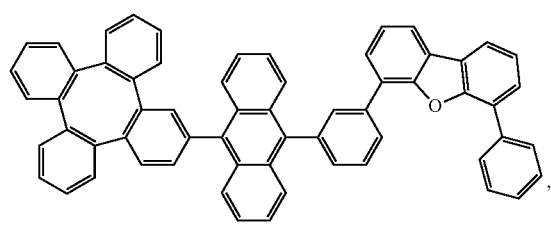
-continued
Compound 52
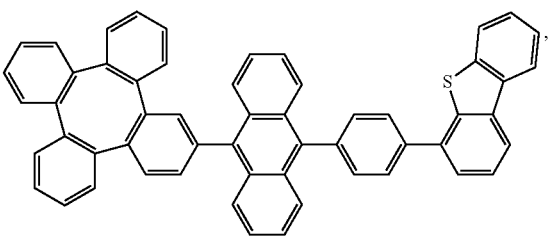
Compound 53
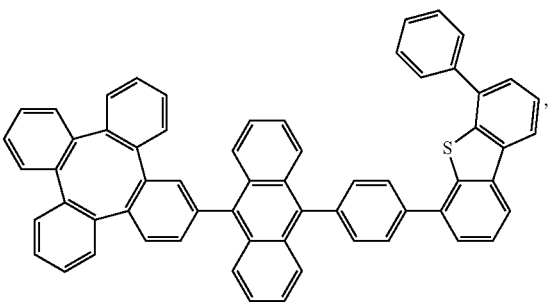
Compound 54
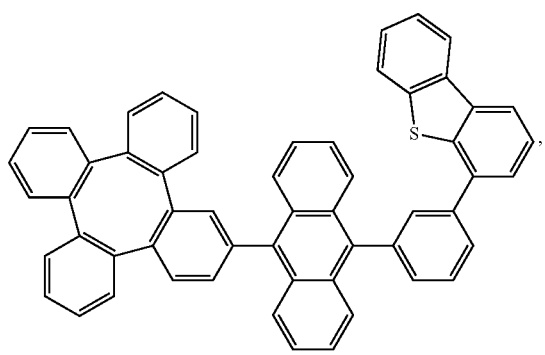
Compound 55
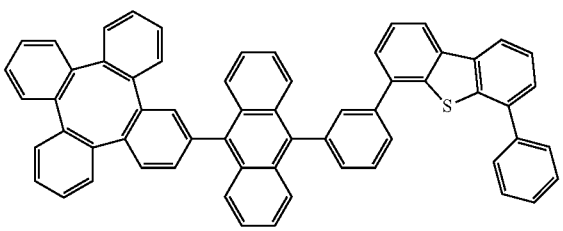
Compound 56
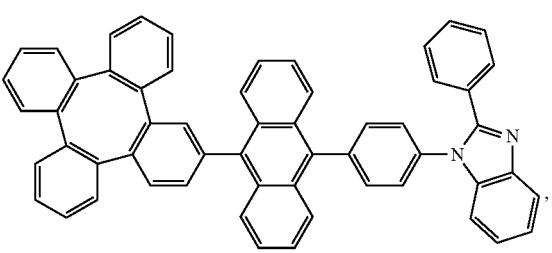

-continued

Compound 57

Compound 58

Compound 59

Compound 60

Compound 61

Compound 62

-continued

Compound 63

Compound 64

Compound 65

Compound 66

Compound 67

Compound 68
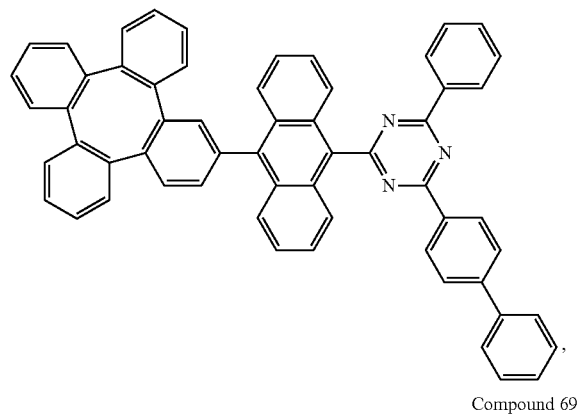
Compound 69
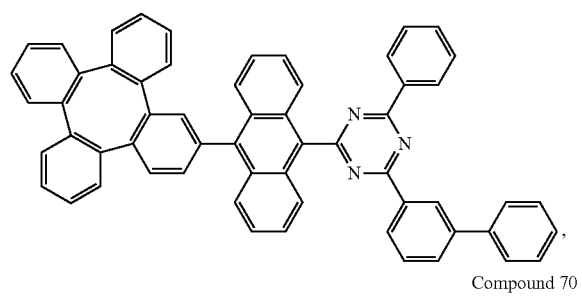
Compound 70
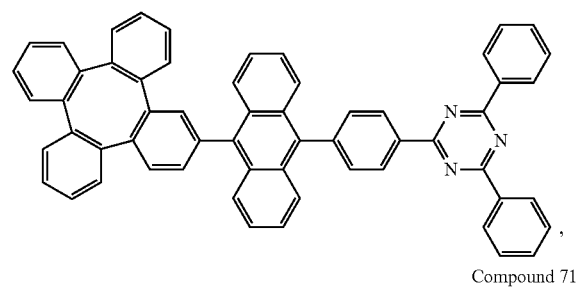
Compound 71
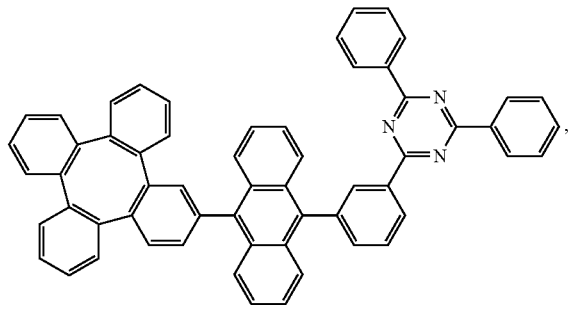
Compound 72
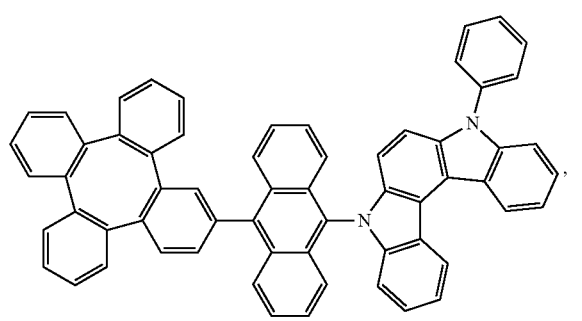
Compound 73
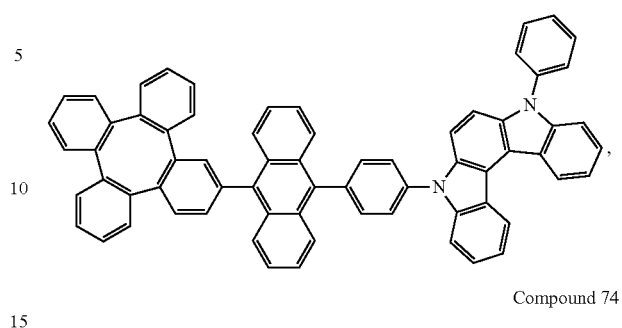
Compound 74
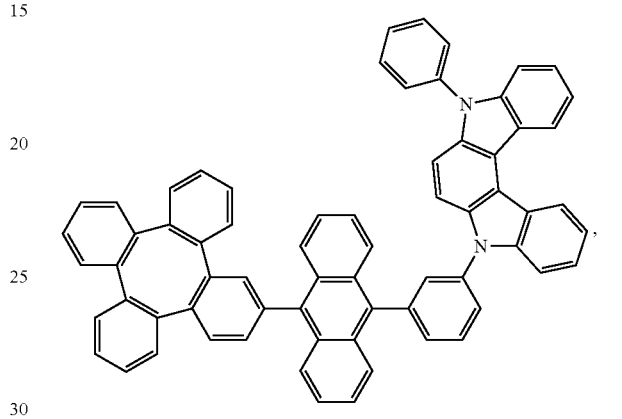
Compound 75
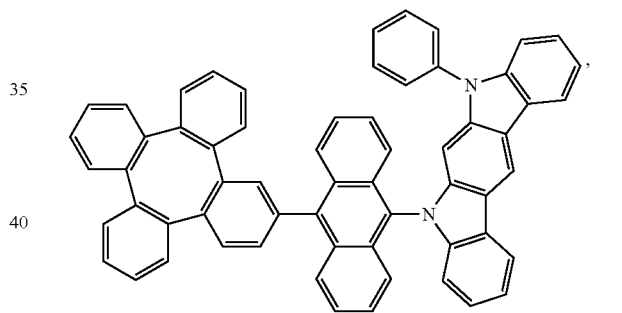
Compound 76
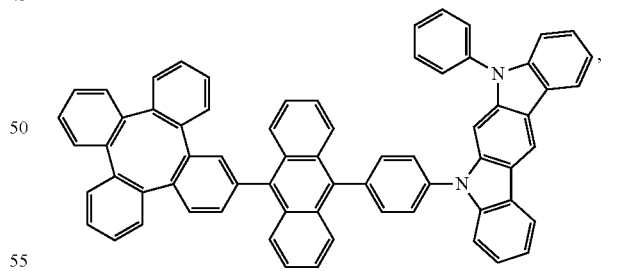
Compound 77
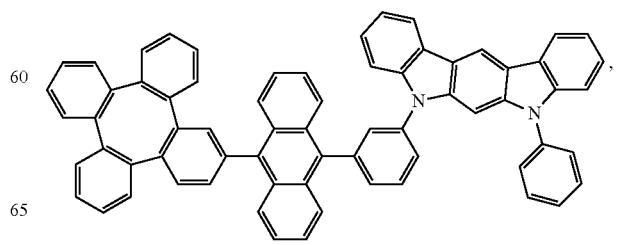

Compound 78
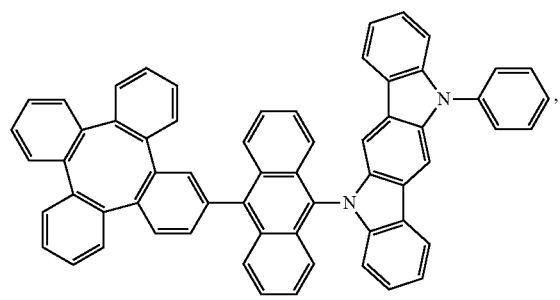
Compound 79
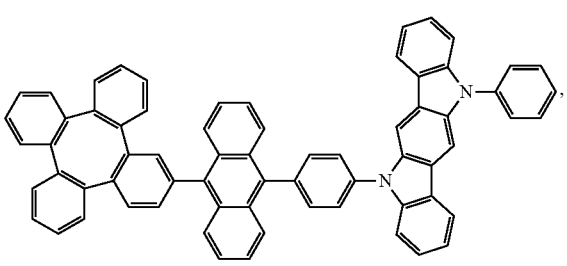
Compound 80
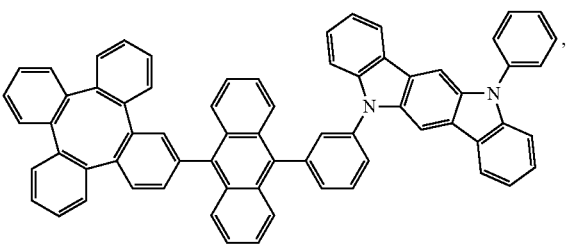
Compound 81
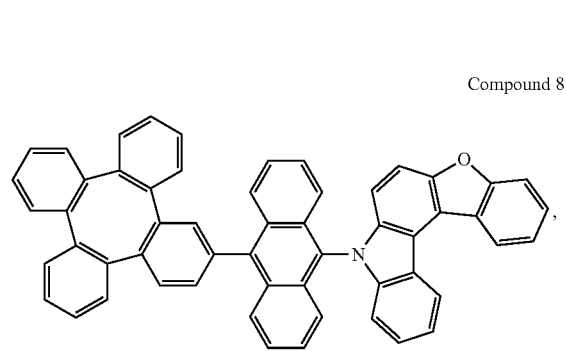
Compound 82
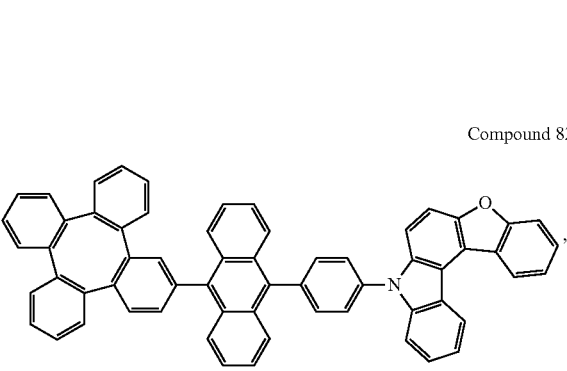
Compound 83
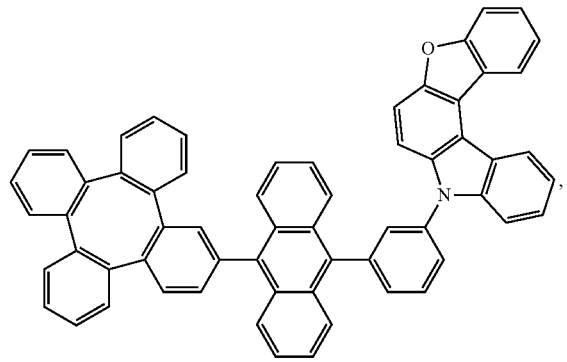
Compound 84
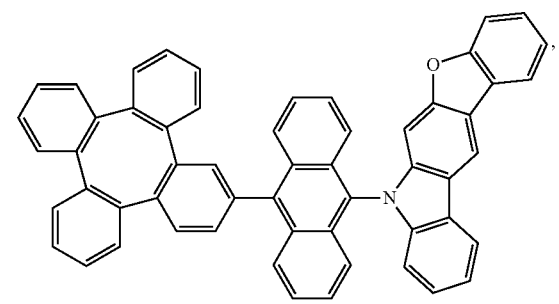
Compound 85
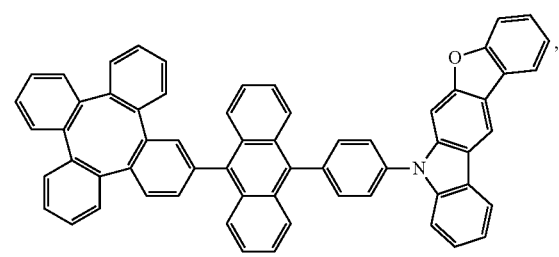
Compound 86
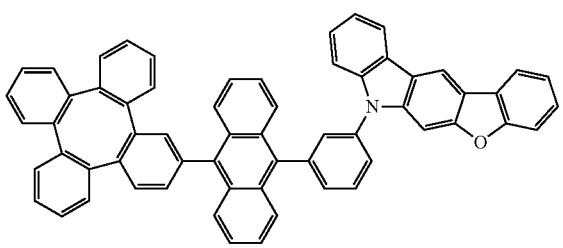
Compound 87
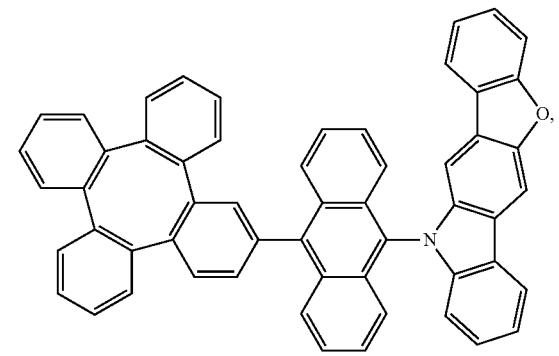

-continued
Compound 88
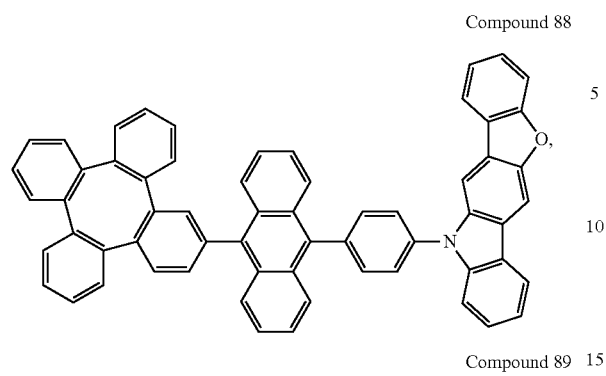
Compound 89
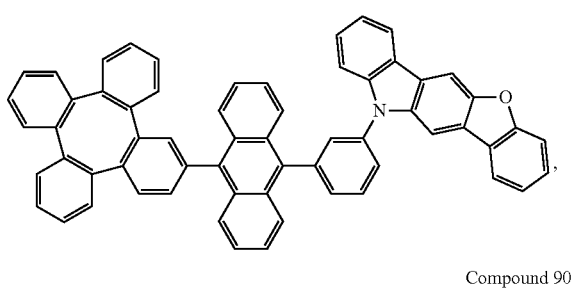
Compound 90
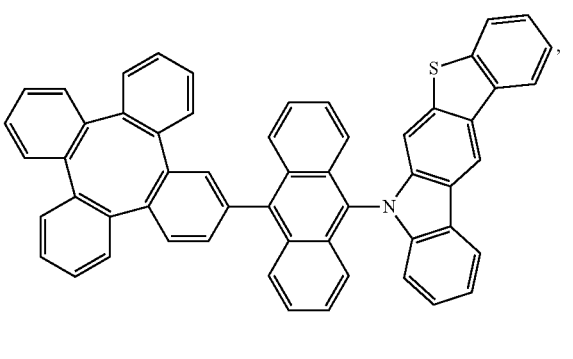
Compound 91
Compound 92
-continued
Compound 93
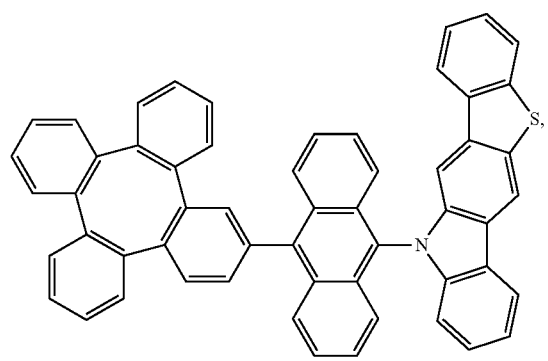
Compound 94
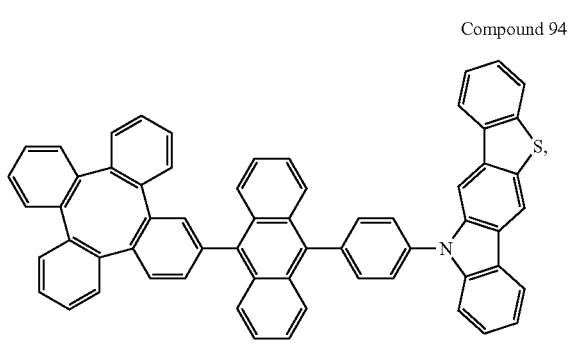
Compound 95
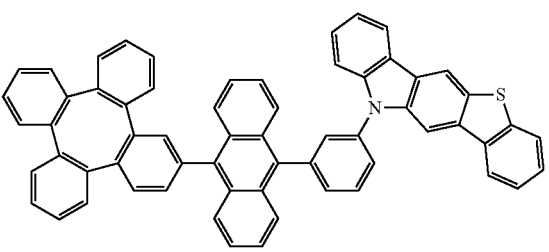
Compound 96
Compound 97
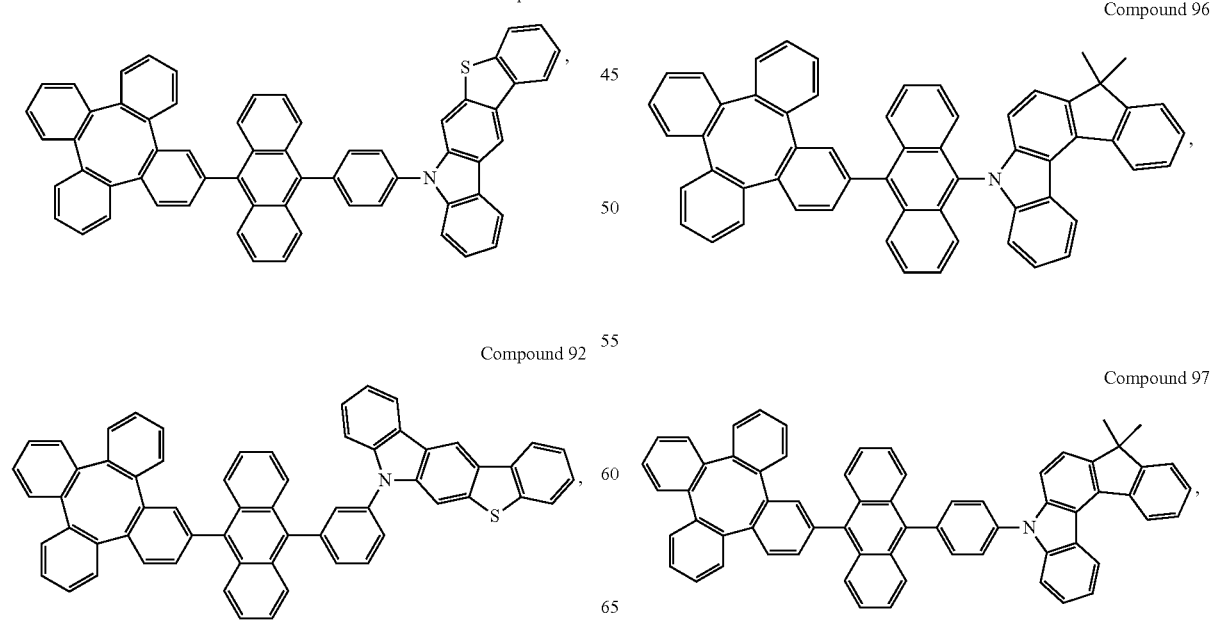

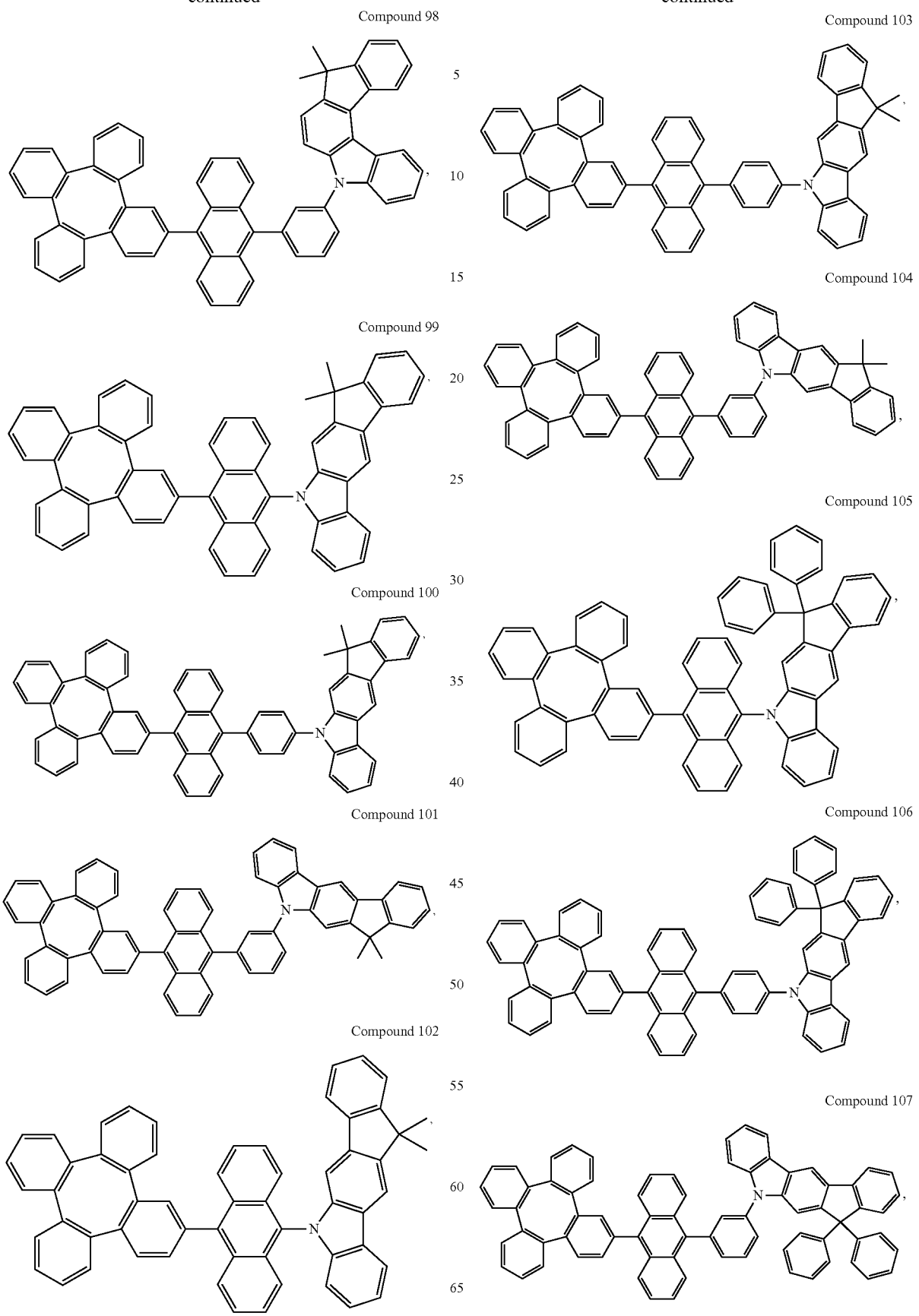

-continued
Compound 108
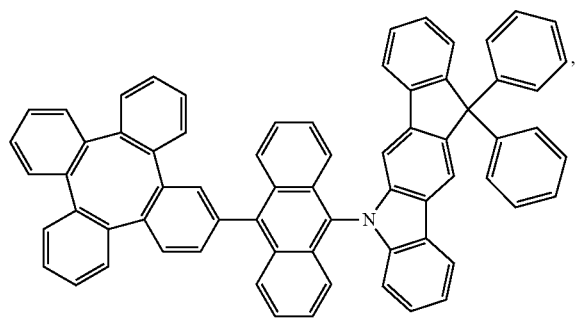
Compound 109
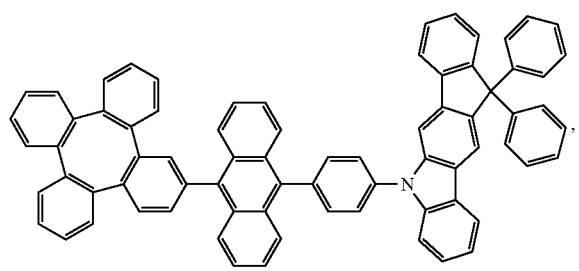
Compound 110
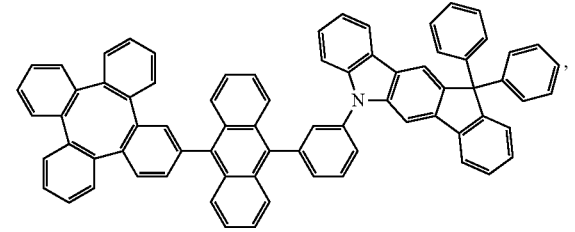
Compound 111
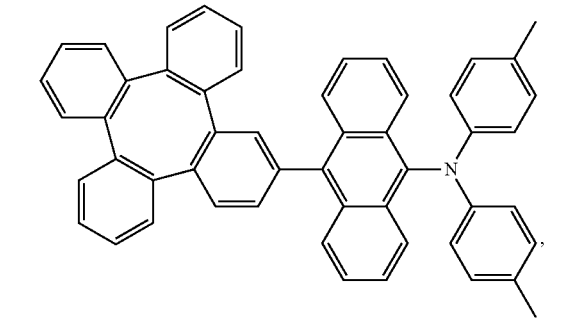
Compound 112
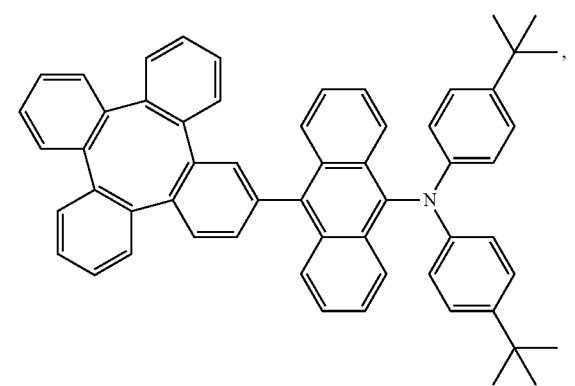
-continued
Compound 113
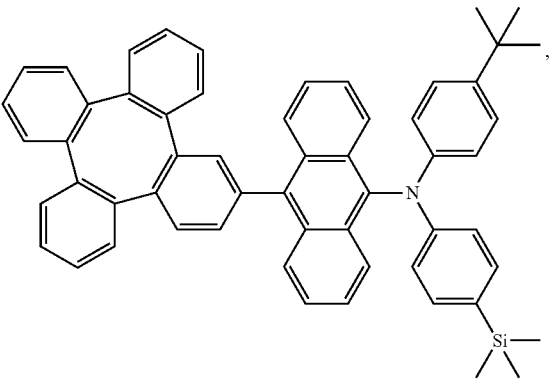
Compound 114
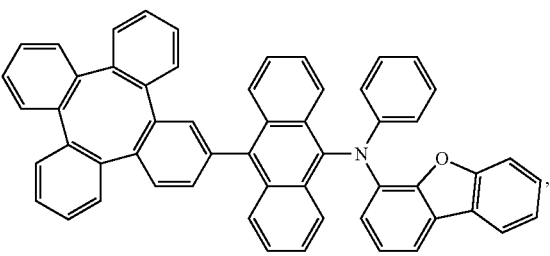
Compound 115
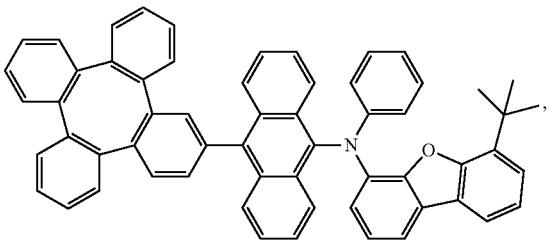
Compound 116
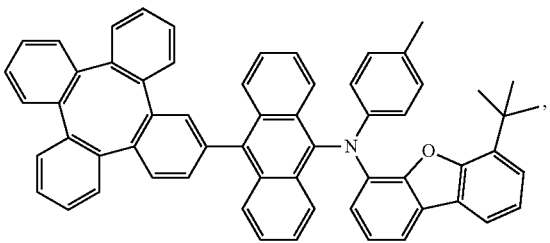
Compound 117

Compound 118
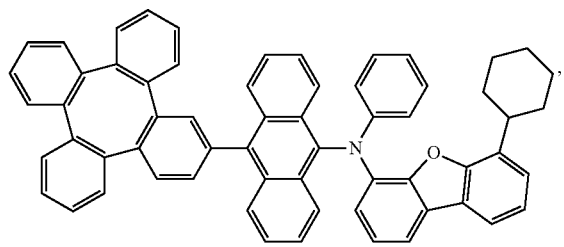
Compound 119
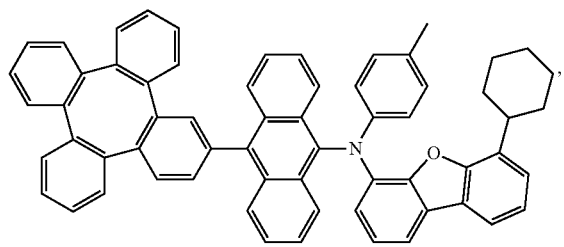
Compound 120
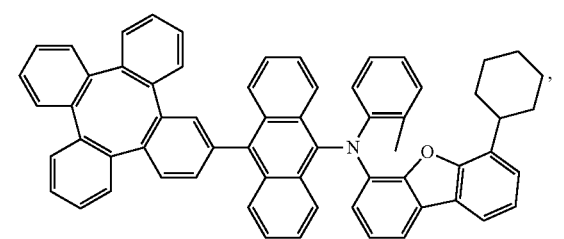
Compound 121
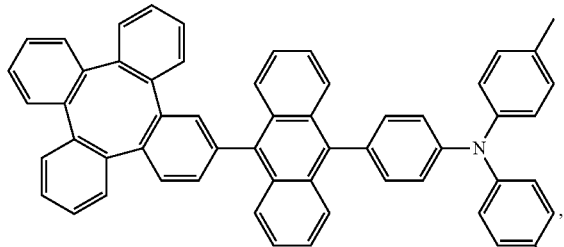
Compound 122
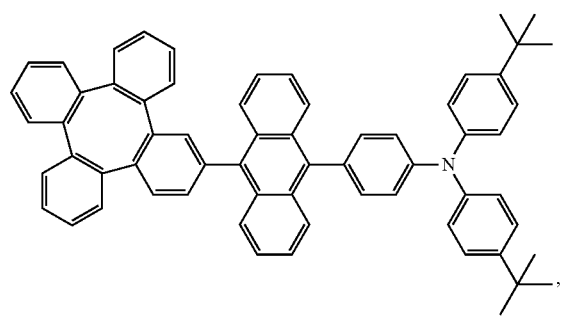
Compound 123
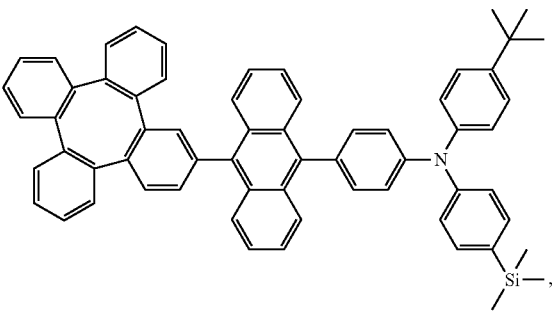
Compound 124
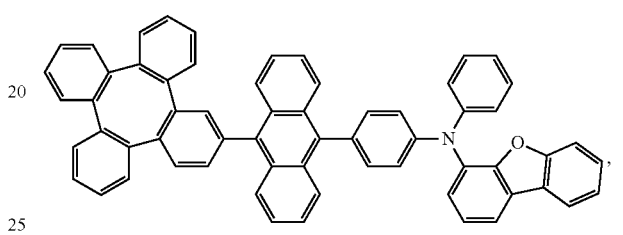
Compound 125
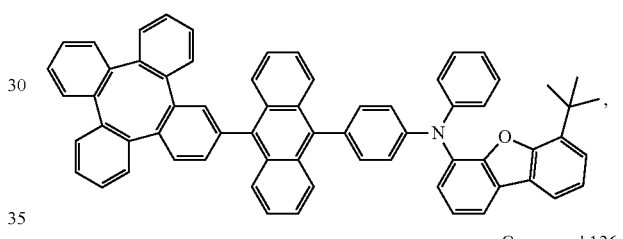
Compound 126
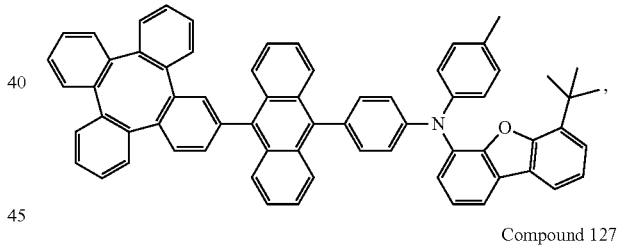
Compound 127
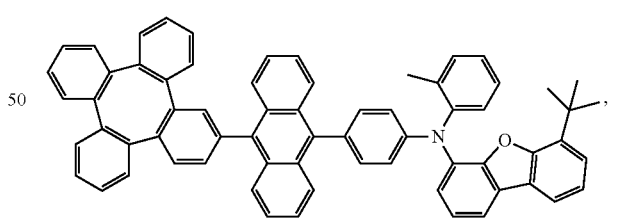
Compound 128
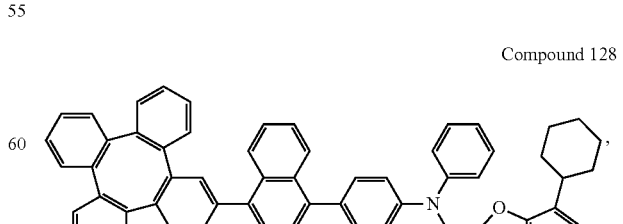

Compound 129

Compound 130

Compound 131

Compound 132

Compound 133

Compound 134

Compound 135

Compound 136

Compound 137

Compound 138

Compound 139

Compound 140
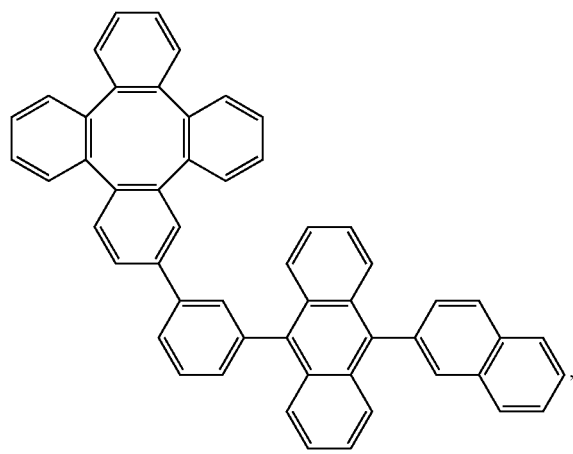
Compound 141
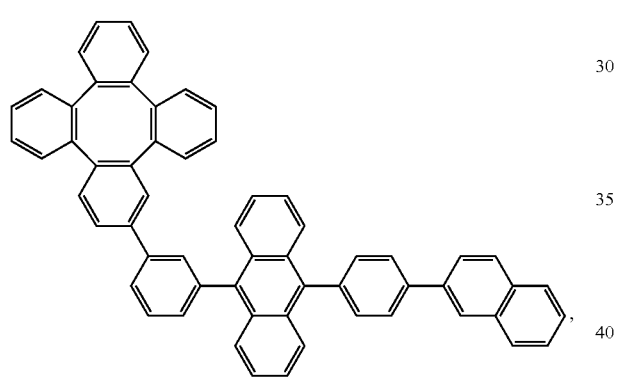
Compound 142
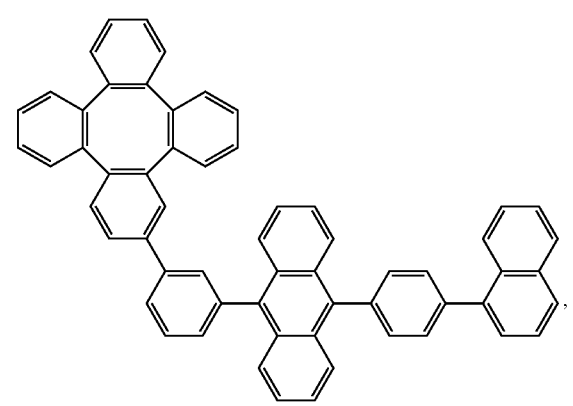
Compound 143
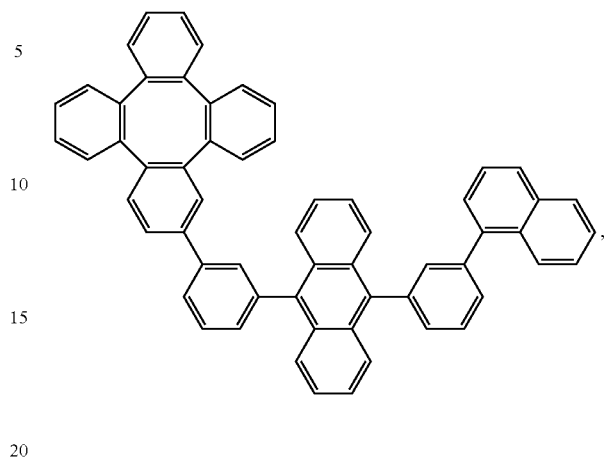
Compound 144
Compound 145
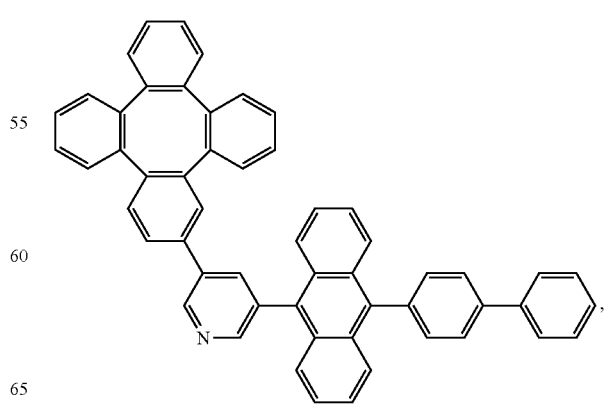

-continued
Compound 146
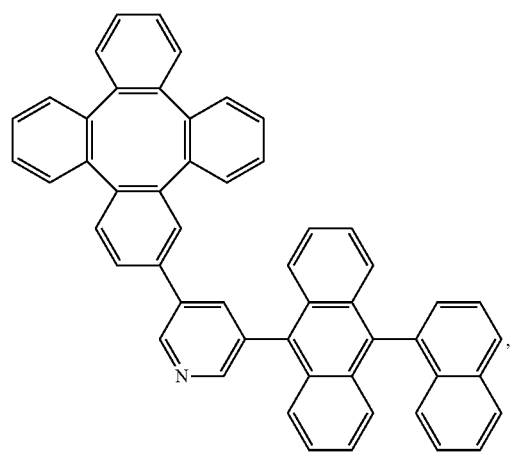
Compound 147
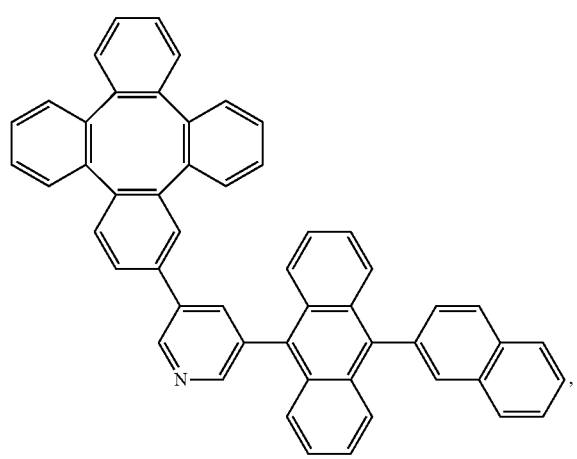
Compound 148
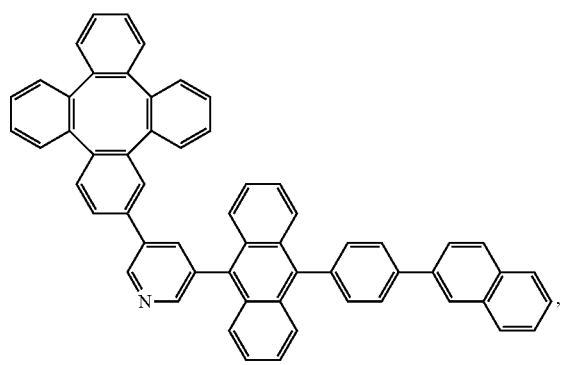
-continued
Compound 149
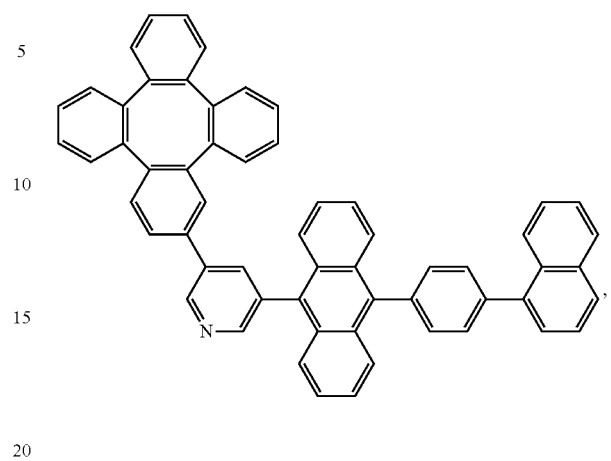
Compound 150
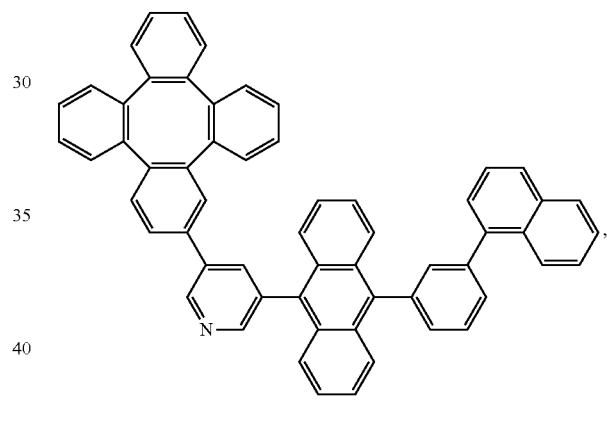
Compound 151
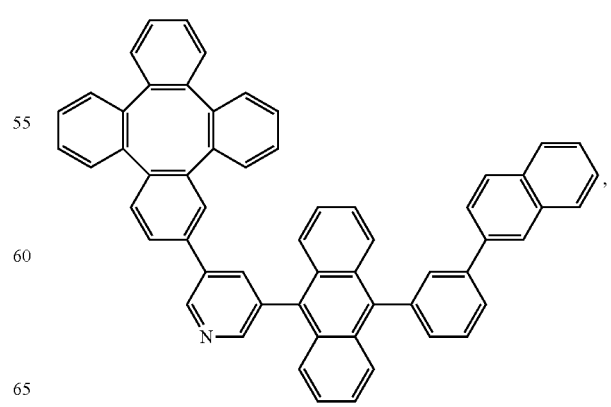

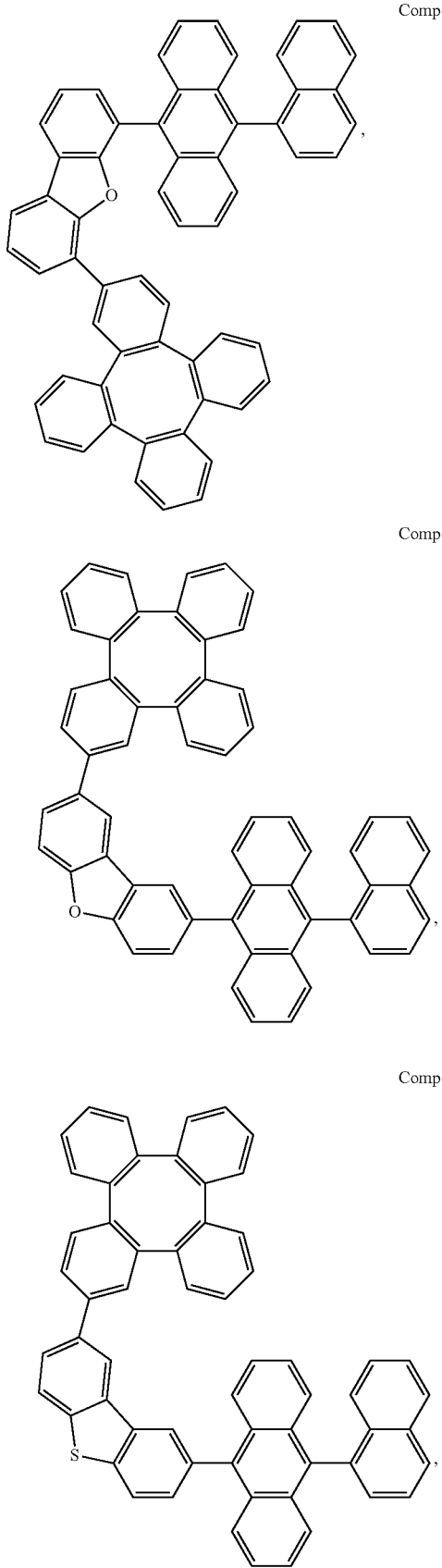
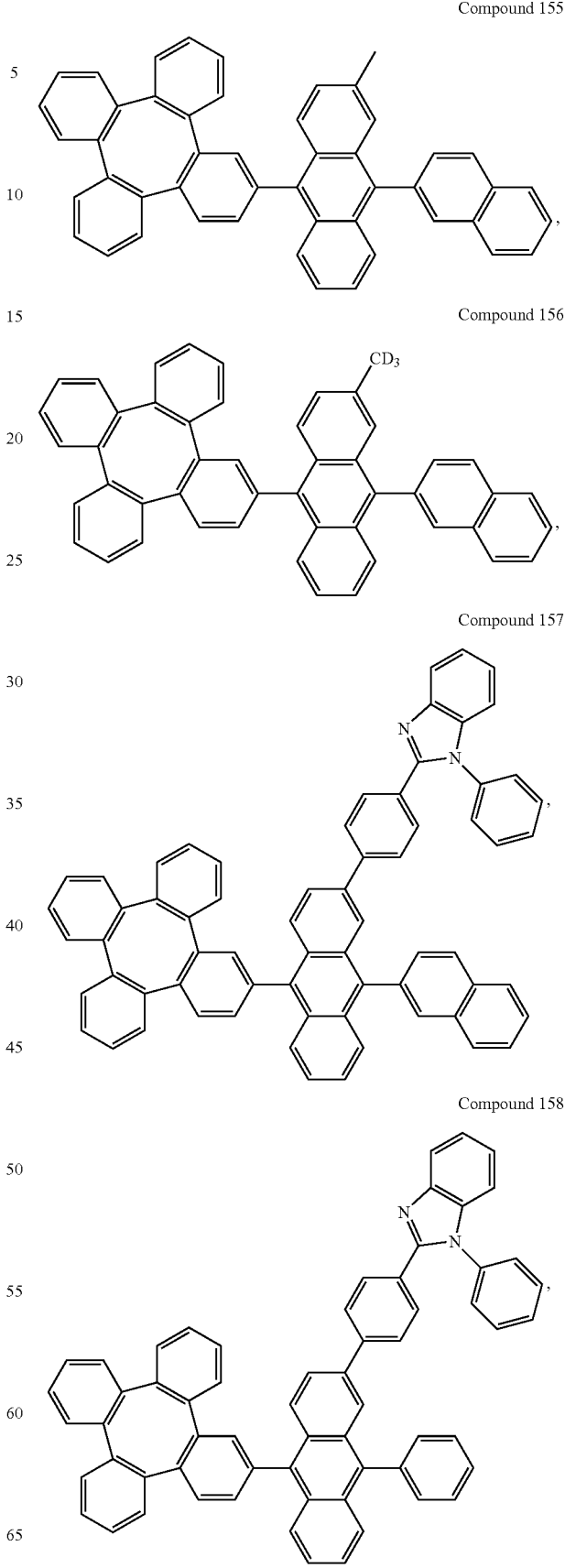

-continued
Compound 159
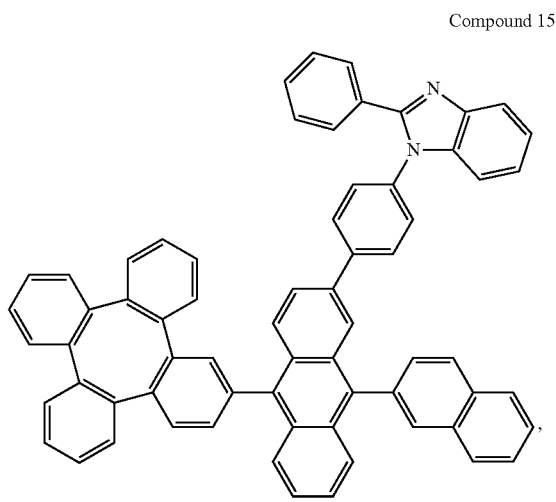
Compound 160
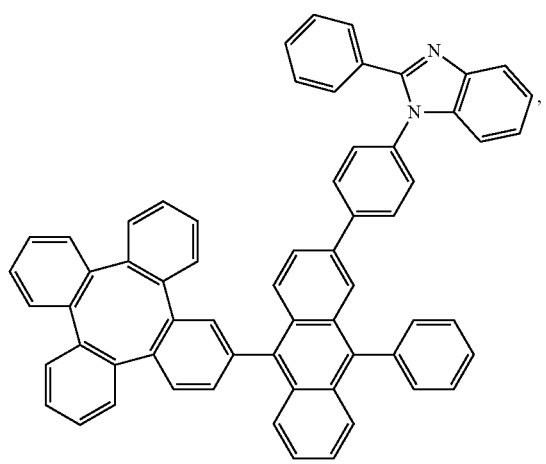
Compound 161
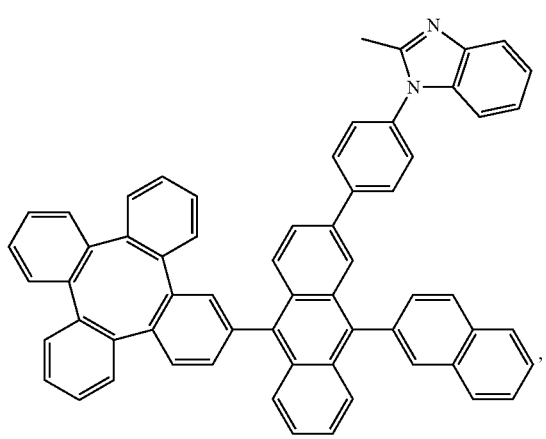
-continued
Compound 162
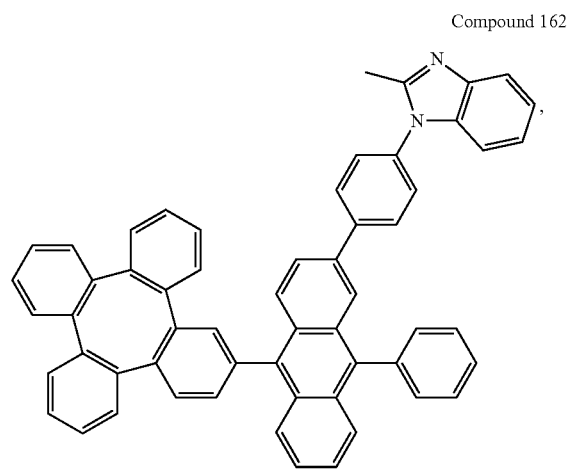
Compound 163
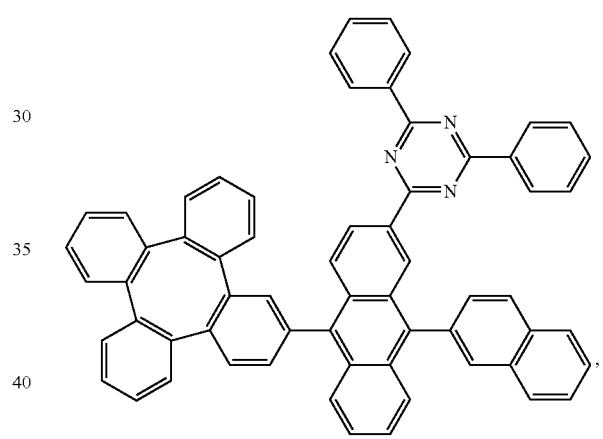
Compound 164
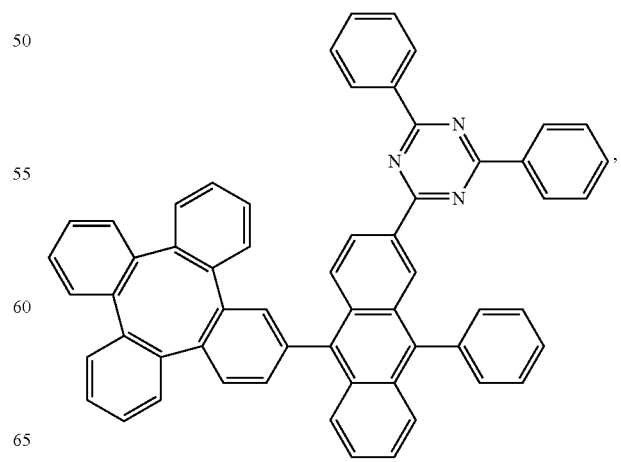

Compound 165
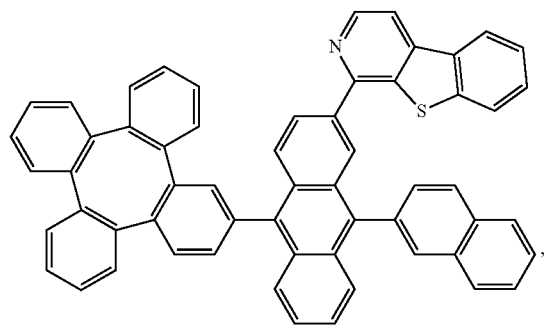
Compound 166
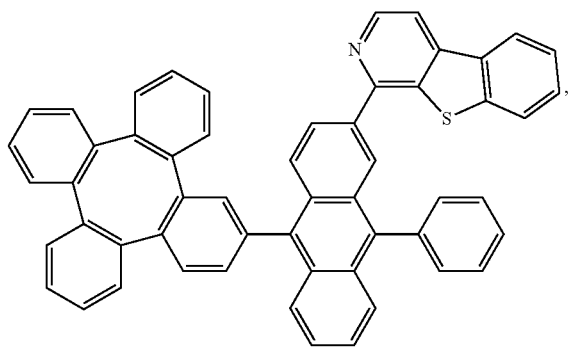
Compound 167
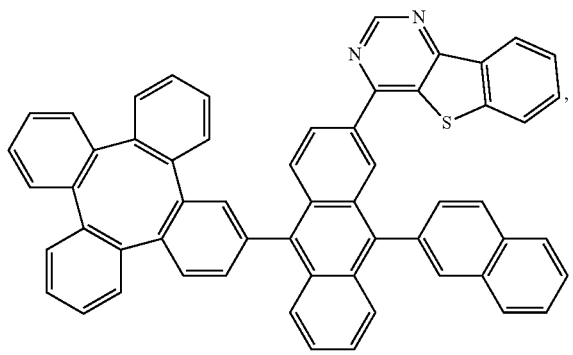
Compound 168
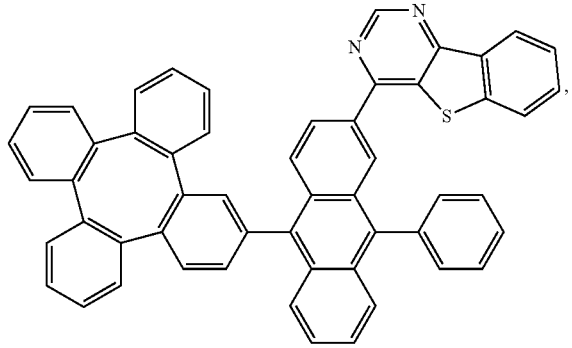
Compound 169
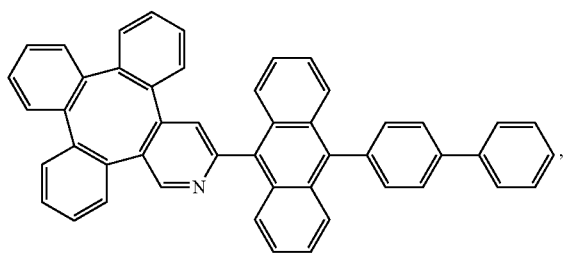
Compound 170
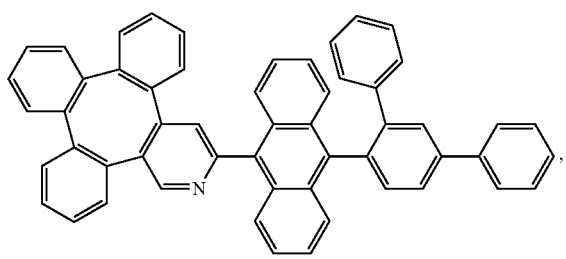
Compound 171
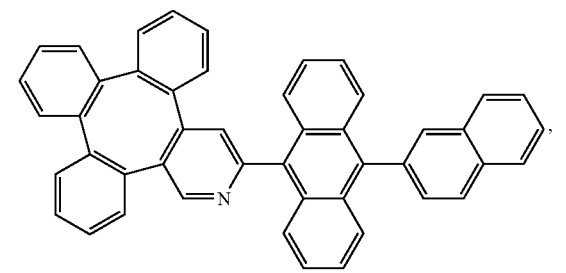
Compound 172
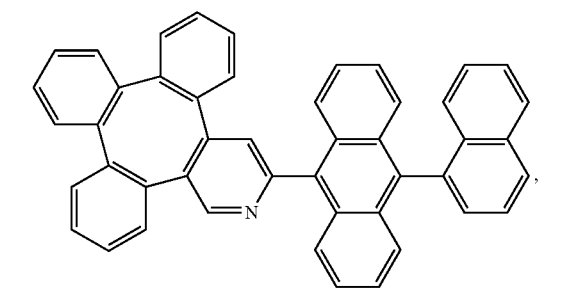
Compound 173
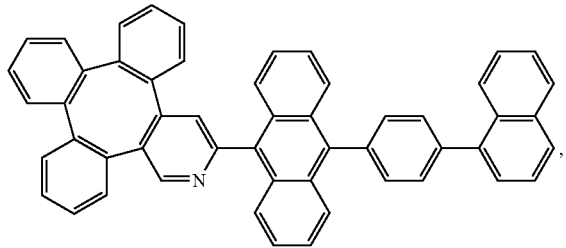

Compound 174
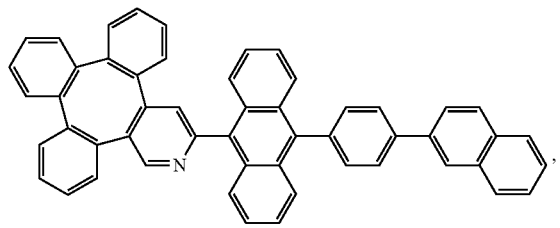
Compound 175
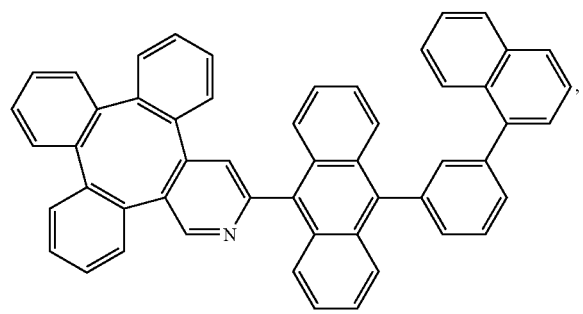
Compound 176
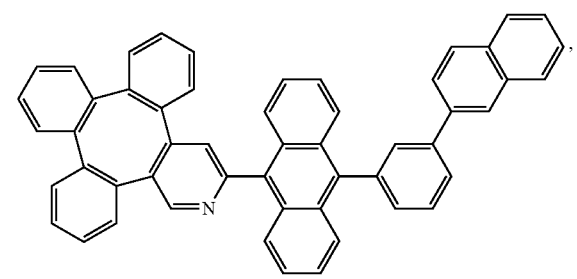
Compound 177
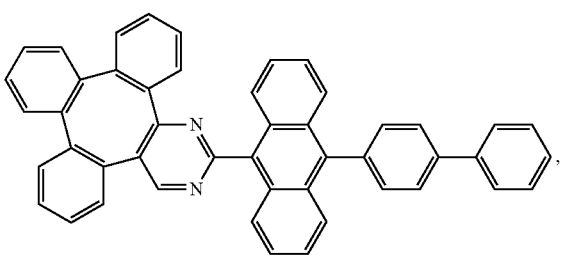
Compound 178
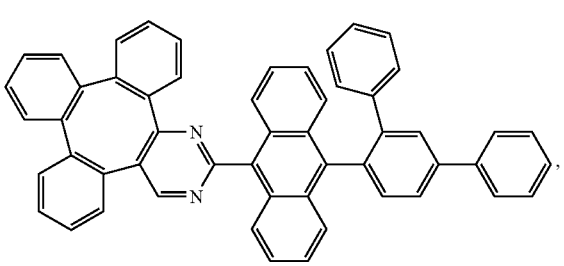
Compound 179
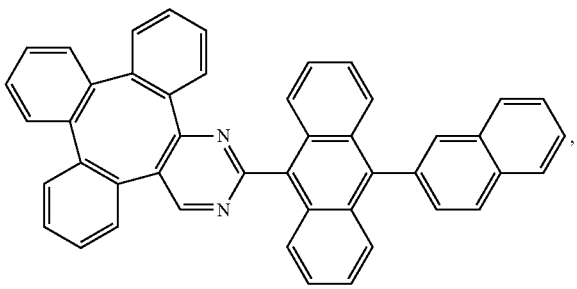
Compound 180
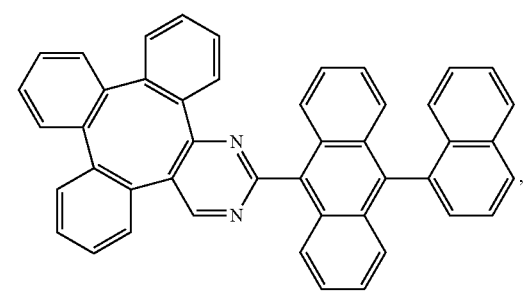
Compound 181
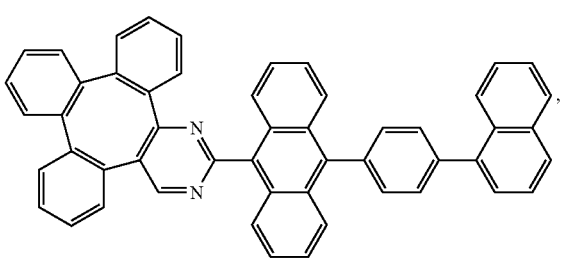
Compound 182
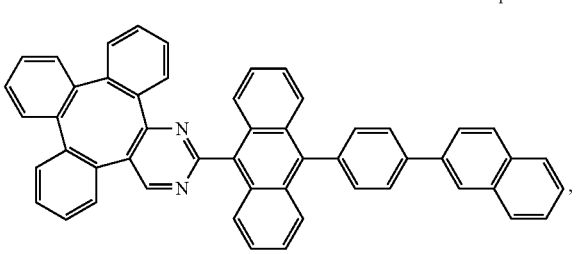
Compound 183
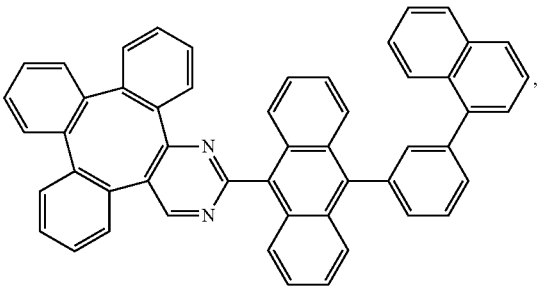

Compound 184

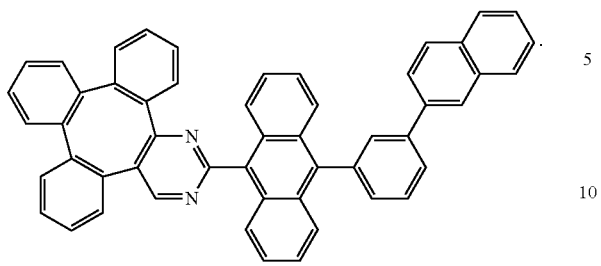

10. An electroluminescent device comprises an anode, a cathode, and an organic layer, disposed between the anode and the cathode, comprising the compound of claim 1.

11. The device of claim 10, wherein the organic layer is a charge transporting layer.

12. The device of claim 10, wherein the organic layer is a light-emitting layer and the compound is a host.

13. The device of claim 10, wherein the organic layer is a light-emitting layer and the compound is an emitter.

14. The device of claim 10, wherein the organic layer further comprises a fluorescent emitter.

15. A formulation comprising the compound of claim 1.

* * * * *